US011357847B2

(12) United States Patent
Mori et al.

(10) Patent No.: US 11,357,847 B2
(45) Date of Patent: Jun. 14, 2022

(54) MODIFIED HSV GD PROTEIN AND VACCINE CONTAINING SAME

(71) Applicant: KM Biologics Co., Ltd., Kumamoto (JP)

(72) Inventors: Hiroaki Mori, Kumamoto (JP); Tomohiro Nishimura, Kumamoto (JP); Hiroyuki Shimizu, Ageo (JP); Akihiro Koube, Kikuyo-machi (JP); Takahiro Katayama, Kawasaki (JP)

(73) Assignee: KM BIOLOGICS CO., LTD., Kumamoto (JP)

( * ) Notice: Subject to any disclaimer, the term of this patent is extended or adjusted under 35 U.S.C. 154(b) by 37 days.

(21) Appl. No.: 16/641,420

(22) PCT Filed: Aug. 29, 2018

(86) PCT No.: PCT/JP2018/032018
§ 371 (c)(1),
(2) Date: Feb. 24, 2020

(87) PCT Pub. No.: WO2019/044925
PCT Pub. Date: Mar. 7, 2019

(65) Prior Publication Data
US 2021/0205441 A1 Jul. 8, 2021

(30) Foreign Application Priority Data

Aug. 30, 2017 (JP) .............................. JP2017-165681

(51) Int. Cl.
A61K 39/245 (2006.01)
A61P 31/22 (2006.01)
C07K 14/005 (2006.01)

(52) U.S. Cl.
CPC ............ A61K 39/245 (2013.01); A61P 31/22 (2018.01); C07K 14/005 (2013.01)

(58) Field of Classification Search
CPC ............ A61K 39/245; A61K 2039/572; A61K 39/12; A61P 31/22; A61P 37/04; C07K 14/005; C12N 2710/16622; C12N 2710/16634; C12N 15/09
See application file for complete search history.

(56) References Cited

U.S. PATENT DOCUMENTS

2006/0051368 A1 3/2006 Spear et al.
2010/0172906 A1 7/2010 Lai et al.

FOREIGN PATENT DOCUMENTS

JP 2003517042 A 5/2003
JP 2015057054 A 3/2015
WO 2001-044477 A1 6/2001
WO 2009/0144755 A1 12/2009
WO 2010/078518 A1 7/2010
WO 2012/106377 A2 8/2012

OTHER PUBLICATIONS

Chiesa MD, Martensen PM, Simmons C, Porakishvili N, Justesen J, Dougan G, Roitt IM, Delves PJ, Lund T. Refocusing of B-cell responses following a single amino acid substitution in an antigen. Immunology. Jun. 2001;103(2):172-8. (Year: 2001).*
Im EJ, Hong JP, Roshorm Y, Bridgeman A, Létourneau S, Liljeström P, Potash MJ, Volsky DJ, McMichael AJ, Hanke T. Protective efficacy of serially up-ranked subdominant CD8+T cell epitopes against virus challenges. PLoS Pathog. May 2011;7(5):e1002041. Epub May 19, 2011. (Year: 2011).*
Patent Cooperation Treaty, International Search Report for PCT/JP2018/032018, dated Dec. 4, 2018, pp. 1-3.
Patent Cooperation Treaty, International Preliminary Report on Patentability for PCT/JP2018/032018, dated Mar. 3, 2020, English translation, pp. 1-3.
Connolly et al., "Structure-Based Analysis of the Herpes Simplex Virus Glycoprotein D Binding Site Present on Herpesvirus Entry Mediator HveA (HVEM)", Journal of Virology, Nov. 2002, pp. 10894-10904, vol. 76(21).
Di Giovine et al., "Structure of Herpes Simplex Virus Glycoprotein D Bound to the Human Receptor Nectin-1", PLoS Pathogens, Sep. 2011, pp. 1-13, vol. 9(7).
Stampfer et al., "Stuck in the middle: structural insights into the role of gH/gL heterodimer in herpesvirus entry", Curr Opin Virol, Feb. 2013, pp. 13-19, vol. 3(1).
Trybala et al., "Herpes Simplex Virus Types 1 and 2 Differ in Their Interaction with Heparan Sulfate", Journal of Virology, Oct. 2000, pp. 9106-9114, vol. 74(19).
Wang et al., "Binding of Herpes Simplex Virus Glycoprotein B (gB) to Paired Immunoglobulin-Like Type 2 Receptor α Depends on Specific Sialylated O-Linked Glycans on gB", Journal of Virology, Dec. 2009, pp. 13042-13045, vol. 83(24).
Carfi et al., "Herpes Simplex Virus Glycoprotein D Bound to the Human Receptor HveA", Molecular Cell, Jul. 2001, pp. 169-179, vol. 8(1).
Krummenacher et al., "Structure of unliganded HSV gD reveals a mechanism for receptor-mediated activation of virus entry", The EMBO Journal, 2005, pp. 4144-4153, vol. 24.
Farley et al., "Recurrent vaginal shedding of herpes simplex type 2 virus in the mouse and effects of antiviral therapy", Antiviral Res., May 2010, pp. 188-195, vol. 86(2).

(Continued)

Primary Examiner — Rachel B Gill
(74) Attorney, Agent, or Firm — Pillsbury Winthrop Shaw Pittman LLP

(57) ABSTRACT

The modified HSV gD protein of the present invention is a modified protein of a herpes simplex virus (HSV) envelope glycoprotein D (gD), wherein the modified HSV gD protein is derived from a wild-type HSV gD by modification of at least one of B cell epitopes having low or no neutralizing antibody-inducing activity compared to a B cell epitope present in a receptor-binding domain (RBD) (decotopes) in the ectodomain of the wild-type HSV gD, so that the modified epitope does not function as an epitope.

18 Claims, 36 Drawing Sheets
Specification includes a Sequence Listing.

(56) References Cited

OTHER PUBLICATIONS

Eggink et al., "Guiding the immune response against influenza virus hemagglutinin toward the conserved stalk domain by hyper glycosylation of the globular head domain", Journal of Virology, Jan. 2014, pp. 699-704, vol. 88(1).
Lu et al., "Crystal structure of herpes simplex virus 2 gD bound to nectin-1 reveals a conserved mode of receptor recognition", Journal of Virology, Dec. 2014, pp. 13678-13688, vol. 88(23).
Lee et al., "Structural basis for the antibody neutralization of herpes simplex virus.", Acta Crystallogr D Biol Crystallogr, Oct. 2013, pp. 1935-1945, vol. 69.
Yu, C. et al., "Replacing the decoy epitope of PCV2b capsid protein with a protective epitope enhances efficacy of PCV2b vaccine", Vaccine, 2016, pp. 6358-6366, vol. 34(50).
Cleveland, SM et al., "Immunogenic and antigenic dominance of a nonneutralizing epitope over a highly conserved neutralizing epitope in the gp41 envelope glycoprotein of human immunodeficiency virus type 1: its deletion leads to a strong neutralizing response", Virology, 2000, pp. 66

(A) RBD peripheral region (B) P50 peripheral region (B)

```
HSV1  -25:MGGAAARLGAVILFVVIVGLHGVRGKYALADASLKMADPNRFRGKDLPVLDQLTDPPGVR   35
HSV2  -25:MGRLTSGVGTAALLVVAVGLRVVCAKYALADPSLKMADPNRFRGKNLPVLDQLTDPPGVK   35

HSV1   36:RVYHIQAGLPDPFQPPSLPITVYYAVLERACRSVLLNAPSEAPQIVRGASEDVRKQFYNL   95
HSV2   36:RVYHIQPSLEDPFQPPSIPITVYYAVLERACRSVLLHAPSEAPQIVRGASDEARKHTYNL   95

HSV1   96:TIAWFRMGGNCAIPITVMEYTECSYNKSLGACPIRTQPRWNYYDSFSAVSEDNLGFLMHA  155
HSV2   96:TIAWYRMGDNCAIPITVMEYTECPYNKSLGVCPIRTQPRWSYYDSFSAVSEDNLGFLMHA  155

HSV1  156:PAFETAGTYLRLVKINDWTEITQFILEHRAKGSCKYALPLREIPPSACLSPQAYQQGVTVD  215
HSV2  156:PAFETAGTYLRLVKINDWTEITQFILEHRARASCKYALPLRIPPAACLTSKAYQQGVTVD  215

HSV1  216:SIGMLPRFIPENQRTVAVYSLKIAGWHGPKAPYTSTLLPPELSETPNATQPELAPEDPED  275
HSV2  216:SIGMLPRFIPENQRTVALYSLKIAGWHGPKPPYTSTLLPPELSDTTNATQPELVPEDPED  275

HSV1  276:SALLEDPVGTVAPQIPPNWHIPSIQDAATPYHPPATPNNMGLIAGAVGGSLLAALVICGI   335
HSV2  276:SALLEDPAGTVSSQIPPNWHIPSIQDVA-PHHAPAAPSNPGLIIGALAGSTLAVLVIGGI   334

HSV1  336:VYWMHRRTRKAPKRIRLPHIREDDQPSSHQPLFY                            369
HSV2  335:AFWVRRRAQMAPKRLRLPHIRDDDAPPSHQPLFY                            368
```

Fig.36

(A) Plaque number-reducing activity of No. 82 antibody against HSV-2 (MS strain)

| | Fc Type (Animal species) | Antibody Type | Concentration | | | | | | | | | | |
|---|---|---|---|---|---|---|---|---|---|---|---|---|---|
| | | | 25 | 12.5 | 6.3 | 3.1 | 1.6 | 0.8 | 0.4 | 0.2 | 0.1 | 0.05 | 0 |
| No.82 | Human-Type | Human-mouse chimeric IgG | 100 | 100 | 99 | 99 | 99 | 89 | 61 | 32 | 14 | 17 | 0 |
| | Mouse-Type | Human-guinea pig chimeric IgG | 98 | 99 | 99 | 100 | 100 | 100 | 98 | 97 | 89 | 74 | 0 |
| | Guinea pig-Type | Human-guinea pig chimeric IgG | 97 | 98 | 98 | 98 | 97 | 92 | 85 | 64 | 45 | 37 | 0 |

(B) Plaque number-reducing activity of No. 82 antibody against HSV-1 (KOS)

| | Fc Type (Animal species) | Antibody Type | Concentration | | | | | | | | | | |
|---|---|---|---|---|---|---|---|---|---|---|---|---|---|
| | | | 25 | 12.5 | 6.3 | 3.1 | 1.6 | 0.8 | 0.4 | 0.2 | 0.1 | 0.05 | 0 |
| No.82 | Human-Type | Human-mouse chimeric IgG | 100 | 99 | 100 | 100 | 100 | 91 | 60 | 24 | 12 | 3 | 0 |
| | Mouse-Type | Human-guinea pig chimeric IgG | 100 | 100 | 100 | 99 | 100 | 100 | 93 | 83 | 66 | 49 | 0 |
| | Guinea pig-Type | Human-guinea pig chimeric IgG | 100 | 100 | 100 | 100 | 99 | 91 | 65 | 28 | 12 | 11 | 0 |

Number: Inhibition rate (%)

MODIFIED HSV GD PROTEIN AND VACCINE CONTAINING SAME

RELATED PATENT APPLICATIONS

This application is based on and claims the benefit of priority from International Application No. PCT/JP2018/032018, filed on Aug. 29, 2018, which claims priority to Japanese Patent Application No. 2017-165681, filed on Aug. 30, 2017, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jul. 30, 2020, is named "KMB-FP18-0824-00_Sub-Sequence_Listing" and is 17.0 KB in size.

TECHNICAL FIELD

The present invention relates to modified HSV gD proteins and vaccines containing the same.

BACKGROUND ART

Human herpes simplex virus (HSV) is a pathogen that has spread widely to humans. HSV, a dsDNA virus, belongs to the alphaherpesviridae subfamily and has two serotypes, HSV-1 and HSV-2. HSV causes a variety of diseases in humans, such as encephalitis, meningitis, lip herpes, genital herpes, skin diseases, corneal herpes, and systemic neonatal herpes. Thus, HSV is a very important virus in health care. In fact, effective antiviral agents such as acyclovir and valacyclovir have been developed.

However, previously developed anti-HSV agents inhibit replication of viral DNA that is proliferating in infected cells, so they do not have an effect on HSVs that latently infect inside the ganglion in a DNA state. That is, when one is infected with HSV, it is not possible to remove the HSV from the latent infection site with an existing anti-HSV agent. To break such a situation, a new vaccine that is both effective in first infection prevention and recurrence prevention needs to be developed.

Pathogens causing an infection are roughly classified into Class I pathogen, which can be achieved sufficient efficacy with conventional vaccines, and Class II pathogen, which cannot be achieved sufficient protective immunity with conventional vaccines or pathogen infection history. As a reason for the difficulty to prevent Class II pathogen, the ingenious immunoediting system they have has been pointed out. The HSV is classified as a Class II pathogen, which is believed that because the HSV has an immunoediting system and ingeniously passes through the host's immune reaction. Regarding the development of HSV vaccine, researches with a weakly toxic live vaccine or an adjuvant inactivated vaccine have been tried. However, either response is inadequate in both of T cell immune and B cell immune and did not differ significantly from the level of inadequate immune responses obtained after natural infection.

The HSV achieves invasion into the host cell through steps such as adsorption to the cell surface, association with a viral receptor, and membrane fusion of the cell membrane and the viral envelope. This system is caused by the association of multiple viral envelope proteins with host cell membrane proteins. Previously, envelope glycoprotein B (gB), envelope glycoprotein C (gC), envelope glycoprotein D (gD), envelope glycoprotein H (gH), envelope glycoprotein L (gL) have been known, and among these viral envelope proteins, gD is initially complexed with the host cell membrane receptor, herpesvirus entry mediator (HVEM), Nectin-1, or Nectin-2. Crystal structures have been reported for the complex (Non Patent Literatures 1 and 2). The structurally altered gD interacts with gH/gL, and the activated gH/gL further activates gB (Non Patent Literature 3). gB is believed to play a major function of membrane fusion through the receptor 3-O-sulfonated heparan sulfate (3-OS HS) or PILRα (Non Patent Literatures 4 and 5). Thus, it has been suggested that binding of HSV gD to receptors is a trigger for viral entry.

CITATION LIST

Non Patent Literature

Non Patent Literature 1: S. A. Connolly et al., "Structure-Based Analysis of the Herpes Simplex Virus Glycoprotein D Binding Site Present on Herpesvirus Entry Mediator HveA (HVEM)", JOURNAL OF VIROLOGY, Vol. 76, No. 21, November 2002, pages 10894-10904, ISSN: 0022-538X Non Patent Literature 2: P. Di Giovine et al., "Structure of Herpes Simplex Virus Glycoprotein D Bound to the Human Receptor Nectin-1", PLoS Pathogens, Vol. 9, No. 7, September 2011

Non Patent Literature 3: S. D. Stampfer et al., "Stuck in the middle: structural insights into the role of gH/gL heterodimer in herpesvirus entry", Curr Opin Virol, Vol. 3, No. 1, February 2013, pages 13-19

Non Patent Literature 4: E. Trybala et al., "Herpes Simplex Virus Types 1 and 2 Differ in Their Interaction with Heparan Sulfate", JOURNAL OF VIROLOGY, Vol. 74, No. 19, October 2000, pages 9106-9114, ISSN: 0022-538X Non Patent Literature 5: J. Wang et al., "Binding of Herpes Simplex Virus Glycoprotein B (gB) to Paired Immunoglobulin-Like Type 2 Receptor a Depends on Specific Sialylated 0-Linked Glycans on gB", JOURNAL OF VIROLOGY, Vol. 83, No. 24, December 2009, pages 13042-13045, ISSN: 0022-538X Non Patent Literature 6: A. Carfi et al., "Herpes Simplex Virus Glycoprotein D Bound to the Human Receptor HveA", Molecular Cell, Vol. 8, No. 1, July. 2001, pages 169-179

Non Patent Literature 7: C. Krummenacher et al., "Structure of unliganded HSV gD reveals a mechanism for receptor-mediated activation of virus entry", The EMBO Journal, Vol. 24, 2005, pages 4144-4153

Non Patent Literature 8: N. Farley et al., "Recurrent vaginal shedding of herpes simplex type 2 virus in the mouse and effects of antiviral therapy", Antiviral Res. 2010 May; 86(2): 188-195.

Non Patent Literature 9: J. R. Gallagher et al., "Displacement of the C terminus of herpes simplex virus gD is sufficient to expose the fusion-activating interfaces on gD", JOURNAL OF VIROLOGY, Vol. 87, No. 23, December 2013, pages 12656-12666, ISSN: 0022-538X Non Patent Literature 10: D. Eggink et al., "Guiding the immune response against influenza virus hemagglutinin toward the conserved stalk domain by hyperglycosylation of the globular head domain", JOURNAL OF VIROLOGY, Vol. 88, No. 1, January 2014, pages 699-704, ISSN: 0022-538X Non Patent Literature 11: Lu. G et al., "Crystal structure of herpes simplex virus 2 gD bound to nectin-1 reveals a conserved mode of receptor recognition", JOURNAL OF VIROLOGY, Vol. 88, No. 23, December 2014, pages 13678-13688

Non Patent Literature 12: Lee. C C et al., "Structural basis for the antibody neutralization of herpes simplex virus.", Acta Crystallogr D Biol Crystallogr, Vol. 69, October 2013, pages 1935-45

SUMMARY OF INVENTION

Technical Problem

As discussed above, antiviral drugs such as acyclovir have been used to treat HSV. However, these antiviral drugs cannot completely remove the virus, and the virus reactivates when taking of the drugs is stopped. Thus, while it is desirable to develop a preventive vaccine that prevents infection of HSV itself or a therapeutic vaccine that relieves symptoms of recurrence, currently there is no valid vaccine and its unmet needs are high.

An object of the present invention is to provide modified HSV gD proteins and vaccines containing the same that can induce, upon immune induction, immune serum containing a higher percentage of neutralizing antibodies that exhibit higher neutralizing activity against HSV gD compared to wild-type HSV gD and can be utilized for the prevention and/or treatment of HSV infections.

Solution to Problem

For gD proteins known as one of the major preventive antigens of HSV, the present inventors attempted to perform comprehensive B cell epitope analysis and T cell epitope analysis to classify beneficial epitopes and unbeneficial or deleterious epitopes in preventive activity expression. Then, by de-epitoping unbeneficial or deleterious epitope, leading to immunologically emphasis of the beneficial epitope, or by adding a beneficial epitope such as a promiscuous T cell epitope, the present inventors have attempted to induce immune refocusing and enhance neutralizing antibody induction and cellular immunity, and, as the result, have completed a modified HSV gD vaccine that has enhanced infection prevention ability.

That is, the present invention relates to each of the following inventions:
(1) A modified protein of a herpes simplex virus (HSV) envelope glycoprotein D (gD) (modified HSV gD protein), wherein the modified HSV gD protein is derived from a wild-type HSV gD by modification of at least one of B cell epitopes having low or no neutralizing antibody-inducing activity compared to a B cell epitope present in a receptor-binding domain (RBD) (decotopes) in the ectodomain of the wild-type HSV gD, so that the modified epitope does not function as an epitope. (2) The modified HSV gD protein according to (1), wherein the B cell epitope present in the RBD is an epitope containing an amino acid residue corresponding to at least one amino acid residue selected from the group consisting of an arginine residue at position 134, an aspartic acid residue at position 139, and 222nd arginine residue in the amino acid sequence set forth in SEQ ID NO: 1.

(3) The modified HSV gD protein according to (1) or (2), wherein the decotope is a B cell epitope present in the N-terminal proline-rich region (PRR) of the gD ectodomain.
(4) The modified HSV gD protein according to (3), wherein the decotope is:
an epitope containing an amino acid residue corresponding to a proline residue at position 50 in the amino acid sequence set forth in SEQ ID NO: 1 in the ectodomain of the wild-type HSV gD; or
an epitope containing at least one amino acid residue present in a region at a distance of 1.5 nm or less from an amino acid corresponding to the proline residue at position 50 in a surface of a crystal structure of the ectodomain of the wild-type HSV gD.
(5) The modified HSV gD protein according to any one of (1) to (4), wherein the modification of the decotope is performed by substitution of an amino acid residue, deficiency of an amino acid residue, and/or introducing a glycochain by substitution or deficiency of an amino acid residue.
(6) The modified HSV gD protein according to (5), wherein the modification of the decotope includes a modification by introducing a glycochain to an amino acid residue corresponding to a proline residue at position 50 in the amino acid sequence set forth in SEQ ID NO: 1 in the ectodomain of the wild-type HSV gD.
(7) The modified HSV gD protein according to (5) or (6), wherein the modification of the decotope includes a modification by introducing a glycochain to an amino acid residue corresponding to proline at position 74 in the amino acid sequence set forth in SEQ ID NO: 1 in the ectodomain of the wild-type HSV gD.
(8) The modified HSV gD protein according to any one of (5) to (7), wherein the modification of the decotope includes a modification by introducing a glycochain to an amino acid residue corresponding to an arginine residue at position 186 in the amino acid sequence set forth in SEQ ID NO: 1 in the ectodomain of the wild-type HSV gD.
(9) The modified HSV gD protein according to (5), wherein
the ectodomain of the wild-type HSV gD consists of the amino acid sequence set forth in SEQ ID NO: 1; and
the modification of the decotope includes at least one modification selected from the group consisting of:
a modification by introducing a glycochain by substitution of a proline residue at position 50 with an asparagine residue and substitution of a proline residue at position 51 with an amino acid residue other than a proline residue in the amino acid sequence set forth in SEQ ID NO: 1;
a modification by introducing a glycochain by substitution of a proline residue at position 74 with an asparagine residue and substitution of a glutamic acid residue at position 76 with a serine residue in the amino acid sequence set forth in SEQ ID NO: 1; and
a modification by introducing a glycochain by substitution of an arginine residue at position 186 with an asparagine residue in the amino acid sequence set forth in SEQ ID NO: 1.
(10) The modified HSV gD protein according to any one of (5) to (9), wherein the glycochain is an N-type glycochain.
(11) The modified HSV gD protein according to any one of (1) to (10), wherein the modified HSV gD protein further comprises at least one promiscuous T cell epitope linked at a C-terminal side of the ectodomain of the HSV gD.
(12) The modified HSV gD protein according to (11), wherein the promiscuous T cell epitope is a promiscuous T cell epitope consisting of the amino acid sequence set forth in SEQ ID NO: 4, SEQ ID NO: 5, SEQ ID NO: 6, SEQ ID NO: 7, or SEQ ID NO: 8.

(13) The modified HSV gD protein according to (12), wherein the promiscuous T cell epitope is a promiscuous T cell epitope consisting of the amino acid sequence set forth in SEQ ID NO: 8.

(14) The modified HSV gD protein according to any one of (1) to (13), wherein the modified HSV gD protein further contains deficiency of at least a portion of amino acid residues corresponding to amino acid residues at positions 251 to 315 in the amino acid sequence set forth in SEQ ID NO: 1 in the wild-type HSV gD.

(15) The modified HSV gD protein according to any one of (1) to (14), wherein the modified HSV gD protein further includes a modification by substitution of an amino acid residue corresponding to a valine residue at position 231 with another amino acid residue in the amino acid sequence set forth in SEQ ID NO: 1 in the ectodomain of the wild-type HSV gD.

(16) The modified HSV gD protein according to any one of (1) to (15), wherein the HSV is HSV-1 or HSV-2.

(17) An HSV vaccine comprising the modified HSV gD protein according to any one of (1) to (16).

(18) A modified protein of a herpes simplex virus (HSV) envelope glycoprotein D (gD) (modified HSV gD protein), wherein the modified HSV gD protein is derived from a wild-type HSV gD by modification of at least one of B cell epitopes present in the N-terminal proline-rich region (PRR) in the ectodomain of the wild-type HSV gD, so that the modified epitope does not function as an epitope.

(19) The modified HSV gD protein according to (18), wherein the B cell epitope present in the PRR is:
an epitope containing an amino acid residue corresponding to a proline residue at position 50 in the amino acid sequence set forth in SEQ ID NO: 1 in the ectodomain of the wild-type HSV gD; or
an epitope containing at least one amino acid residue present in a region at a distance of 1.5 nm or less from an amino acid corresponding to the proline residue at position 50 in a surface of a crystal structure of the ectodomain of the wild-type HSV gD.

(20) The modified HSV gD protein according to (18) or (19), wherein the modification is performed by introducing a glycochain by substitution or deficiency of an amino acid residue.

(21) The modified HSV gD protein according to (20), wherein the modification includes a modification by introducing a glycochain to an amino acid residue corresponding to a proline residue at position 50 in the amino acid sequence set forth in SEQ ID NO: 1 in the ectodomain of the wild-type HSV gD.

(22) The modified HSV gD protein according to (20) or (21), wherein the modification includes a modification by introducing a glycochain to an amino acid residue corresponding to a proline residue at position 74 in the amino acid sequence set forth in SEQ ID NO: 1 in the ectodomain of the wild-type HSV gD.

(23) The modified HSV gD protein according to any one of (20) to (22), wherein the modification includes a modification by introducing a glycochain to an amino acid residue corresponding to an arginine residue at position 186 in the amino acid sequence set forth in SEQ ID NO: 1 in the ectodomain of the wild-type HSV gD. (24) The modified HSV gD protein according to (20), wherein
the ectodomain of the wild-type HSV gD consists of the amino acid sequence set forth in SEQ ID NO: 1; and the modification includes at least one modification selected from the group consisting of:
a modification by introducing a glycochain by substitution of a proline residue at position 50 with an asparagine residue and substitution of a proline residue at position 51 with an amino acid residue other than a proline residue in the amino acid sequence set forth in SEQ ID NO: 1;
a modification by introducing a glycochain by substitution of a proline residue at position 74 with an asparagine residue and substitution of a glutamic acid residue at position 76 with a serine residue in the amino acid sequence set forth in SEQ ID NO: 1; and
a modification by introducing a glycochain by substitution of an arginine residue at position 186 with an asparagine residue in the amino acid sequence set forth in SEQ ID NO: 1.

(25) The modified HSV gD protein according to any one of (19) to (24), wherein the modified HSV gD protein further comprises at least one promiscuous T cell epitope linked at a C-terminal side of the ectodomain of the HSV gD.

(26) The modified HSV gD protein according to (25), wherein the promiscuous T cell epitope is a promiscuous T cell epitope consisting of the amino acid sequence set forth in SEQ ID NO: 4, SEQ ID NO: 5, SEQ ID NO: 6, SEQ ID NO: 7, or SEQ ID NO: 8.

(27) The modified HSV gD protein according to (26), wherein the promiscuous T cell epitope is a promiscuous T cell epitope consisting of the amino acid sequence set forth in SEQ ID NO: 8.

ADVANTAGEOUS EFFECTS OF INVENTION

When immunity is induced by modified HSV gD proteins of the present invention and vaccines comprising the same, relatively more neutralizing antibodies with higher neutralizing activity can be contained in serum as compared to when immunity is induced by wild-type HSV gD. That is, the modified HSV gD proteins of the present invention and vaccines containing the same can induce immune refocusing and provide a strong protective effect against HSV. Thus, high preventive and therapeutic effects can be expected against HSV infections.

BRIEF DESCRIPTION OF DRAWINGS

Figure 27:
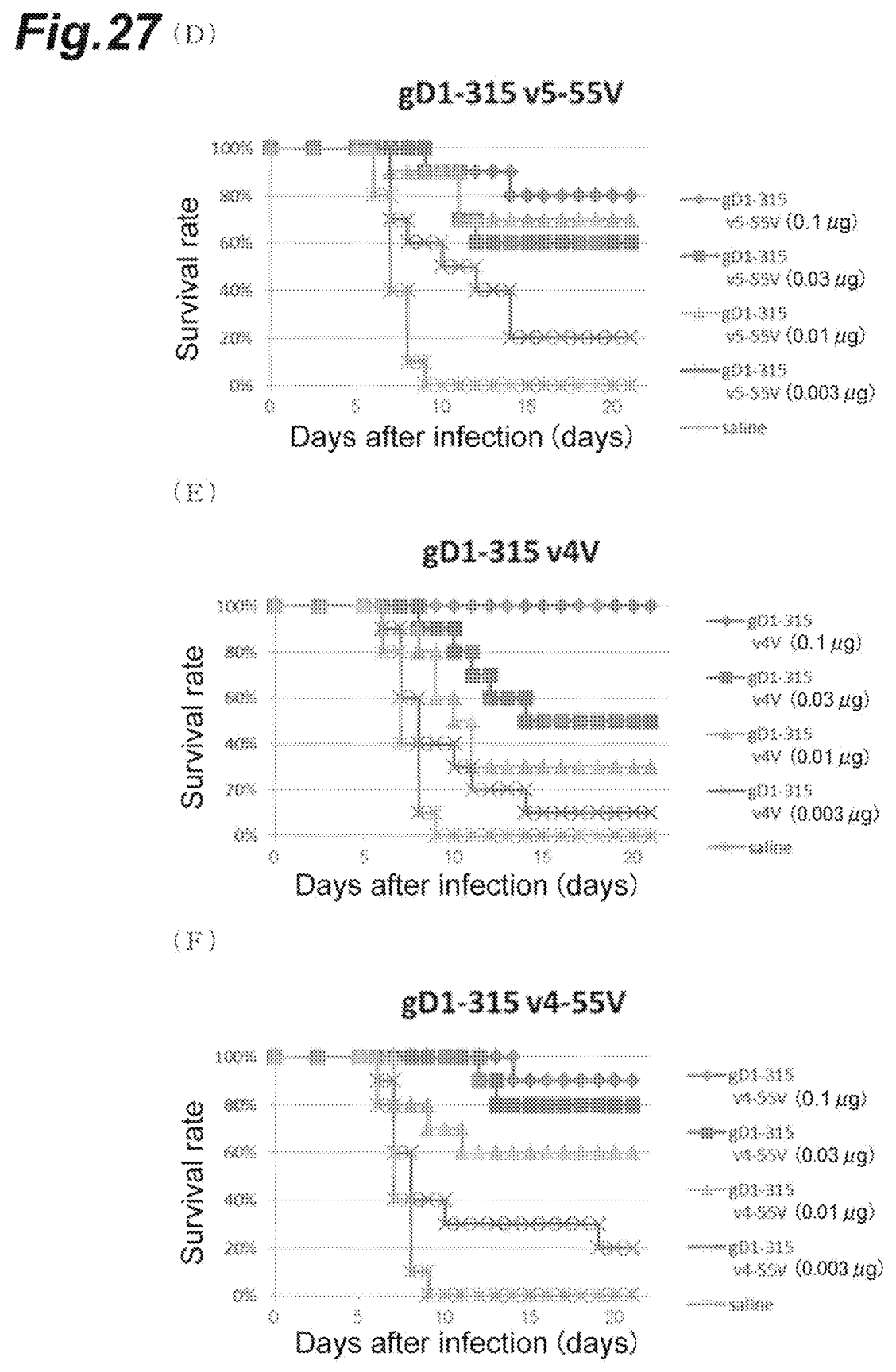

FIG. 27 presents diagrams showing the survival rate of mouse infection-prevention test Experiment 1 of the modified gD in Example 9.

FIG. 29 presents diagrams showing the survival rate of mouse infection-prevention test Experiment 2 of the modified gD in Example 9.

FIG. 35 presents a diagram showing the comparison results of multiple alignments of the amino acid sequence of gD derived from HSV-1 (SEQ ID NO: 2) and the amino acid sequence of gD derived from HSV-2 (SEQ ID NO: 3), with italics indicating the leader sequence and underlines indicating the amino acid residues at positions 50 to 54 of gD (P50-P54).

FIG. 36 presents, in panel (A), the neutralizing activity of anti-gD2 antibody No. 82 and, in panel (B), the plaque number-reducing activity of No. 82 antibody against HSV-1 (KOS).

DESCRIPTION OF EMBODIMENTS

Figure 1:
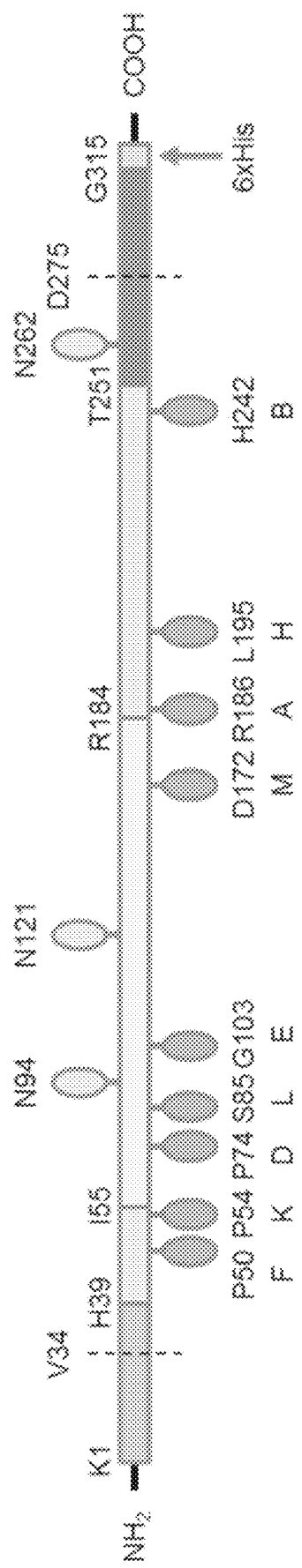
FIG. 1 presents a schematic diagram illustrating the primary structure of HSV gD.

Hereinafter, the embodiments for carrying out the present invention are described in detail below. However, the present invention is not limited to the following embodiments.

The modified HSV gD protein of the present invention is a modified protein of a herpes simplex virus (HSV) envelope glycoprotein D (gD), the modified HSV gD protein is derived from a wild-type HSV gD by modification of at least one of B cell epitopes having low or no neutralizing antibody-inducing activity compared to a B cell epitope present in a receptor-binding domain (RBD) (decotopes) in the ectodomain of the wild-type HSV gD, so that the modified epitope does not function as an epitope (de-epitope).

The present invention is based on the hypothesis proposed by the present inventors that there is a "decoy region" in the HSV gD antigen. The "decoy region" is derived from an English word "decoy" and is considered one of the immunoediting systems by which the pathogen escapes the host's immune response. The "decoy region" is an antigen region that induces antibodies having no or low neutralizing antibody activity, and is believed to be a mechanism by which pathogens escape the host's immune response such that the neutralizing antibodies are not produced or are produced in small amounts by the deceptive inprinting (also referred to as "immune deviation").

Until now, the presence of the decoy region has not been confirmed in HSV, not even the concept of the decoy region. The present inventors performed detailed epitope mapping analyses on anti-gD monoclonal antibodies obtained by comprehensive exploration of anti-HSV gD antibodies performed using a human antibody library. As the result, the presence of decoy regions in which unbeneficial or deleterious epitopes are concentrated was revealed by classifying B cell epitopes of HSV gD into unbeneficial or deleterious epitopes and beneficial epitopes capable of inducing neutralizing antibodies. Then, by de-epitoping unbeneficial or deleterious epitope in the decoy region and immunologically emphasizing the beneficial epitope, modified HSV gD proteins that are capable of inducing antibodies with high neutralizing activity have been finally obtained.

The "wild-type HSV gD" refers to the full length of HSV-1 derived envelope glycoprotein D (gD) having the amino acid sequence set forth in SEQ ID NO: 2, or HSV-2 derived gD having the amino acid sequence set forth in SEQ ID NO: 3 (GenBank Accession No.: ABU 45433.1). As the result of comparing the two sequences in multiple alignments, the sequence identity is 84% (FIG. 35). The conformation of gD has also been analyzed and, for example, in gD derived from HSV-1, it is known that it consists of a transmembrane domain having amino acid residues at positions 317 to 339, an intracellular domain having amino acid residues at positions 340 to 369, and the ectodomain having amino acid residue at positions 1 to 316. Single crystal structures of gD derived from HSV-1 are reported in Non Patent Literature 7, and co-crystal structures thereof are reported in Non Patent Literatures 2 and 6. The crystal structure of gD derived from HSV-2 has been reported in Non Patent Literatures 11 and 12. The "ectodomain of wild-type HSV gD" means a soluble, antigenic extracellular region of the wild-type HSV gD. An example of the ectodomain of the wild-type HSV gD is a wild-type gD ectodomain 1-315 derived from a 333 strain of HSV-2 consisting of the amino acid sequence set forth in SEQ ID NO: 1.

The "modified HSV gD protein" ("modified protein of HSV gD" or "variant") is a protein in which at least one amino acid residue or a region of contiguous amino acid residues is substituted, deleted or added to a wild-type HSV gD, and includes a protein in which a protein modification that is not present in the wild-type is performed, such as a protein in which a glycochain is introduced by substitution or deficiency of the amino acid residue.

The "neutralizing antibody-inducing activity" refers to the ability to induce neutralizing antibodies of an antigen protein. The "neutralizing antibody-inducing activity" can be evaluated by the neutralizing antibody titer in immune serum obtained by inoculating the antigen protein into a subject animal. The "neutralizing antibody" refers to an antibody that is capable of losing the infectivity of a viral particle. The "neutralizing antibody" is, for example, determined by the degree of neutralizing activity of the antibody at a concentration (NT50) necessary to reduce the plaque number of the subject virus by 50%.

A B cell epitope with high neutralizing antibody-inducing activity in the ectodomain of wild-type HSV gD is referred to as a "beneficial epitope". Examples of the beneficial epitopes in the ectodomain of wild-type HSV gD include B cell epitopes typically present in the receptor-binding domain (RBD). In particular, examples thereof include an epitope containing an amino acid residue corresponding to at least one amino acid residue selected from the group consisting of an arginine residue at position 134, an aspartic acid residue at position 139, and 222nd arginine residue in the amino acid sequence set forth in SEQ ID NO: 1.

The "decotope" refers to a B cell epitope having low or no neutralizing antibody-inducing activity compared to a B cell epitope present in RBD in the ectodomain of wild-type HSV gD. The "decotope" is classified herein as an "unbeneficial or deleterious epitope". It is preferred that the "decotope" is a B cell epitope having low or no neutralizing antibody-inducing activity compared to a B cell epitope containing an amino acid residue corresponding to at least one amino acid residue selected from the group consisting of an arginine residue at position 134, an aspartic acid residue at position 139, and 222nd arginine residue in the amino acid sequence set forth in SEQ ID NO: 1 in the ectodomain of wild-type HSV gD. Examples of the "decotope" in the ectodomain of wild-type HSV gD in the present embodiment include an epitope present in the N-terminal proline-rich region (PRR) of the gD ectodomain.

Figure 3:
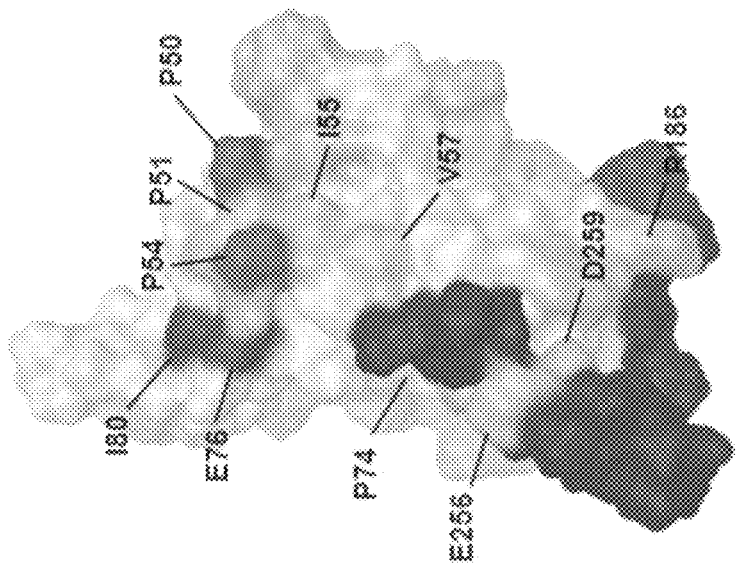
FIG. 3 presents diagrams illustrating a MOE diagram of the gD receptor binding domain (RBD) peripheral region (FIG. 3, panel (A)) and the P50 peripheral region (FIG. 3, panel (B)) in an HSV gD crystal structure.
Figure 3:
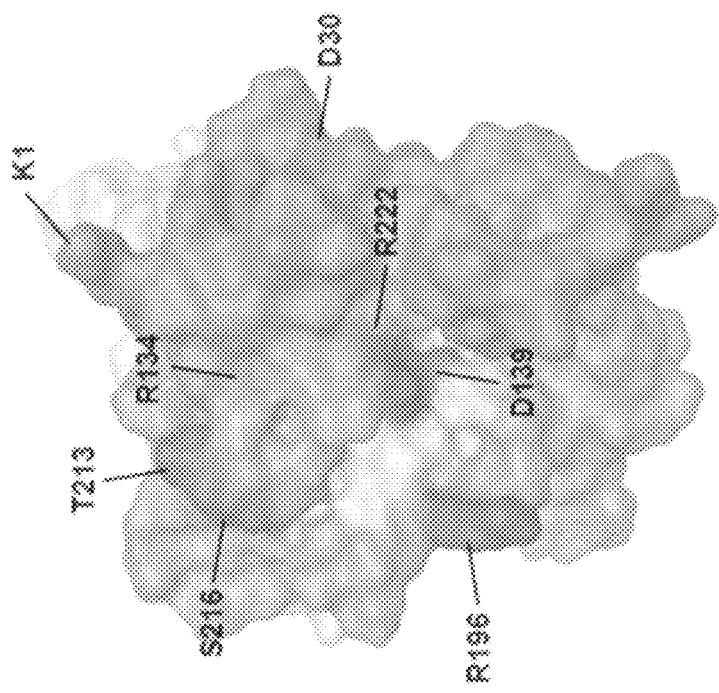

The area where decotopes concentrate is referred to as the "decoy region". According to a result of analysis by the present inventors, the PRR of HSV gD is one example of the decoy region. PRR is located on an opposite side to RBD in the crystal structure of the ectodomain of wild-type HSV gD (FIG. 3). The P50 peripheral region in PRR is a very typical decoy region. The "P50 peripheral region" refers to a region that has a distance of no more than 1.5 nm from an amino acid residue corresponding to a proline residue at position 50 in the wild-type gD ectodomain 1-315 derived from HSV-2 consisting of the amino acid sequence set forth in SEQ ID NO: 1 in the surface of the crystal structure of the wild-type HSV gD ectodomain. Here, the "distance from an amino acid residue" refers to the linear distance from an amino acid residue corresponding to the proline residue at position 50, regardless of the shape of the surface of the crystal structure of the wild-type HSV gD ectodomain.

An example of the decotope is an epitope comprising an amino acid residue corresponding to a proline residue at position 50 in the wild-type gD ectodomain 1-315 derived from HSV-2 consisting of the amino acid sequence set forth in SEQ ID NO: 1.

The "corresponding" amino acid residue herein means an amino acid residue of other related gD at a position corresponding to a predetermined amino acid residue set forth in SEQ ID NO: 1 in an aligned sequence when the amino acid sequence of the wild-type gD ectodomain derived from HSV-2 consisting of the amino acid sequence set forth in SEQ ID NO: 1 is multiplex aligned (multiple-sequence alignment) with the amino acid sequence of the other related gD.

Another example of the decotope is an epitope comprising at least one amino acid residue present on the surface of a crystal structure of the ectodomain of HSV gD in a region at a distance of no more than 1.5 nm from an amino acid corresponding to a proline residue at position 50 (i.e., P50 peripheral region) in the wild-type gD ectodomain 1-315 derived from HSV-2 consisting of the amino acid sequence set forth in SEQ ID NO: 1. The decotope can be identified from the crystal structure of wild-type HSV gD. It is preferred that the distance is 1 nm or less.

When the decotope is used for immune induction, depending on the de-epitoping of the decotope, the percentage of production of unbeneficial or deleterious antibodies can be reduced, and the percentage of production of neutralizing antibodies with high neutralizing activity can be increased by emphasizing beneficial epitopes.

The "de-epitoping" refers to a modification of a site contributed to antibody production as an epitope in the wild-type HSV gD so as not to function as an epitope. The "de-epitoping" is also referred to as epitope masking. Examples of the method of de-epitoping include a method of substituting an amino acid residue at the site of an epitope with another amino acid residue; a method of defecting (deleting) an amino acid residue at the site of an epitope; and a method of introducing a glycochain by substitution or deficiency of an amino acid residue at the site of an epitope. As the method of de-epitoping, the method of introducing a glycochain, in particular an N-type glycochain (N-glycoside-linked glycochain) is preferable. The method has advantages in that not only the portion where the glycochain is introduced, but also the decotopes in the periphery can be masked at the same time due to its bulkiness. Considering the size ratio to proteins such as antibodies or receptors that interact with gD, it is expected that the dot-to-dot interaction such that binding is formed in a very narrow range of about a few amino acids is less likely to occur. In the binding between gD and receptors, it is believed that a network of facet-to-facet interaction is formed such that a wide range of amino acids cooperate to form a binding. Introduction of a glycochain is believed to be an effective way of de-epitoping to hide peripheral residues extensively by its own bulkiness, and simultaneously to inhibit access of the binding partner. It is also reported that the glycochain is difficult to induce anti-glycochain antibodies (Non Patent Literature 10), thus it is believed that the likelihood of new immunogenicity due to modification can be reduced.

Introduction of a glycochain to an amino acid residue refers to an introduction of a glycochain to three contiguous amino acid residues including the position of the amino acid residue by deletion, substitution or addition of an amino acid at the position of the amino acid residue. Methods of introducing a glycochain are not particularly limited as long as a conventional method. For example, when an N-type glycochain is introduced, the amino acid sequence of the wild-type gD protein ectodomain (SEQ ID NO: 1) is used as a template, and the primer is designed such that the three contiguous amino acid sequences of the site of interest at which the N-type glycochain is introduced become N-X-S/T (X is any amino acid other than proline), then a mutation is introduced by PCR. The nucleic acid sequence of mutated gD protein of interest, or the nucleic acid sequence further linked to a tag such as 6×His as required, can be cloned into an appropriate vector, then expressed to acquire a gD variant. Then, an N-type glycochain is added to asparagine at the site of interest of the gD modified by a conventional method. Examples of the N-type glycochain include a GlcNAc-based high mannose type, a hybrid type, and a complex type.

It is preferred that the de-epitoping, i.e., the modification of the decotope includes a modification made by introducing a glycochain into at least one of amino acid residues corresponding to a proline residue at position 50, proline at position 74, and arginine at position 186 in the amino acid sequence set forth in SEQ ID NO: 1 of the ectodomain of the wild-type HSV gD. In particular, it is preferred that the ectodomain of the wild-type HSV gD consists of the amino acid sequence set forth in SEQ ID NO: 1; and the modification of the decotope includes at least one modification selected from the group consisting of: a modification by introducing a glycochain by substitution of a proline residue at position 50 with an asparagine residue and substitution of a proline residue at position 51 with an amino acid residue other than a proline residue in the amino acid sequence set forth in SEQ ID NO: 1; a modification by introducing a glycochain by substitution of a proline residue at position 74 with an asparagine residue and substitution of a glutamic acid residue at position 76 with a serine residue in the amino acid sequence set forth in SEQ ID NO: 1; and a modification by introducing a glycochain by substitution of an arginine residue at position 186 with an asparagine residue in the amino acid sequence set forth in SEQ ID NO: 1.

The modified HSV gD protein further contains deficiency of at least a portion of amino acid residues corresponding to amino acid residues at positions 251 to 315 in the amino acid sequence set forth in SEQ ID NO: 1 in the wild-type HSV gD. The amino acid residues corresponding to amino acid residues at positions 251 to 315 in the amino acid sequence set forth in SEQ ID NO: 1 form a C-terminal functional region 3 (FR3) in the ectodomain of the wild-type HSV gD. Deficiency of at least a portion of this moiety is also effective in inducing immune refocusing to beneficial epitopes. Reported crystal structure analysis of HSV gD1 (Non Patent Literature 7) suggests that FR3 and the N-terminal side sequence FR1 can bind to wrap around exactly the same surface of the core beta-sheet structure FR2 in the gD molecule. Since FR1 and FR3 interfere with each other, only one of them can bind to FR2. It has been presumed that on the viral envelope FR3 normally binds, but upon binding to the receptor, FR3 falls off, and the structure changes such that FR1 binds, and the receptor binding region is exposed. From the epitope analysis of neutralizing antibody No. 82 which the present inventors have independently obtained, it has been found that antibody No. 82 binds to a Nectin-1 binding region, has reduced reactivity with the FR1-deficient mutant (gD34-315), and inhibits binding of gD to HVEM or Nectin-1. That is, it is believed that defecting FR3 or inhibiting binding of FR3 to FR2 is effective in order to emphasize the epitope of antibody No. 82, i.e. RBD, and to induce immune refocusing on the region.

The deficiency of at least a portion of FR3 also includes a deletion of the full length of FR3 or a deletion of a contiguous or non-contiguous sequence of a portion of FR3, and substitution of some amino acid residues with other amino acid residues. A partial deficiency of FR3 is preferably a deletion of a portion corresponding to amino acid residues at positions 276 to 315 in the wild-type gD ectodomain 1-315 derived from HSV-2 consisting of the amino acid sequence set forth in SEQ ID NO: 1, and may be a deletion of all or a portion of amino acid residues at positions 276 to 315.

It is preferred that the modified HSV gD protein further comprises at least one promiscuous T cell epitope linked at a C-terminal of the ectodomain of the HSV gD. T cell epitopes are also present in the transmembrane region and the intracellular region, but given their use as a vaccine, the design of the secretory phenotype composed of the extracellular region is preferred. Thus, it is preferred to link the T cell epitopes in the transmembrane region or intracellular region because the T cell epitope that is not included in the extracellular region can be effectively utilized.

The present inventors have performed comprehensive exploration of the HLA Class II constrained promiscuous T cell epitope cluster for the full length including the intracellular domain of gD2. As a result, five cluster peptides DP1-DP5 described below were found. It is preferred that the promiscuous T cell epitope is a promiscuous T cell epitope consisting of the amino acid sequence set forth in SEQ ID NO: 4, SEQ ID NO: 5, SEQ ID NO: 6, SEQ ID NO: 7, or SEQ ID NO: 8. Among them, those that actually have promiscuous stimulation activity against both mouse and human T cells are three peptides DP2, DP3, and DP5. In particular, DP5, which consists of the amino acid sequence set forth in SEQ ID NO: 8, is preferred. It may be linked to multiple promiscuous T cell epitopes. Specifically, for example, the linking to a promiscuous T cell epitope may include a linking to two or more promiscuous T cell epitopes consisting of the amino acid sequence set forth in SEQ ID NO: 8 at the C-terminal of the ectodomain of the wild-type HSV gD.

TABLE 1

| Predicted Promiscuous T cell epitope cluster sequence in HSV gD | | | | |
|---|---|---|---|---|
| | Sequence | Amino acid sequence | Length | SEQ ID NO: |
| DP1 | gD2 35-49 | KRVYHIQPSLEDPFQ | 15 | 4 |
| DP2 | gD2 55-71 | ITVYYAVLERACRSVLL | 17 | 5 |
| DP3 | gD2 170-191 | INDWTEITQFILEHRARASCKY | 22 | 6 |
| DP4 | gD2 314-329 | PGLIIGALAGSTLAVL | 16 | 7 |
| DP5 | gD2 | IAFWVRRRADMAPKPLR | 17 | 8 |

In one embodiment, the HSV gD protein further contains substitution of an amino acid residue corresponding to a valine residue at position 231 with another amino acid residue in the wild-type gD ectodomain 1-315 derived from HSV-2 consisting of the amino acid sequence set forth in SEQ ID NO: 1, in particular a tryptophan residue. Since the V231W mutation has been suggested to inhibit binding of FR3 to FR2 (Non Patent Literature 9), the variant containing this further mutation is preferred from the viewpoint of inhibiting binding of FR3 to FR2. This mutation more emphasizes the B cell epitope present in the receptor binding domain and can increase the percentage of production of neutralizing antibodies upon immune induction.

The modified HSV gD protein of the present invention can be produced by genetic engineering methods. Production methods thereof are not particularly limited, but examples thereof include a production method including: using the cDNA of the wild-type gD protein (SEQ ID NO: 33) as a template; designing a primer to introduce the mutation of interest; obtaining a nucleic acid into which the mutation has been introduced by PCR; functionally linking the nucleic acid to an expression promoter, and optionally a tag; and introducing the resultant into an appropriate expression vector to express a modified HSV gD protein. Alternatively, the modified HSV gD protein by introducing a glycochain can be obtained as described above. Vectors and promoters are not particularly limited, but examples thereof include pCAG vectors and CAG promoters.

The produced modified HSV gD protein may be purified as needed. Purification methods are not particularly limited, but examples thereof include purifications with affinity chromatography column, gel filtration chromatography column, and ion exchange chromatography column.

HSV infections include infections by HSV-1 and HSV-2, and examples thereof include lip herpes, corneal herpes, genital herpes, systemic neonatal herpes, and stomatitis, skin diseases, encephalitis, meningitis and myelitis due to HSV.

The HSV vaccine of the present invention contains the modified HSV gD protein of the present invention.

Examples of the dosage form of the HSV vaccine of the present embodiment include, liquid, powder (lyophilized powder, dried powder), capsule, tablet, and frozen form.

The HSV vaccine of the present embodiment may contain a pharmaceutically acceptable carrier. As the carrier, carriers commonly used in vaccine production can be used without limitation, and specific examples thereof include saline, buffered saline, dextrose, water, glycerol, isotonic aqueous buffers, and combinations of these. The vaccine may further contain emulsifiers, preservatives (e.g., thimerosal), isotonic agents, pH adjusting agents, and the like.

It is also possible that the HSV vaccine of the present embodiment further contains an adjuvant to further enhance the immunogenicity. Examples of the adjuvant include aluminum adjuvants; oil-in-water emulsion adjuvants containing squalene (AS03, MF59, or the like), ligands of Toll-like receptors such as CpG and 3-O-deacylated-4'-monophosphoryl lipid A (MPL); saponin-based adjuvants; polymer-based adjuvants such as polyγ-glutamic acid; and polysaccharides such as chitosan and inulin.

The HSV vaccine of the present embodiment can be obtained by mixing a modified HSV gD protein of the present invention with a carrier, adjuvant, or the like, as needed. The adjuvant may be mixed when used.

Examples of the administration route of the HSV vaccine of the present embodiment include transdermal administration, sublingual administration, ophthalmic administration, intradermal administration, intramuscular administration, oral administration, enteral administration, nasal administration, intravenous administration, subcutaneous administration, intraperitoneal administration, and oral to pulmonary inhalation administration.

Examples of the administration method of the HSV vaccine of the present embodiment include a syringe, a transdermal patch, a microneedle, an implantable sustained-release device, a syringe with microneedle, a needleless device, and a spray.

EXAMPLES

Hereinafter, the present invention is described in detail by way of examples, but the present invention is not limited in any way to these examples.

Example 1 Acquisition of Anti-HSV gD Monoclonal Antibodies

<Acquisition of scFv-Phage>

To perform a comprehensive epitope analysis of HSV-2 gD (gD2), various antibodies that bind to various epitopes on gD2 were acquired by biopanning against gD2. A wild-type soluble ectodomain derived from 333 strain of HSV-2 having the amino acid sequence set forth in SEQ ID NO: 1, gD1-315 protein, was used as gD2. The gD1-315 protein was expressed in host cells and purified. An scFv-phage display library prepared using human VH and VL cDNA made from mRNA derived from human B cells was used as the library. The scFv-phage display library prepared using human VH and VL cDNA from mRNA derived from human B cells was screened to acquire scFv-phage having reactivity with HSV-2 gD.

<Phage ELISA>

After panning, isolated scFv-phages were expressed. *E. coli* TG1 strains with phagemid vectors in which each scFv gene was cloned were cultured in 2×YTCG medium (37° C.). After M13K07 helper phage was infected with moi=20, phage expression was performed in 2×YTCK medium (25° C.) overnight. The obtained scFv-phages were concentrated with 20%-PEG-2.5M sodium hydrochloride.

Reactivity of the expressed scFv-phages with gD1-315 was confirmed by phage ELISA. After 100 μL of gD2 (2 μg/mL PBS) was immobilized in a 96-well microtiter plate (Maxisorp Plate, NUNC) overnight at 4° C., each well was washed three times with PBS and blocked with 300 μL of 1% BSA/PBS for 1 hour at room temperature. Each well was washed 3 times with PBS-T (0.05% Tween/PBS). Then, 100 μL of scFv-phage diluted 10-fold with 1% BSA/PBS was added, and reacted at 37° C. for 1 hour. Each well was washed again with PBS-T, and HRP-labeled antibody (HRP-added anti-M13 antibody diluted with 1% BSA PBS: anti-M13/HRP/1% BSA PBS) was added and reacted at 37° C. for 1 hour. Each well was washed with PBS-T, then colored with enzyme substrate (TMB) at room temperature for 30 minutes. After the reaction was stopped with 1N sulfuric acid, absorbance (color value) of 450 nm/650 nm was measured.

When the reactivity of scFv-phage to gD1-315 per clone was analyzed, 101 clones in the collected 188 clones showed specific binding to antigen. The VH and VL chain gene sequences for these 101 clones were further analyzed to acquire seven clones of unique sequences.

<Manufacture of scFv-hFc>

ScFv-hFc was manufactured based on the acquired seven scFv-phages. The variable region of the isolated scFv gene was linked to human Fc gene, then cloned into a pCAG vector to construct a scFv-hFc expression plasmid. Each expression plasmid was expressed using an Expi293 expression system (Life Technologies). After 4-6 days of culture, the supernatant was purified with Protein A affinity chromatography column (HiTrap Protein A HP Columns, GE Healthcare) and dialyzed with PBS. The purity was confirmed by size exclusion chromatography (Superdex 200 5/150 GL, GE Healthcare) and SDS-PAGE.

<Competition Inhibition Test Using Nectin-1>

For the manufactured scFv-hFc, a competition inhibition test was performed using Nectin-1, a receptor of gD.

The competition inhibition test was performed by the following competitive ELISA. 100 μL of gD2 (2 μg/mL PBS) was immobilized in a 96-well microtiter plate (Maxisorp Plate, NUNC) over 2 hours at room temperature. Each well was then washed three times with PBS and blocked with 300 μL of 1% BSA PBS for 1 hour at room temperature. Each well was washed 5 times with PBS-T (0.05% Tween PBS). 20 μg/mL scFv-hFc was diluted at any dilution fold with 1% BSA PBS, then 100 μL of the diluted scFv-hFc was added to the well, and reacted at 37° C. for 1 hour. Each well was washed again with PBS-T. scFv-phage or Nectin-1 (Recombinant Human Nectin-1 Protein, R&D Systems, Inc.) was diluted at any dilution fold with 1% BSA PBS, then 100 μL of the diluent was added to the well, and reacted at 37° C. for 1 hour. Each well was washed again with PBS-T. Then, HRP-labeled antibody (anti-M13/HRP/1% BSA PBS or HRP-added anti-His-tag antibody diluted with 1% BSA PBS: anti-His-tag/HRP/1% BSA PBS) was added and reacted at 37° C. for 1 hour. Each well was washed with PBS-T, then colored with TMB at room temperature for 30 minutes. After the reaction was stopped with 1N sulfuric acid, absorbance (OD value) of 450 nm/650 nm was measured. When a 50% or greater reduction in OD values was shown compared to OD values under the absence of scFv-hFc, they were considered to be competitive.

<Results>

The results are shown in Table 2. The seven scFv-phages were classified into three groups according to the pattern of competition. Antibody No. 82 belonging to Group A strongly competed with Nectin-1, suggesting the presence of an epitope in a Nectin-1 binding region. Only antibody No. 1 belonged to Group B and did not compete with other antibodies and receptor Nectin-1. Group C consisted of the remaining 5 clones (No. 5, No. 13, No. 72, No. 75, No. 78) and the clones competed with each other while not competing with the receptor Nectin-1.

TABLE 2

Seven anti-HSV-2 gD antibodies

| Group | Antibody No. | Family VH | Family VL |
|---|---|---|---|
| A | 82 | 1 | κ3 |
| B | 1 | 7 | κ1 |
| C | 5 | 4 | κ1 |
|   | 13 | 1 | κ4 |
|   | 72 | 1 | κ1 |
|   | 75 | 3 | κ1 |
|   | 78 | 3 | κ3 |

The DNA nucleotide sequences of the VH and VL chain genes of each scFv gene were determined with Big Dye Terminator v3.1 Cycle Sequencing Kit (Applied Biosystems). As the result, antibody No. 82 has heavy chains CDR1 to CDR3 consisting of the amino acid sequences set forth in SEQ ID NOs: 9-11 and light chains CDR1 to CDR3 consisting of the amino acid sequences set forth in SEQ ID NOs: 12-14.

```
Heavy chain CDR1:
GYAIN                       (SEQ ID NO: 9)

Heavy chain CDR2:
GIMPIFGTSNYAQKFQ            (SEQ ID NO: 10)

Heavy chain CDR3:
DWGAPLEKGAGSPFDV            (SEQ ID NO: 11)

Light chain CDR1:
RASQSVSSSYLA                (SEQ ID NO: 12)

Light chain CDR2:
GASSRAT                     (SEQ ID NO: 13)

Light chain CDR3:
QQYGSSPRS                   (SEQ ID NO: 14)
```

Example 2 Epitope Mapping of Anti-gD2 Binding Antibodies

<Epitope Analysis by Denaturation>

Western blotting with denatured gD1-315 was performed to analyze whether the epitope of each antibody was a conformational epitope or a linear epitope.

Western Blotting was performed as follows. 500 ng of denatured or non-denatured gD1-315 was loaded to 8-16% SDS-PAGE and electrophoresed. The denatured gD1-315 was obtained by adding 2% 2-mercaptoethanol to gD1-315 and boiling the mixture at 96° C. for 5 minutes. The non-denatured gD1-315 did not undergo these procedures and was directly loaded. After completion of the electrophoresis, the gel was transferred to a nitrocellulose membrane (Immobilon-P, Millipore) and blocked with 2% fat-free milk-PBS-T. After washed with PBS-T, the membrane was reacted with each scFv-hFc at a concentration of 1 μg/mL 2% fat-free milk-PBS-T at room temperature for 30 minutes. After washed again, the membrane was reacted with anti-hFc/HRP/2% fat-free milk-PBS-T, and colored with Immobilon Western Detection Regent (Millipore).

As the result, antibodies that showed reactivity with gD1-315 denatured by a denaturing agent and heat shock were two antibodies No. 1 and No. 13, suggesting that epitopes of these are linear. All other antibodies showed reactivity only with non-denatured gD1-315, suggesting that epitopes of these are conformational.

<Epitope Mapping of Antibodies Using gD Variant by Introduction of Glycochain>

Epitope masking methods using gD variant by introduction of N-linked glycochains were investigated. The selection of introduction sites of glycochain was based on crystal structures already reported (Non Patent Literatures 1, 2, and 6) and was directed to loop sites that were exposed to the surface of the crystal structure and did not take a secondary structure. FIG. 1 shows a schematic diagram of the primary structure of gD, showing FR1 (K1-H39), FR2 (I55-R184), and FR3 (T251-G315), respectively. The glycochains originally attached to gD bind at N94, N121 and N262. Nine sites P50 (SC-F), P54 (SC-K), P74 (SC-D), S85 (SC-L), G103 (SC-E), D172 (SC-M), R186 (SC-A), L195 (SC-H) and H242 (SC-B) were selected as introduction sites of glycochains.

In constructing the expression plasmid of the gD variant, the cDNA of the wild-type gD protein (SEQ ID NO: 33) derived from HSV-2 333 strain was used as a template. Since the N-linked glycochains bind to asparagine of N-X-S/T (X is any amino acid other than proline), upon introducing of a glycochain, mutations were performed by PCR using the following primers such that the amino acid sequence at the site of interest would be NXT or NXS (X is any amino acid other than proline). Fw represents Forward, Re represents Reverse. The underline indicates the mutated part. DNA designed to be a signal sequence followed by the nucleic acid sequence of the mutated gD protein of interest, and further the nucleic acid sequence of 6×His were genetically synthesized and cloned into a pUC19 vector.

```
                            (SEQ ID NO: 15)
SC-A-Fw:    5'-CGGGCCAATGCCTCCTGCAAGTACGCT-3'

(SEQ ID NO: 16)
SC-A-Re:    5'-GGAGGCATTGGCCCGGTGCTCCAGGAT-3'

(SEQ ID NO: 17)
SC-B-Fw:    5'-GGGTGGAATGGCACCAAGCCCCCGTACACCAGC-3'

(SEQ ID NO: 18)
SC-B-Re:    5'-GGGCTTGGTGCCATTCCACCCGGCGATTTTTAA-3'

(SEQ ID NO: 19)
SC-D-Fw:    5'-CATGCCAATTCGACCGCCCCCCAGATCGTGCGC-3'

(SEQ ID NO: 20)
SC-D-Re:    5'-GGGGGCGGTCGAATTGGCATGTAGGAGCACGCT-3'

(SEQ ID NO: 21)
SC-E-Fw:    5'-CGCATGAATGACACCTGCGCTATCCCCATCACG-3'

(SEQ ID NO: 22)
SC-E-Re:    5'-AGCGCAGGTGTCATTCATGCGATACCAGGCGAT-3'

(SEQ ID NO: 23)
SC-F-Fw:    5'-TTCCAGAATGCAAGCATCCCGATCACTGTGTAC-3'

(SEQ ID NO: 24)
SC-F-Re:    5'-CGGGATGCTTGCATTCTGGAACGGGTCCTCCAG-3'

(SEQ ID NO: 25)
SC-H-Fw:    5'-CTCCCCAATCGCACGCCCCCGGCAGCGTGCCTC-3'

(SEQ ID NO: 26)
SC-H-Re:    5'-CGGGGGCGTGCGATTGGGGAGAGCGTACTTGCA-3'

(SEQ ID NO: 27)
SC-K-Fw:    5'-AGCATCAATATCACTGTGTACTACGCA-3'

(SEQ ID NO: 28)
SC-K-Re:    5'-AGTGATATTGATGCTGGGGGGCTGGAA-3'

(SEQ ID NO: 29)
SC-L-Fw:    5'-GGGGCTAATGACACCGCCCGAAAGCACACGTAC-3'

(SEQ ID NO: 30)
SC-L-Re:    5'-TCGGGCGGTGTCATTAGCCCCGCGCACGATCTG-3'

(SEQ ID NO: 31)
SC-M-Fw:    5'-ATAAACAATTGGACGGAGATCACACAA-3'

(SEQ ID NO: 32)
SC-M-Re:    5'-CGTCCAATTGTTTATCTTCACTAGCCG-3'
```

The completed sequence of the variant was cloned into a pCAGGS1-dhfr-neo vector to acquire a plasmid for expression. Each plasmid for expression was expressed using an Expi293 expression system. After 4-6 days of culture, the supernatant was purified with a Ni-NTA affinity chromatography column (TALON Superflow Metal Affinity Resin, Takara Bio Inc.) and dialyzed with PBS. The purity was confirmed by size exclusion chromatography and SDS-PAGE.

Reactivity analysis of each antibody against these glycochain introduced mutants was performed with competitive ELISA. 100 µL of gD variant (2 µg/mL PBS) was immobilized in a 96-well microtiter plate (Maxisorp Plate, NUNC) overnight at 4° C. Each well was washed three times with PBS and blocked with 300 µL of 1% BSA PBS for 1 hour at room temperature. Each well was washed 3 times with PBS-T (0.05% Tween PBS). Each scFv-hFc was diluted at any dilution fold with 1% BSA PBS, then 100 µL of the diluted scFv-hFc was added to the well, and reacted at 37° C. for 1 hour. Each well was washed again with PBS-T. Then, HRP-labeled antibody (HRP-added anti-hFc antibody diluted with 1% BSA PBS: anti-hFc/HRP/1% BSA PBS) was added and reacted at 37° C. for 1 hour. Each well was washed with PBS-T, then colored with TMB at room temperature for 30 minutes. After the reaction was stopped with 1N sulfuric acid, absorbance (OD value) of 450 nm/650 nm was measured. Compared to absorbance of wild-type gD1-315, absorbance of less than 30% was considered as inhibition (−), 30% or more and less than 70% was considered as partial inhibition (±), and 70% or more was considered as no inhibition (+). The results are shown in Table 3.

<Epitope Mapping of Antibodies Using gD Variant by Deficiency>

Three deficiency variants, gD1-275, gD25-253 and gD34-315, were manufactured by total synthesis (FIG. 1).

Reactivity analysis of these deficiency variants with each antibody was performed using competitive ELISA similarly as described above. The results are shown in Table 3.

TABLE 3

Reactivity of anti-gD2 antibodies against various gD mutants

| Group | Antibody No. | Western Blotting | Glycochain introduced gD mutant | | | | | | | | | Deficient gD mutant | | |
|---|---|---|---|---|---|---|---|---|---|---|---|---|---|---|
| | | | A | D | E | H | L | M | B | F | K | gD1-275 | gD25-253 | gD34-315 |
| A | 82 | C | + | + | + | + | + | + | ± | + | + | + | + | ± |
| B | 1 | L | + | + | + | + | + | + | + | + | + | − | − | + |
| C | 5 | C | + | + | + | + | + | + | + | − | − | + | + | + |
| | 13 | L | + | + | + | + | + | + | + | + | + | + | + | + |
| | 72 | C | + | + | + | + | + | + | + | − | − | + | ± | ± |
| | 75 | C | + | + | + | + | + | + | ± | − | − | + | − | + |
| | 78 | C | + | + | + | + | + | + | + | − | − | + | + | + |

L: Linear epitope
C: Conformational epitope
[OD values compared to absorbance of wild-type gD1-315] (−): less than 30%, (±): 30% or more and less than 70%, (+): 70% or more From the results of Table 3, with gD1-315 in which glycochains were introduced into P50 (SC-F) and P54 (SC-K), reactivity with antibodies No. 5, No. 72, No. 75 and No. 78 classified into the same group in the competition inhibition test was completely inhibited. For H242 (SC-B), the reaction with No. 75 and No. 82 was partially inhibited. H242 (SC-B) is thought to be a site where antibody No. 82 is structurally inaccessible directly, but since the site is in the vicinity in the amino acid sequence, it is presumed that the reaction was affected by structural changes. Furthermore, since the introduction site of H242 (SC-B) was far away from P50 (SC-F), it was also presumed that the decrease in the reactivity of antibody No. 75 was due to some indirect effect. Meanwhile, there were no effects on the binding of each antibody due to introduction of glycochains into SC-A, D, E, H, L, M.

For the deficient mutants, the reactivity of C-terminal (FR3)-deficient mutants gD1-275 and gD25-253 with antibody No. 1 was eliminated. Since it was suggested from the previous analysis that antibody NO. 1 has a linear epitope, it was believed that there was an epitope of antibody NO. 1 in 275-315.

Furthermore, regarding antibodies No. 72 and No. 75 which showed no change in reactivity with gD1-275, antibody No. 72 reduced the reactivity and antibody No. 75 eliminated the reaction when gD25-253 was used. This suggests that at least a portion of the epitopes of antibody No. 72 and antibody No. 75 is present in gD254-275. In the crystal structure, gD254-275 is present in the vicinity of P50 (SC-F), thus it is also contemplated that these antibodies may recognize both of them. In particular, antibody No. 75 which reduced reactivity also in H242 (SC-B) is presumed to be possibly heavily influenced by H242 (SC-B) present in the vicinity of FR3 due to its high binding dependency on the epitope in gD254-275.

The reactivity with antibody No. 72 was also reduced when gD34-315, an N-terminal (FR1)-deficient mutant, was used. However, from the previous analysis, it was difficult to believe in structure that the epitope of antibody No. 72 was present in FR1, thus it was thought that the effect on FR3 due to FR1 deficiency should be considered. Crystal structure analysis suggests that FR1 and FR3 may bind to wrap around the same surface of the core beta-sheet structure FR2 of gD (Non Patent Literature 6). Since FR1 and FR3 interfere with each other, only one of them can bind to FR2. Since gD254-275 is a flexible region at the "root" of FR3, it is inferred that the strength of binding of antibodies No. 72 and No. 75 changes depending on the whole structure of FR3. That is, it is believed that FR3 binds to FR2 in the FR1-deficient mutant gD34-315, then the epitope near P50 (SC-F) is away from the epitope in gD254-275, leading to reduction of the reactivity. Antibody No. 75 should have been affected similarly by the epitope near P50 (SC-F) being away from the epitope in gD254-275 in the same way. However, it is inferred that antibody No. 75 was less susceptible to this influence because antibody No. 75 strongly binds to gD254-275.

It was also found that the reactivity with antibody No. 82 was also reduced when an N-terminal (FR1)-deficient mutant gD34-315 was used. From this, it was believed that there are possibilities that an epitope of antibody No. 82 is present in 1-33 amino acids and that binding of FR3 to FR2 inhibits access of antibody No. 82. Furthermore, no reduction in reactivity was found when gD25-253 was used, thus it is also reasonable to assume that an epitope of antibody No. 82 is present in 25-33.

[Alanine Scanning with Alanine Substitutes]

Based on the information obtained above, using alanine substitutes, the receptor binding domain (RBD) that is a Nectin-1 binding region, and the peripheral region of P50 (SC-F), where the presence of an epitope of antibody No. 82 was predicted, were alanine scanned. The amino acids which were believed to be structurally exposed to the surface were mainly selected, then fourteen mutants in which amino acids are substituted with alanine, and blocking mutants of the neutralizing antibody LP2, T213M and S216N, were manufactured. The each of genes having alanine substitution were constructed by PCR and cloned into pCAGGS1-dhfr-neo. For expression, a FreeStyle 293 or Expi293 expression system was used.

Figure 2:
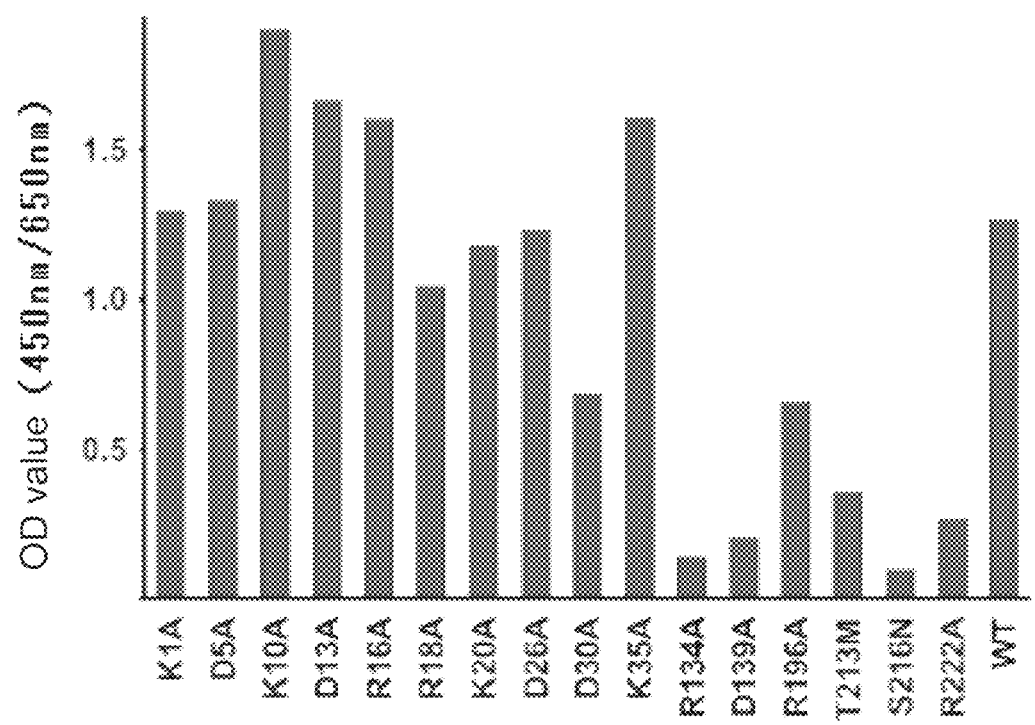
FIG. 2 presents a graph showing the result of analysis of the reactivity of anti-gD2 antibody No. 82 with an alanine substituted gD variant in competitive ELISA in Example 2.

The reactivity of antibody No. 82 with alanine substituted gD variants was analyzed with competitive ELISA. The results are shown in FIG. 2. In the reactivity analysis of antibody No. 82, reactivities of five mutants R134A, D139A, T213M, S216N and R222A were significantly reduced and the reactivity of R196A was reduced. It has been reported that all of these amino acids are very proximal amino acids in the same interface, and, in particular, S216 and R222 are the binding sites of Nectin-1. From this, it was suggested again that antibody No. 82 binds to the Nectin-1 binding region.

On the other hand, in the alanine substitutes of FR1, D30A showed reduced reactivity. D30 is believed to be a portion of an epitope present in 25-33 amino acids. However, in the peripheries of R222 and D30, when FR1 binds to FR2, it is not possible to be present in the same interface because FR1 becomes a hindrance. Thus, when antibody No. 82 binds, it is believed that the reaction proceeds with unbinding of FR1 and FR2.

Furthermore, for antibodies other than antibody No. 82, a tendency generally consistent with the results of the reactivity of the various anti-gD2 antibodies with the various gD mutants shown in Table 3 was found in the reactivity analysis using SC-F peripheral alanine substitutes. The reactivity with antibody No. 78 was reduced in P51A and I55A. The reactivity with antibody No. 72 was reduced in V57A and E256A, and the reactivity with antibody No. 75 was reduced in I55A and D259A in addition to V57A and E256A. The SC-F and all of these residues are located in the vicinity in the same interface, thus the result became a support of the hypothesis that a portion of the epitopes in particular of antibody No. 72 and antibody No. 75 are present in 254-275. For antibody No. 5, the alanine substitutes that have reduced reactivity with antibody No. 5 were three substitutes I55, E76, and I80, and the binding regions were scattered in different directions about 120° from the binding regions of antibodies No. 72, No. 75 and No. 78 with I55 as the center. The epitopes of antibody No. 13 were not determined. This is presumably because the epitopes of antibody No. 13 are suggested to be linear, thus have not been able to mutate directly in the mutants obtained so far.

As the result of epitope mapping, epitopes of seven antibody clones are estimated as shown in Table 4. FIG. 3 shows a MOE diagram of the gD receptor binding domain (RBD) peripheral region and the P50 peripheral region in an HSV gD structure. In FIG. 3, the epitopes of antibody No. 82 (R134, D139, and R222) can be confirmed to be present in the RBD region.

TABLE 4

Presumed epitope regions of various anti-gD2 antibodies

| Group | Antibody No. | Epitope region |
|---|---|---|
| A | 82 | RBD (+FR1) |
| B | 1 | FR3 |
| C1 | 5 | P50 periphery + α |
| | 13 | Unknown |
| C2 | 72 | P50 periphery (+FR3) |
| | 75 | P50 periphery + FR3 |
| | 78 | P50 periphery |

Example 3 Neutralizing Activity of Anti-gD2 Antibodies

HSV neutralizing activity analysis of seven antibody clones in vitro was performed in a plaque number reduction (plaque reduction) test and a cell-to-cell infection spread-suppression test.

<Culture of Cells and Viruses>

Two types of virus of interest, Human herpes virus 2 (HSV-2) MS strain (VR-540) and Human herpes virus 1 (HSV-1) KOS strain (VR-1493), purchased from ATCC, were used. Vero cells purchased from ATCC (CCL.81) were used for viral culture, measurement of infectivity titer, and measurement of neutralizing antibody titer. Vero cells are cultured at 37° C. under 5% $CO_2$ conditions. 10% FBS-containing MEM medium was used for proliferation, maintenance, and analysis plate preparation, and 2% FBS-containing MEM medium was used for measurement of infectivity titer and measurement of neutralizing antibody titer. Viral banks for neutralization test and infection prevention ability analysis described below were prepared by the following methods. HSV-2 MS strain and HSV-1 KOS strain were inoculated into full-sheeted Vero cells at m.o.i=0.01-1 and cultured in 2% FBS-containing MEM medium for 2-3 days. After crushing cells by lyophilizing and thawing three times the bottle containing the collected infected cell culture, the cells were centrifuged at 3500 rpm at room temperature with a TOMY centrifuge for 10 minutes, and the supernatant was used as HSV-2 virus bank and HSV-1 virus bank.

<Neutralization Test>

(Plaque Number Reduction Test)

For measurements of plaque reduction activity, a predetermined concentration of the subject antibody was prepared and mixed with approximately 100 PFU of an HSV-2 MS strain or an HSV-1 KOS strain, then reacted at 37° C. for 1 hour. The reaction solution was plated to Vero cells full-sheeted in a 48-well plate, and after adsorption at 30° C. for 1 hour, cultured in 1% methylcellulose-containing MEM (2% FBS) medium for 24 hours, then inactivated and immobilized at −20° C. for 30 minutes with 50% methanol/50% ethanol (−20° C.) obtained by mixing methanol and ethanol at 1:1. The anti-HSV gD monoclonal antibody was then reacted at 37° C. for 1 hour, the resultant was immunostained with anti-mouse IgG-HRP (DakoP0447) and TMBH, and images of each well were captured with an ELISpot analyzer (Immunospot S6 Analyzer, CTL) to count plaque numbers with analytical software (BioSpot, CTL).

(Cell-to-Cell Infection Spread-Suppression Test)

For measurement of cell-to-cell infection spread-suppression activity, approximately 100 PFU of HSV-2 MS strain or HSV-1 KOS strain were inoculated into Vero cells full-sheeted in a 48-well plate and adsorption was performed at 30° C. for 1 hour. Thereafter, a predetermined concentration of the subject antibody in 1% methylcellulose-containing MEM (2% FBS) medium (antibody concentrations 5 μg/mL, 25 μg/mL, and 125 μg/mL) was added, and the HSV-2 MS strain was cultured for about 40 hours and the HSV-1 KOS strain was cultured for about 48 hours before inactivated and immobilized at −20° C. for 30 minutes with 50% methanol/50% ethanol (−20° C.). Self-prepared anti-HSV gD monoclonal antibodies were then reacted at 37° C. for 1 hour, the resulting cells were immunostained with anti-mouse IgG-HRP and TMBH, and images of each well were captured with an ELISpot analyzer to analyze average plaque size values with an analytical software.

<Results>

The experimental results are shown in Table 5. For plaque number-reducing activity, final concentrations of each antibody were set to 50 μg/mL, 10 μg/mL, and 2 μg/mL for MS strains (HSV-2) and KOS strains (HSV-1) each, and measurements at each concentration were performed by detection of 2 wells to take an average value. As the result, antibody No. 82, classified into Group A and having an epitope region in the gD receptor binding domain (RBD) (and in FR1), showed the most significant plaque number-reducing activity against both HSV-1 and HSV-2 strains. In contrast, antibody No. 1, classified into Group B and having an epitope region in FR3, showed no plaque number-reducing activity against either strains. Both antibodies No. 5 and antibody No. 13, which are classified into Group C1 and having epitope regions around P50 periphery or other unknown moieties, showed relatively weak neutralizing activities against HSV-1 and HSV-2 and exhibited a pattern of partial inhibition against HSV-1. Here, the "partial inhibition" refers to an inhibition where neutralizing activity is relatively weak and no dose-dependent reduction is clearly confirmed. Furthermore, both antibodies No. 72 and No. 75, which are classified into Group C2 and having an epitope region around P50 periphery (and FR3), had significantly weaker neutralizing activity against HSV-2 than HSV-1, and antibody No. 72 exhibited a pattern of partial inhibition against HSV-2. Further, antibody No. 78, also classified into Group C2, showed no significant biased neutralizing activities for both strains, but the intensity thereof was inferior to that of antibody No. 82. Antibody No. 78 inhibited dosedependently, but the pattern of the tilt of inhibitory effect thereof against the tilt of 5-fold serial dilution was mild compared to that of others.

For cell-to-cell infection spread-suppression activity, the final concentration of each antibody was set to 20 μg/mL for the MS strain (HSV-2) and examined in duplicate. As the result, the only antibody No. 82 showed definite inhibitory activity, while the other 6 antibodies did not show definite activity. This activity is considered to be an important activity that may lead to a suppression effect on the spread of infection, or even a suppression effect on recurrent symptoms, in therapeutic administration under situations where a viral infection is already established in vivo.

From the above, it is believed that antibody No. 82 is a unique antibody with superior characteristics that are fundamentally different from other anti-gD-binding antibodies in that it has not only potent plaque number-reducing activity against both HSV-1 and HSV-2 strains, but also cell-to-cell infection spread-suppression activity that may lead to therapeutic effects, and it is believed that the superiority of which is associated with the presence of an epitope region on the gD receptor binding domain (RBD).

TABLE 5

HSV neutralizing activity of anti-gD antibodies

| Group | Antibody No. | Epitope region | Strain | Plaque number-reducing activity 50 μg/mL | 10 μg/mL | 2 μg/mL | Partial inhibition (P) | Cell-to-cell infection spread-suppression activity (MS strain) 20 μg/mL |
|---|---|---|---|---|---|---|---|---|
| A | 82 | RBD (+FR1) | MS | +++ | +++ | +++ | | ++ |
|   |    |            | KOS | +++ | +++ | +++ | | |
| B | 1 | FR3 | MS | − | − | − | | − |
|   |   |     | KOS | − | − | − | | |
| C1 | 5 | P50 periphery + α | MS | +++ | + | − | | − |
|    |   |                    | KOS | + | − | − | P | |
|    | 13 | unknown | MS | +++ | ++ | − | | − |
|    |    |          | KOS | + | + | − | P | |
| C2 | 72 | P50 periphery (+FR3) | MS | + | + | + | P | − |
|    |    |                       | KOS | +++ | +++ | +++ | | |
|    | 75 | P50 periphery + FR3 | MS | +++ | + | − | | − |
|    |    |                      | KOS | +++ | +++ | +++ | | |
|    | 78 | P50 periphery | MS | +++ | +++ | + | | − |
|    |    |                | KOS | +++ | ++ | + | (P) | |

[Plaque number-reducing activity intensity classification]
+++: n <= 5%/++: 5% < n <= 10%/+: 10% < n <= 50%/−: 50% < n
(n is a percentage when plaque number of negative control well is 100)
[Cell-to-cell infection spread-suppression activity intensity classification] ++: Presence of definite activity/−: Absence of definite activity Example 4 Detailed Analysis of Viral Neutralizing Activity of Anti-gD2 Antibody No. 82

In addition to the human antibody scFv-hFc of anti-gD2 antibody No. 82, a human-mouse chimeric IgG with a mouse Fc region and a human-guinea pig chimeric IgG with a guinea pig Fc region were prepared, and each neutralizing activity (plaque number-reducing activity) was investigated for HSV-2 (MS strain) and HSV-1 (KOS strain).

<Human-Mouse Chimeric IgG2a>

The VH region of the isolated scFv gene was linked to the H chain constant region gene (CH1-CH2-CH3) derived from mouse IgG2a, then cloned into a pCAG vector to construct a H-chain expression plasmid. Furthermore, the VL region of the scFv gene was linked to mouse CL gene, then cloned into a pCAG vector to construct an L-chain expression plasmid. An Expi293 expression system was employed for expression. Expression plasmids were transfected into cells and culture supernatants were collected at 4-6 days. Culture supernatants were purified with Hi Trap Protein A HP Column (GE Healthcare) and dialyzed with PBS. The purity was confirmed by size exclusion chromatography and SDS-PAGE. Human-mouse chimeric IgG2a was acquired by the above methods.

<Human-Guinea Pig Chimeric IgG2κ>

The VH region of the isolated scFv gene was linked to a H-chain constant region gene derived from guinea pig IgG2 (CH1-CH2-CH3), and cloned into the pCAG vector. Similarly, the VL region of the scFv gene was linked to guinea pig CK gene, and cloned into the pCAG vector. The cloned antibody genes were then amplified by PCR, cloned into a pXC vector (Lonza) to construct expression plasmids for H and L chains. Both plasmids were then linked to prepare one expression plasmid. CHO cells were used for expression. Expression plasmids were stably introduced into CHO cells and antibody high-expression CHO cells were obtained using GS Xceed expression system (Lonza). High-expression cells were fed-batch cultured for 12 days and the culture supernatant was collected. The culture supernatants were purified using rProtein A sepharose Fast Flow (Cat #17127903/GE Healthcare) to afford a human-guinea pig chimeric IgG2K antibody.

<Results>

The scFv-hFc, human-mouse chimeric IgG, and human-guinea pig chimeric IgG of anti-gD2 antibody No. 82 were analyzed for viral neutralizing activity (plaque number-reducing activity) as described in Example 4. The results are shown in FIG. 36. Any of the scFv-hFc, human-mouse chimeric IgG, and human-guinea pig chimeric IgG of antibody No. 82 exhibited 50% plaque number-reducing activity at concentrations of 0.05 μg/mL or more against both MS (HSV-2) and KOS (HSV-1) strains.

Example 5 Evaluation of Mouse Infection Prevention Ability of Anti-gD2 Antibody No. 82

The mouse genital herpes infection model was used to evaluate the infection prevention ability in the preventive and therapeutic administration of anti-gD2 antibody No. 82.

<Mouse Infection-Prevention Test>

An infection-prevention test was performed in the preventive and therapeutic administration of anti-HSV gD2 monoclonal antibodies using a mouse genital herpes infection model. BALB/c mice (5 weeks old, female) were used. A predetermined amount of the antibody was dissolved in saline for injection and administered intraperitoneally at a dose of 200 μL/mouse 24 hours prior to viral inoculation for preventive administration and 48 hours after viral inoculation for therapeutic administration. The number of N=10 cases per group was set. To improve the multiplicity of infection upon viral inoculation, Depo-Provera was inoculated subcutaneously at 2 mg/mouse 6 days prior to viral inoculation. $5 \times 10^5$ PFU/20 μL HSV-2 MS strain was inoculated transvaginally under anesthesia and observed for 21 days. The infection prevention ability was evaluated using survival time (survival rate) and symptom score as indexes. Symptom scores were determined by the presence or absence and the extent of vaginal lesion symptoms, and shown as an average value in each group. Scoring was set as 0: no change, 1: partial erythema/swelling, 2: extensive swelling/edema, 3: ulceration/bleeding, 4: death. If serious systemic symptom (hair loss, paralysis, shock, convulsions, or the like) with no prospect of recovery was observed, the score on that day was determined as 3.5 and the mouse was sacrificed, then the following day, the mouse was treated as death and the score was determined as 4.

<Results>

Figure 4:
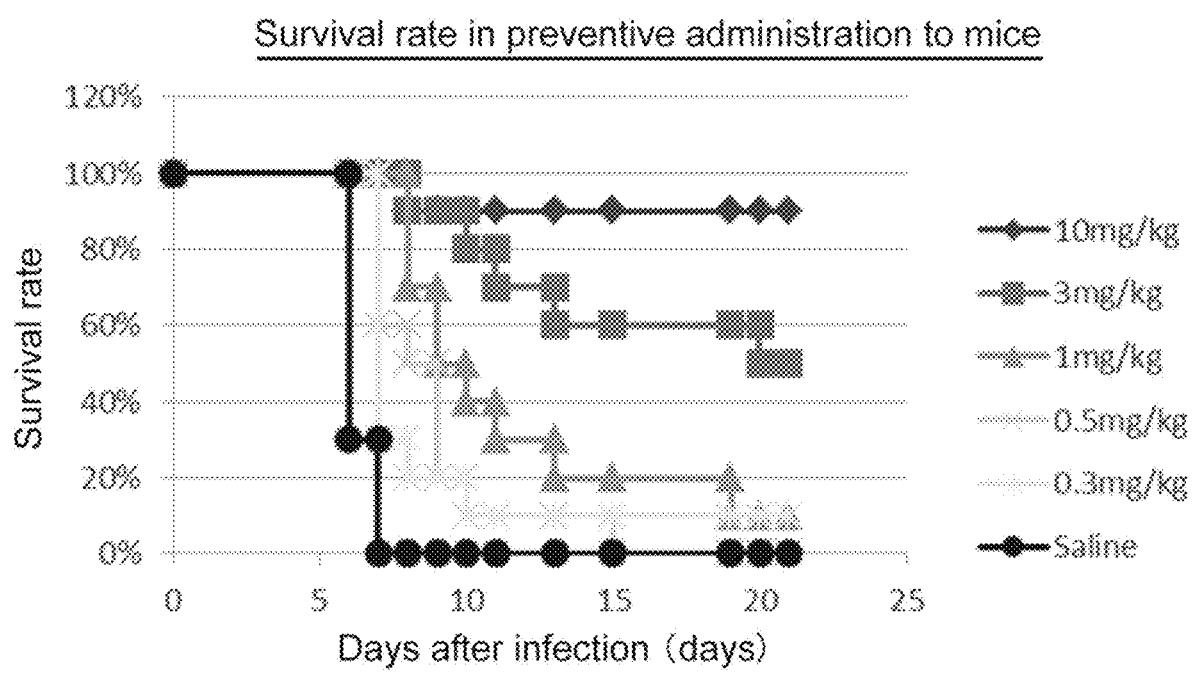
FIG. 4 presents a diagram showing survival rate after preventive administration of the anti-gD antibody to mice in Example 5.
Figure 5:
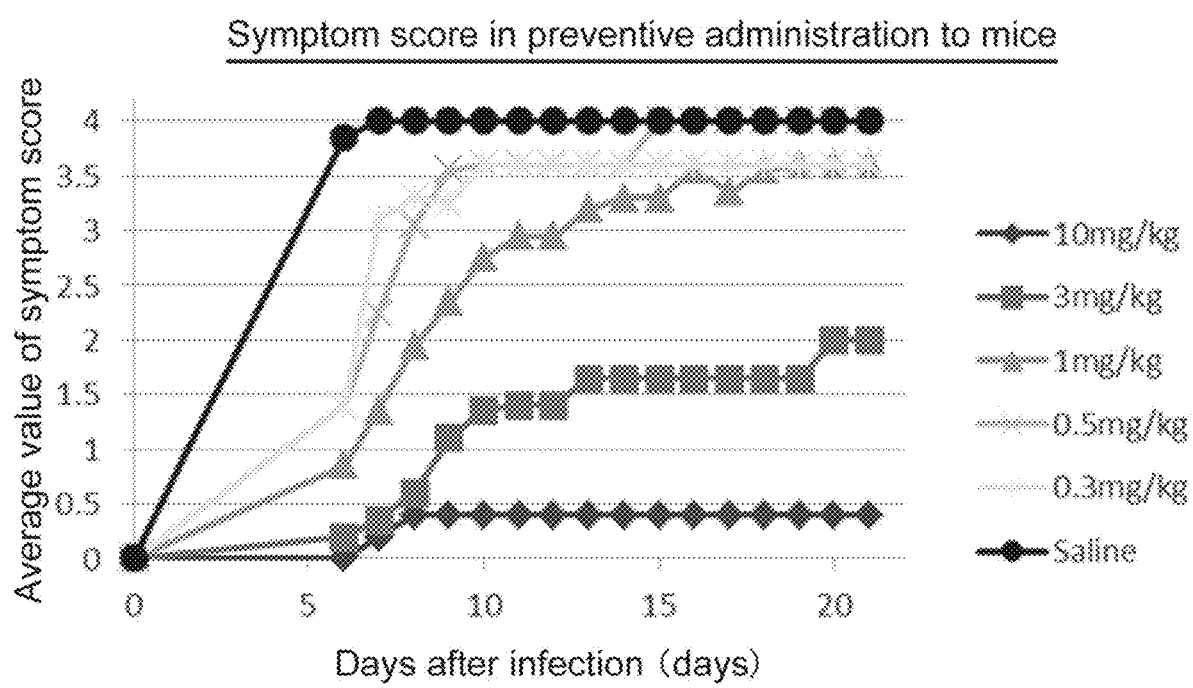
FIG. 5 presents a diagram showing symptom scores after preventive administration of the anti-gD antibody to mice in Example 5.
Figure 6:
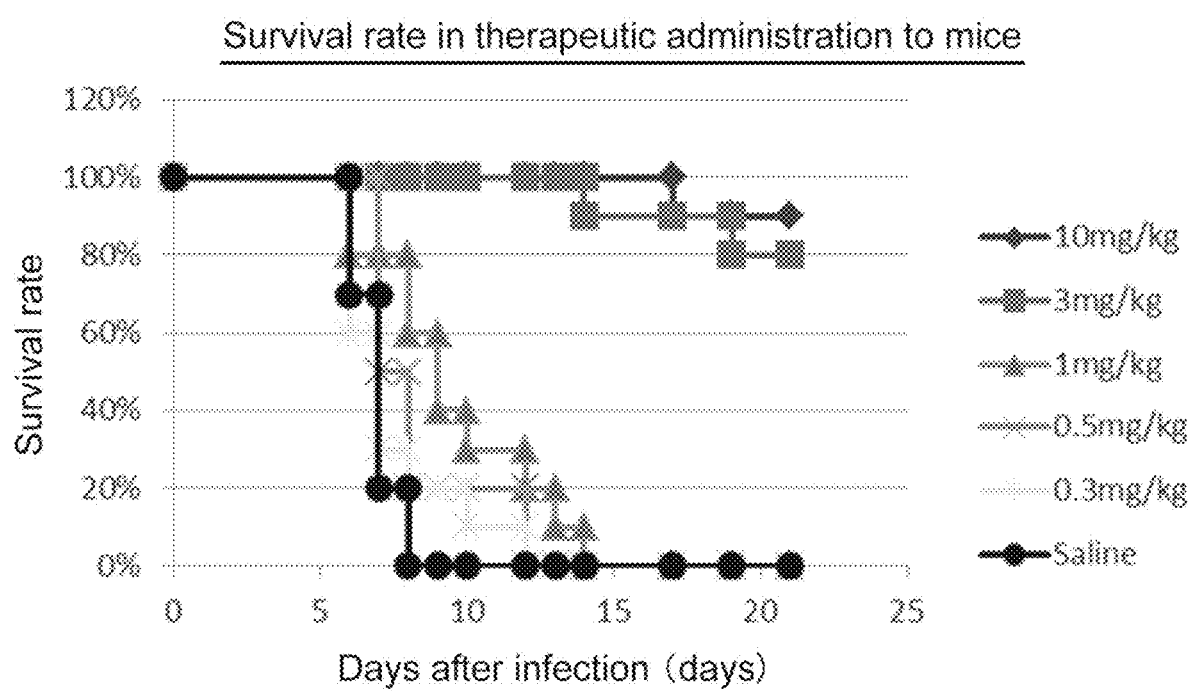
FIG. 6 presents a diagram showing survival rate after therapeutic administration of the anti-gD antibody to mice in Example 5.
Figure 7:
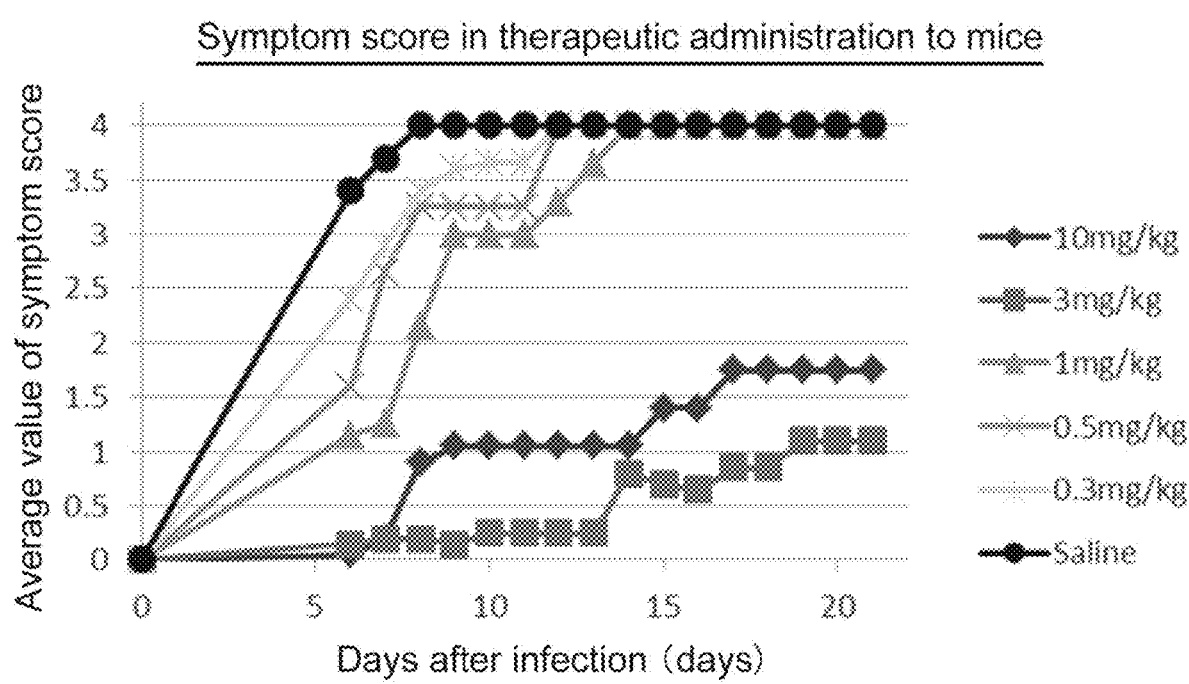
FIG. 7 presents a diagram showing symptom scores after therapeutic administration of the anti-gD antibody to mice in Example 5.

The survival times by dosage, the survival rates and the symptom scores in preventive administration are shown in Table 7, FIG. 4, and FIG. 5, respectively. The survival times by dosage, the survival rates, and the symptom scores in therapeutic administration are shown in Table 8, FIG. 6, and FIG. 7, respectively.

In preventive administration, a significant survival time prolongation effect relative to the saline administration group, which was set as a negative control group, was shown at all set dosages (10 mg/kg, 3 mg/kg, 1 mg/kg, 0.5 mg/kg, 0.3 mg/kg). In particular, significant survival rate and improved symptom scores were shown in two doses 10 mg/kg and 3 mg/kg of high dose range.

TABLE 7

Survival time after preventive administration of antibody No. 82 IgG2a to mouse

| | Dosage (mg/kg) | Survival time after infection (days) | Mean survival time (days) | Significant difference test (vs saline) |
|---|---|---|---|---|
| No. 82 preventive administration | 10 | 7, >21, >21, >21, >21, >21, >21, >21, >21, >21 | >21 | *** |
| | 3 | 7, 9, 10, 12, 19, >21, >21, >21, >21, >21, | >20 | *** |
| | 1 | 7, 7, 7, 8, 8, 9, 10, 12, 18, >21 | 8.5 | *** |
| | 0.5 | 6, 6, 6, 6, 7, 8, 8, 8, 9, 14 | 7.5 | ** |
| | 0.3 | 6, 6, 6, 6, 6, 6, 6, 7, 9, >21 | 6 | ** |
| saline | | 5, 5, 5, 5, 5, 5, 5, 6, 6, 6 | 5 | |

*** p < 0.0001/
** 0.0001 < p < 0.001/
* 0.001 < p < 0.05 (Kaplan-Meier method)

In therapeutic administration, it has been reported that the HSV transits from the site of infection to ganglion within 48 hours after the entry into the body (Non Patent Literature 8). However, therapeutic administration of antibody No. 82 at 48 hours after the infection showed significant improvement in survival rate and symptom scores at 2 doses of 10 mg/kg and 3 mg/kg, substantially the same as in the preventive administration. From the above, it was confirmed that antibody No. 82 exhibits a potent infection prevention effect not only in preventive administration but also in therapeutic administration.

TABLE 8

Survival time in therapeutic administration of antibody No. 82 IgG2a to mouse

| | Dosage (mg/kg) | Survival time after infection (days) | Mean survival time (days) | Significant difference test (vs saline) |
|---|---|---|---|---|
| No. 82 therapeutic | 10 | 16, >21, >21, >21, >21, >21, >21, >21, >21, >21 | >21 | *** |
| | 3 | 13, 18, >21, >21, >21, >21, >21, >21, >21, >21 | >21 | *** |

TABLE 8-continued

Survival time in therapeutic administration of antibody No. 82 IgG2a to mouse

| | Dosage (mg/kg) | Survival time after infection (days) | Mean survival time (days) | Significant difference test (vs saline) |
|---|---|---|---|---|
| administration | 1 | 5, 5, 7, 7, 8, 8, 9, 11, 12, 13 | 8 | * |
| | 0.5 | 6, 6, 6, 6, 6, 7, 7, 7, 11, 11 | 7.5 | * |
| | 0.3 | 5, 5, 5, 5, 6, 6, 6, 7, 9, 11 | 6 | N.S. |
| saline | | 5, 5, 5, 6, 6, 6, 6, 6, 7, 7 | 6 | |

*** p < 0.0001/
** 0.0001 < p < 0.0001/
* 0.001 < p < 0.05 (Kaplan-Meier method)

Example 6 Evaluation of Guinea Pig Infection Prevention Ability Against Anti-gD2 Antibody No. 82

Infection prevention ability of anti-gD2 antibody No. 82 in the preventive and therapeutic administration was evaluated using the guinea pig genital herpes infection model (acute phase).

<Guinea Pig Infection-Prevention Test>

An infection-prevention test of anti-gD2 antibody No. 82 (human-guinea pig chimeric IgG2κ) in the preventive and therapeutic administration was performed using a guinea pig genital herpes infection model. Hartley guinea pig (3-5 weeks old, female) purchased from Japan SLC, Inc. was used. A predetermined amount of the antibody was dissolved in saline for injection and administered intraperitoneally 1 mg to 30 mg/kg/guinea pig 24 hours before viral inoculation for preventive administration and 4 days after viral inoculation for therapeutic administration. For therapeutic administration, symptom observation was performed prior to administration, and individuals presenting vaginal symptoms were sorted and randomized to avoid deviation in average scores for each group. The number of N=10-15 cases per group was set. Viral inoculation was performed by transvaginally inoculating $5 \times 10^5$ PFU/50 μL HSV-2 MS strain under anesthesia and acute phase symptoms were observed for 2-3 weeks after inoculation. Symptom scores were set as 0: no clear lesion, 0.5-1: erythema, 1.5-2: localized blisters, 2.5-3: localized ulcers or scabs, 3-5: extensive blisters/ulcers or scabs, 3-7: extensive ulcers or scabs with incontinence, 7.5: euthanasia due to severe symptoms, 8: death. Vaginal swabs were also collected at day 7 after viral inoculation and the virus release amount was measured by plaque method. Vaginal swabs were collected by inserting a cotton swab moistened with MEM medium into the vagina, then wiping off the mucosa on the vaginal inner wall. Vaginal swabs collected were suspended in MEM medium dispensed by 1 mL into siliconized tubes and stored frozen until use. Vaginal swabs as stock solution, or 10-fold, 100-fold, 1000-fold dilution were inoculated at 100 uL/well into 96-well or 48-well full-sheet Vero cells. Viral adsorption was performed at 37° C. for 1 hour after vaginal swab inoculation, and cultured in 1% methylcellulose in 2% FBS MEM medium for 24 to 72 hours, then the plaque number was measured in a predetermined manner.

<Results>

Figure 8:
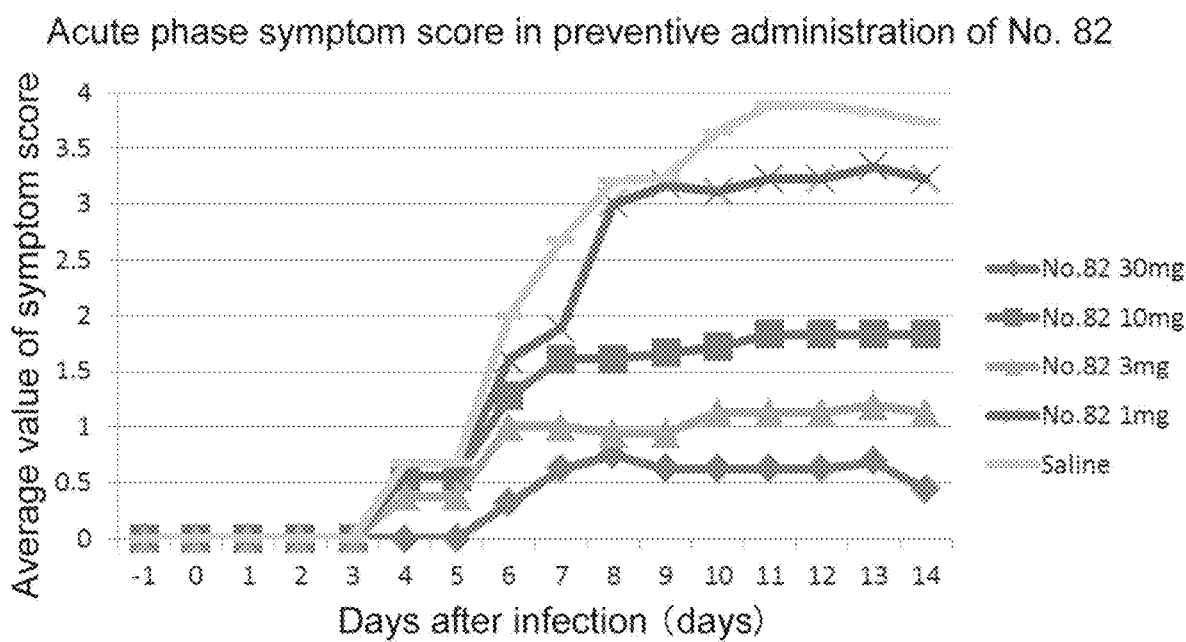
FIG. 8 presents a diagram showing symptom scores after preventive administration of the anti-gD antibody to guinea pigs in Example 6.
Figure 9:
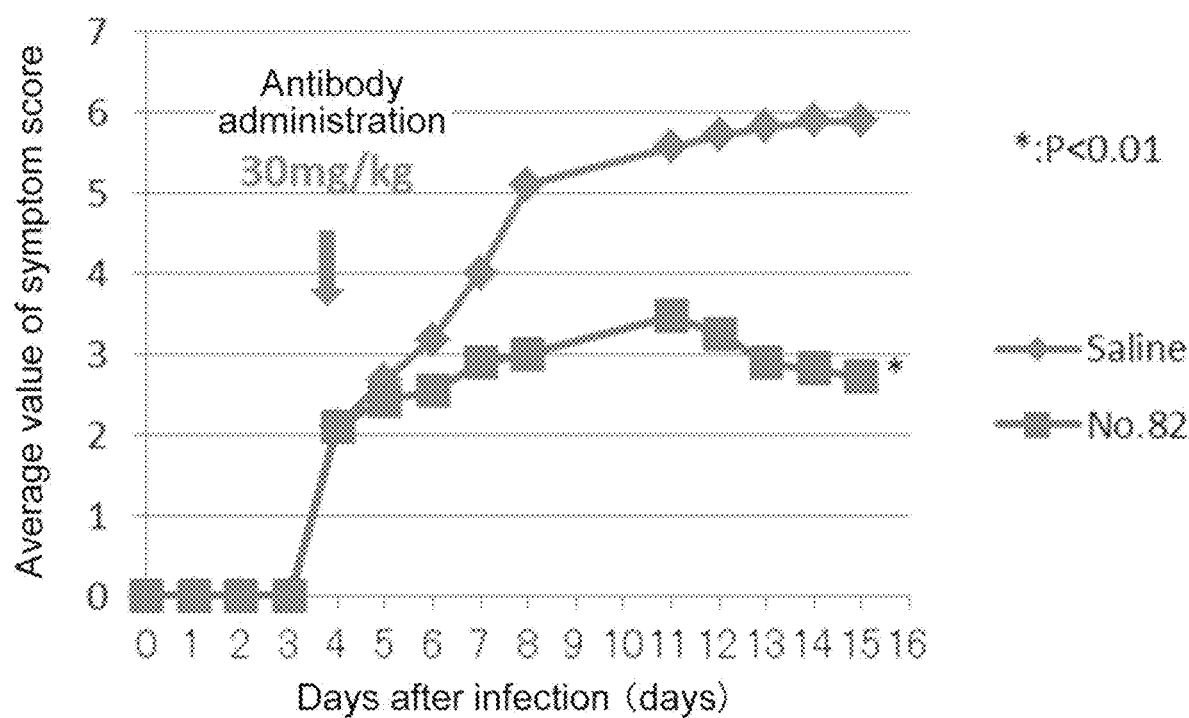
FIG. 9 presents a diagram showing symptom scores after therapeutic administration of the anti-gD antibody to guinea pigs in Example 6.
Figure 10:
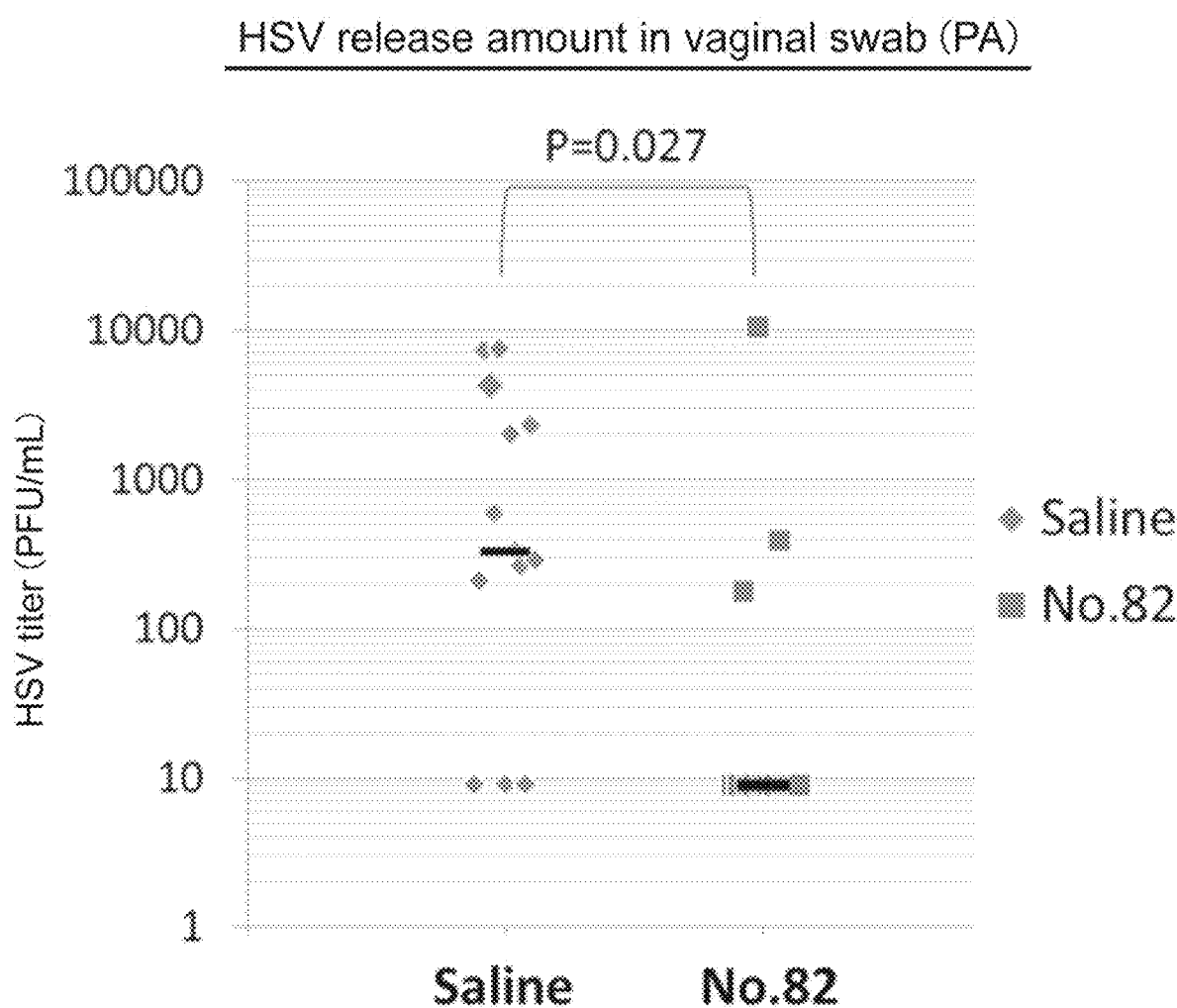
FIG. 10 presents a diagram showing HSV release amounts in a vaginal swab after therapeutic administration of the anti-gD antibody to guinea pigs in Example 6.

Symptom scores in preventive administration are shown in FIG. 8. The symptom scores in the results of therapeutic administration and the HSV release amounts in the vaginal swab are shown in FIG. 9 and FIG. 10, respectively.

In preventive administration, significant improvement in symptom scores relative to the saline administration group set as a negative control group was shown at 30 mg/kg, 10 mg/kg, and 3 mg/kg among the set dosages (30 mg/kg, 10 mg/kg, 3 mg/kg, 1 mg/kg).

In therapeutic administration, therapeutic administration of antibody No. 82 at 30 mg/kg to guinea pigs that were already presenting vaginal symptoms at 4 days after infection showed a significant relief in symptom scores relative to the saline administration group set as a negative control group. Furthermore, vaginal swabs were harvested at 7 days after virus inoculation and the virus release amount was measured by a plaque method. As the result, a significant reduction in viral release amount relative to the negative control group was observed.

From the above, it was confirmed that antibody No. 82 exhibits significant infection prevention effect not only in preventive administration but also in therapeutic administration.

Example 7 Comprehensive Analysis of T Cell Epitopes Present on HSV gD

<Exploration of HLA Class II Constrained Promiscuous T Cell Epitope Cluster Sequences Present on HSV gD2>

For gD2 full-length amino acid sequence of HSV-2 333 strain published in GenBank (ABU 45433.1; SEQ ID NO: 3), HLA Class II constrained promiscuous T cell epitope cluster sequences were explored using an algorithm (EpiMatrix) by EpiVax, Inc. The cluster sequence is a peptide sequence consisting of 15-25 amino acids that are predicted to have high probability (Z-Score≥1.64) to bind to a majority of the eight major HLA DR super type (DRB1*0101, DRB1*0301, DRB1*0401, DRB1*0701, DRB1*0801, DRB1*1101, DRB1*1301, DRB1*1501) which are analysis targets of EpiMatrix.

Exploration was performed using an algorithm (EpiMatrix) by EpiVax, Inc. As the result, five cluster sequences as shown in Table 9 were found. Among them, those that met criteria of EpiVax and were determined to be positive were the starred three sequences (DP1, DP3, DP4), while the other two sequences (DP2, DP5) were determined to be sufficiently probable even though they slightly failed to meet the criteria.

Peptide synthesis was performed for these 5 sequences. In these peptides, acetylation modification to the N-terminal side and amidation modification to the C-terminal side were added to increase stability. The peptide having the synthetic purity of 95% or more was dispensed into 2.5 mg/tube, then lyophilized and stored at −20° C. The lyophilized peptides were dissolved or suspended in DMSO (Sigma D2650) to 10 mM when used. The synthesized peptides were subjected to human and mouse T cell stimulation activity analysis.

TABLE 9

Predicted Promiscuous T cell epitope cluster sequence in HSV gD

| Sequence | | Amino acid sequence | Length | SEQ ID NO: |
|---|---|---|---|---|
| ☆ DP1 gD2 | 35-49 | KRVYHIQPSLEDPFQ | 15 | 4 |
| DP2 gD2 | 55-71 | ITVYYAVLERACRSVLL | 17 | 5 |
| ☆ DP3 gD2 | 170-191 | INDWTEITQFILEHRARASCKY | 22 | 6 |
| ☆ DP4 gD2 | 314-329 | PGLIIGALAGSTLAVL | 16 | 7 |
| DP5 | | IAFWVRRRAQMAPKPLR | 17 | 8 |

<T Cell Stimulation Activity Analysis of Synthetic Peptides Using Human PBMCs>

Serum from human PBMC donors sold from Cellular Technology Limited. (C.T.L.) was screened using anti-HSV IgG antibody detection ELISA kit (DENKA SEMEN Co., Ltd.) and PBMCs from HSV infected (antibody-positive) donors were purchased. The those purchased were frozen samples of PBMCs from donors with HSV exposure and having a homozygote or heterozygote of any of the eight major HLA DR super types (DRB1*0101, DRB1*0301, DRB1*0401, DRB1*0701, DRB1*0801, DRB1*1101, DRB1*1301, DRB1*1501) incorporated into the algorithm by EpiVax. PBMCs derived from anti-HSV antibody-negative donors (Donor 14, 67) were also purchased to analyze non-specific responses.

Following the protocol of C.T.L., frozen cells were thawed and washed with Thawing Medium (CTL Wash (TM) Medium), then prepared to a predetermined concentration in medium (CTL Test (TM) Medium) to subject human IFN-γ ELISpot assay. Cells were seeded in a 96-well plate dedicated to ELISpot at a concentration of 0.5 and $1 \times 10^7$ cells/mL by 100 μL, and to which 100 μL of each peptide solution prepared to 20 μM (final concentration: 10 μM/medium with 0.1% DMSO) was added, and cultured at 37° C. in $CO_2$ incubator for 5 days. The cells were then colored according to a predetermined protocol, and the number of positive cells (IFN-γ producing cells) for each well was measured with an ELISpot reader. The evaluation was performed in culture medium with 0.1% DMSO using inactivated HSV-1 (10 PFU/cell), ConA (final concentration: 2 μg/mL) as a negative control (None). Detection of IFN-γ-producing cell numbers was performed using Human IFN gamma ELISpot Ready-SET-Go!® (eBioscience, Inc., 88-7386-88) by capturing images with ELISpot analyzer (CTL, Immunospot S5 versa analyzer) and counting the number of spots with Immunospot software.

All measurements of each sample were performed at three wells. The experimental results are shown in Table 10. Table 10(A) shows the average spot numbers of IFN-'γ-producing cell numbers, where the grey netting indicates that the spot numbers were too small to be determinable. Furthermore, Table 10(B) indicates the determination of the presence or absence of T cell stimulation activity by stimulation index (SI) against the negative control (None) as an indicator. The determination was performed as Positive when SI is 3, Marginal when SI is 2 or more and less than 3, and Negative when Si is less than 2. As the result, it was revealed that all five peptides had human T cell stimulation activity, and of which four peptides were capable of stimulating T cells of multiple human PBMCs of different HLA types.

TABLE 10

T cell stimulation activity analysis of synthetic peptides derived from HSV gD2 sequence using human PBMC (A) IFN-γ-producing cell numbers (average spot number)

| | DP1 | DP2 | DP3 | DP4 | DP5 | non | | |
|---|---|---|---|---|---|---|---|---|
| Donor4 | 21.0 | 45.5 | 29.0 | 22.5 | 19.5 | 19.0 | DR1-0101 | DR15-1501 |
| Donor9 | 51.0 | 57.5 | 21.5 | 13.0 | 34.5 | 7.0 | DR3-0301 | DR16-1601 |
| Donor 14 | 3.3 | 5.0 | 4.3 | 4.0 | 5.7 | 3.3 | DR3-0301 | DR15-1501 |
| Donor22 | 8.5 | 48.0 | 21.5 | 8.5 | 6.0 | 11.5 | DR4-0401 | DR9-0901 |
| Donor33 | 12.0 | 12.3 | 14.0 | 18.0 | 14.7 | 11.3 | DR8-0801 | DR15-1501 |
| Donor 36 | 2.7 | 9.0 | 6.3 | 3.3 | 19.3 | 5.7 | DR13-1302 | DR15-1501 |
| Donor60 | 0.3 | 4.6 | 1.3 | 0.4 | 1.7 | 1.0 | DR3-0301 | DR14-1454 |
| Donor62 | 30.0 | 74.3 | 55.7 | 57.3 | 30.3 | 44.0 | DR4-0403 | DR15-1501 |
| Donor 63 | 105.3 | 75.7 | 350.0 | 318.3 | 49.0 | 49.7 | DR11-1101 | DR11-1101 |
| Donor67 | 0.5 | 1.0 | 0.0 | 1.0 | 0.5 | 1.0 | DR1-0101 | DR7-0701 |

(B) Determination by stimulation index (SI)

| | DP1 | DP2 | DP3 | DP4 | DP5 | | |
|---|---|---|---|---|---|---|---|
| Donor4 | N | M | N | N | N | DR1-0101 | DR15-1501 |
| Donor9 | P | P | P | N | P | DR3-0301 | DR16-1601 |
| Donor22 | N | P | N | N | N | DR4-0401 | DR9-0901 |
| Donor33 | N | N | N | N | N | DR8-0801 | DR15-1501 |
| Donor 36 | N | N | N | N | P | DR13-1302 | DR15-1501 |
| Donor62 | N | N | N | N | N | DR4-0403 | DR15-1501 |
| Donor63 | M | N | P | P | N | DR11-1101 | DR11-1101 |

Positive(P): 3 ≤ SI,
Marginal(M): 2 ≤ SI < 3,
Negative(N): SI < 2

<Mouse T Cell Stimulation Activity Analysis of Synthetic Peptide>

T cell stimulation activity analysis was performed by mouse immunogenicity test of synthetic peptides. A stock solution in which the synthetic peptide was dissolved or suspended in 10 mM with DMSO was prepared. 10% HCO-60/saline (saline for injection) was also prepared as a solvent for administration using NIKKOL HCO-60 (manufactured by Nikko Chemicals Co., Ltd.). 100 µg of the synthetic peptide was mixed with 10 µg of CpG and 10 µg of MPLA in a solvent and prepared into a dose of 210 µl/mouse and administered subcutaneously to the back of the mouse (4-5 weeks old, female). Three strains of mouse BALB/c (I-Ad/I-Ed), C57BL/6 (I-Ab), and C3H/HeN (I-Ak/IEk) were used. Twenty-one days after the initial immunization, additional immunization was performed, and two weeks later, spleen was collected and splenocytes were prepared to be subjected to the following cytokine production response analysis (ELISpot assay). The prepared splenocytes were seeded in 96 wells of PVDF membrane (MSIPS4W10 Millipore) to $1 \times 10^6$ cells/well and cultured with 10 µM of various peptides for 20 hours. Culture was carried out using RPMI1640 medium under the presence of 10% FBS in an incubator set at 37° C. and 5% $CO_2$ concentration. A Con A addition group was set up as a positive control. Detection of IFN-γ-producing cells was performed using mouse IFN gamma ELISpot Ready-SET-Go!® (eBioscience, Inc., 88-7384-88). Images were captured with ELISpot analyzer (CTL, Immunospot S5 versa analyzer) and the number of spots were counted with Immunospot software.

Figure 11:
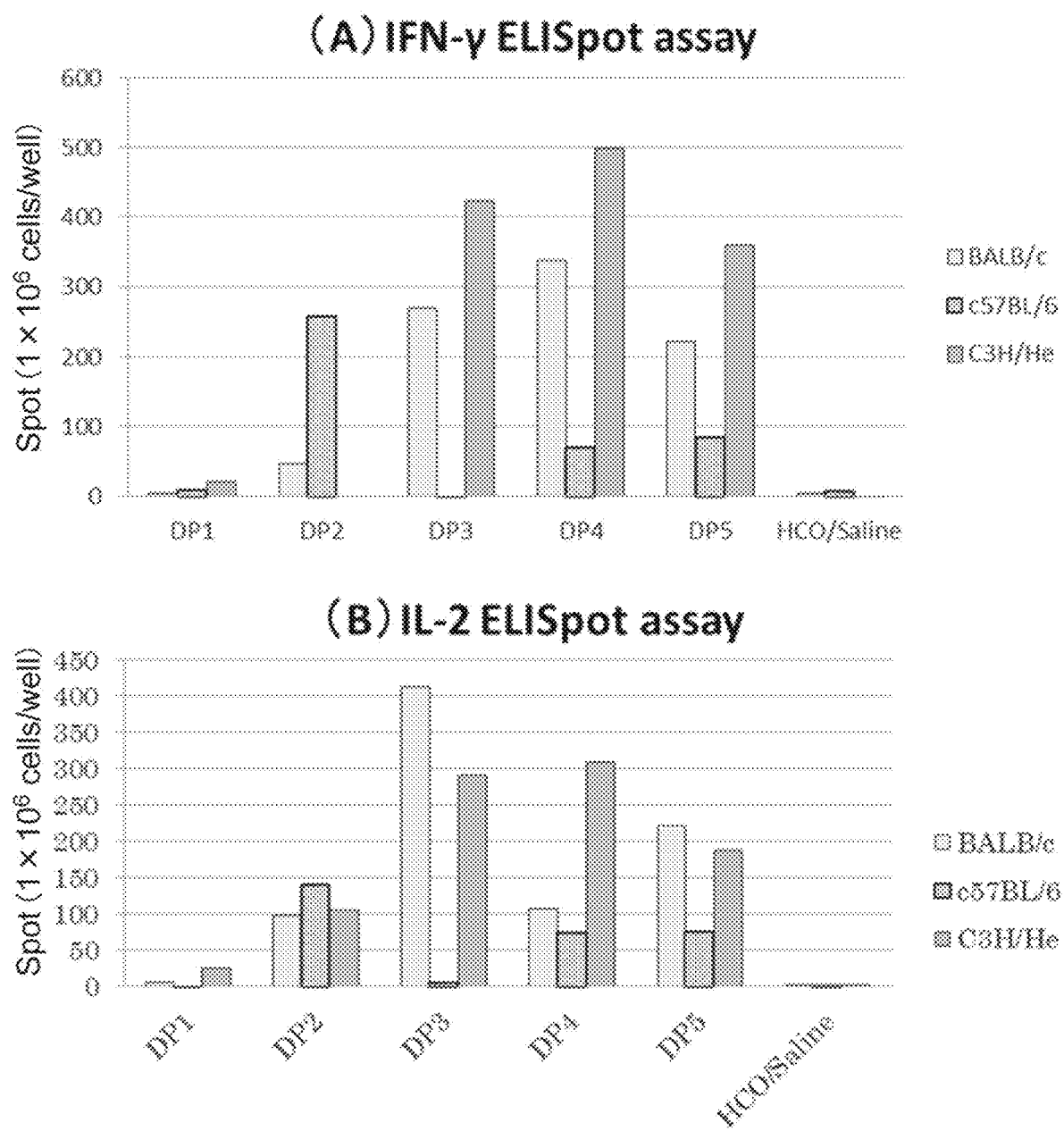
FIG. 11 presents a diagrams showing mouse T cell stimulation activity analysis of the synthetic peptide in Example 7. Panel (A) of FIG. 11 shows the results of ELISpot assay of the IFN-γ production and Panel (B) of FIG. 11 shows the results of ELISpot assay of the IL-2 production.

Each of the five peptides DP1 to DP5 was immunized to three strains of mice (n=2 for each group) of BALB/c (I-Ad/I-Ed), C57BL/6 (I-Ab), and C3H/HeN (I-Ak/IEk). Then, spleen was collected and splenocytes were prepared to analyze T cell responsiveness (IFN-γ and IL-2 production stimulation activity) to each peptide by ELISpot. All measurements of each sample were performed at two wells. The experimental results are shown in FIG. 11. In both the IFN-γ producing ELISpot assay FIG. 11, panel (A)) and the IL-2 producing ELISpot assay (FIG. 11, panel (B)), it was confirmed that four peptides other than DP1 were capable of stimulating two or more strains of mouse spleen T cells.

Example 8 Population Analysis of Anti-gD2 Antibodies Contained in Human Serum Fractions (Immunoglobulins)

To analyze the population of anti-HSV gD antibodies contained in the actual human serum, a competition test with the obtained antibodies was conducted using Venilon, a human gamma globulin cocktail (blood donation Venilon®-I for IV injection, General Foundation: The Chemo-Sero-Therapeutic Research Institute). As the competition test, gD1-315 were reacted with Venilon, then with monoclonal antibodies. In this system, it is believed that the higher the amount of competing antibodies contained in Venilon, the lower the binding amount of the monoclonal antibody (subject antibody) and higher the competition rate. SPR (Biacore, Inc.) was used in the competition test.

(Venilon Competition Test with SPR)

Competition Test was performed with Biacore 3000 (GE Healthcare). In all experiments, HBS-EP buffer (GE Healthcare) was used, the temperature was set to 25° C., and the flow rate was set to 10 µL/min. NTA (GE Healthcare) was used as the sensor chip. Based on the recommended protocol, 0.5 mM $NiCl_2$ was reacted for 10 seconds. gD1-315-His was then reacted at 3 µg/mL for 60 seconds and immobilized with about 300 resonance units (RU). When the analysis is performed using Biacore as the surface plasmon resonance sensor, the resulting signal value "RU" is expressed as the unit of 1 pg of the substance bound per $mm^2$. The chip regeneration was performed by treating the chip surface with 350 mM EDTA for 10 seconds, twice, and washing with Buffer for 10 seconds. Immobilization and regeneration were performed in a similar manner each time new samples were measured. Competition rates were calculated as follows: in the case that increased RU when an antibody under consideration at the concentration of 20 µg/mL is applied at a flow rate of 20 µL/min for 120 seconds is set to (1); and increased RU when Venilon at the concentration of 150 µg/mL is continued to be applied at a flow rate of 20 µL/min for 120 seconds, then the antibody at the concentration of 20 µg/mL is applied for 120 seconds is set to (2), the competition rate is calculated by the expression $(1-(2)/(1)) \times 100$. All samples were measured only once.

The analytical results of the Venilon Competition Test are shown in Table 11. The highest competition rate was shown for antibody No. 5, a weak neutralizing antibody, followed by antibody No. 13, antibody No. 75, antibody No. 78, and antibody No. 72, where the group of antibodies having an epitope in the P50 peripheral region were ranked high. Meanwhile, antibody No. 82 was the sixth of 7 clones, exhibiting a relatively low competition rate, and the lowest one was antibody No. 1.

From the above results, it was found that among anti-gD2 antibodies contained in human serum, the number of antibodies that recognize epitopes in the P50 peripheral region on wild-type gD antigen is greater than the number of antibodies that recognize epitopes on or around RBD. The P50 peripheral region was thought to be a decoy region that had high antibody inducibility but could induce many less beneficial antibodies.

TABLE 11

Presumed epitope region of various anti-gD2 antibodies and population analysis

| Group | Antibody No. | Epitope region | Competition rate (Inhibition %) |
|---|---|---|---|
| A | 82 | RBD (+FR1) | 10.0 |
| B | 1 | FR3 | 7.2 |
| C1 | 5 | P50 periphery + α | 37.9 |
|  | 13 | Unknown | 24.9 |
| C2 | 72 | P50 periphery (+FR3) | 15 |
|  | 75 | P50 periphery + FR3 | 20.2 |
|  | 78 | P50 periphery | 17.7 |

Example 9 Design of HSV gD Variants for Vaccine Antigens

In designing a gD protein variant in which RBD where the epitope of the neutralizing antibody is present as a beneficial epitope region; the P50 peripheral region and FR3 where the epitope of a group of less beneficial antibodies is present as decoy regions; and more neutralizing antibodies can be induced, the present inventors designed gD variants as described below considering three perspectives of emphasizing a beneficial epitope; performing de-epitoping of an epitope in a decoy region by glycochain introduction, deficiency mutation, or the like; and being capable of efficiently and effectively eliciting both a liquid and a cellular immune response by further linking the promiscuous T cell epitope cluster peptide, and examined their neutralizing antibody-inducing activities.

<Modified gD Design Policy>

As the beneficial epitopes present on the wild-type HSV gD antigen, the gD receptor binding domain (RBD), an epitope of anti-gD2 antibody No. 82, and the promiscuous T cell epitope cluster DP5 (SEQ ID NO: 8) predicted from T cell epitope analysis were assumed, and as the decoy region in which epitopes of relatively less beneficial groups of antibodies were concentrated, the P50 peripheral region was assumed.

In the design of modified gD based on the three aforementioned perspectives, the following three policies were adopted: (1) masking of the non-neutralizing epitope by introduction of a glycochain; (2) modification of the C-terminal side sequence FR3 of gD1-315; and (3) linkage of the T cell epitope peptide.

For introduction of a glycochain in (1), three sites R186 (SC-A), P74 (SC-D) and P50 (SC-F) were selected as modification site candidates. In particular, introduction of a glycochain into P50 (SC-F) was mainly carried out because obtained results showed that SC-F inhibits binding of Group C1, a group of non-neutralizing antibodies.

For modification of the C-terminal side sequence FR3 of gD1-315 in (2), from the report on crystal structure analysis of HSV gD1 (Non Patent Literature 7), it was suggested that FR3 and the N-terminal side sequence FR1 can be bound to wrap around exactly the same surface of the core beta-sheet structure FR2 in the gD molecule. Since FR1 and FR3 interfere with each other, only one of them can bind to FR2. It has been presumed that on the viral envelope FR3 normally binds, but upon binding to the receptor, FR3 falls off, and the structure changes such that FR1 binds, and the receptor binding region is exposed. From the epitope analysis of antibody No. 82, it has been found that antibody No. 82 binds to a Nectin-1 binding region, has reduced reactivity with the FR1-deficient mutant (gD34-315), and inhibits binding of gD to HVEM or Nectin-1. That is, it is believed that defecting FR3 or inhibiting binding of FR3 to FR2 is effective in order to emphasize the epitope of antibody No. 82, and to induce immune refocusing on the region. FR3-deficient mutants were based on gD1-275 as reported in a literature (Non Patent Literature 12). It was also expected that the presence of an epitope of antibody No. 1 on FR3 would inhibit the induction of some non-neutralizing antibodies due to FR3 deficiency. Furthermore, from the viewpoint of inhibiting binding of FR3 to FR2, it was based on gD1-315 V231W mutant (gD1-315V) similarly reported in a literature (Non Patent Literature 9). It has been suggested that the V231W mutation inhibits binding of FR3 to FR2. Although this variant could not be expected to inhibit the induction of non-neutralizing antibodies such as antibody No. 1, it was considered possible to emphasize the epitope of antibody No. 82.

For the linkage of the T cell epitope peptide in (3), T cell immune response can be induced by linking the sequence of the predicted T cell epitope to the C-terminal or the like of the variant. T cell epitopes are also present in the transmembrane region and the intracellular region, but given their use as a vaccine, the design in the secretory phenotype composed of the extracellular regions is required. Then, by linking T cell epitopes present in the transmembrane region or intracellular region, the T cell epitope that is not included in the extracellular region can be effectively utilized. Since only three sequences DP1-3 of the predicted 5 peptides were included in the gD2 ectodomain sequence, the effect of linking DP5, an epitope sequence of the intracellular region, was considered significant. Thus, the modification was mainly proceeded with the one linked to two DP5.

Figure 12:
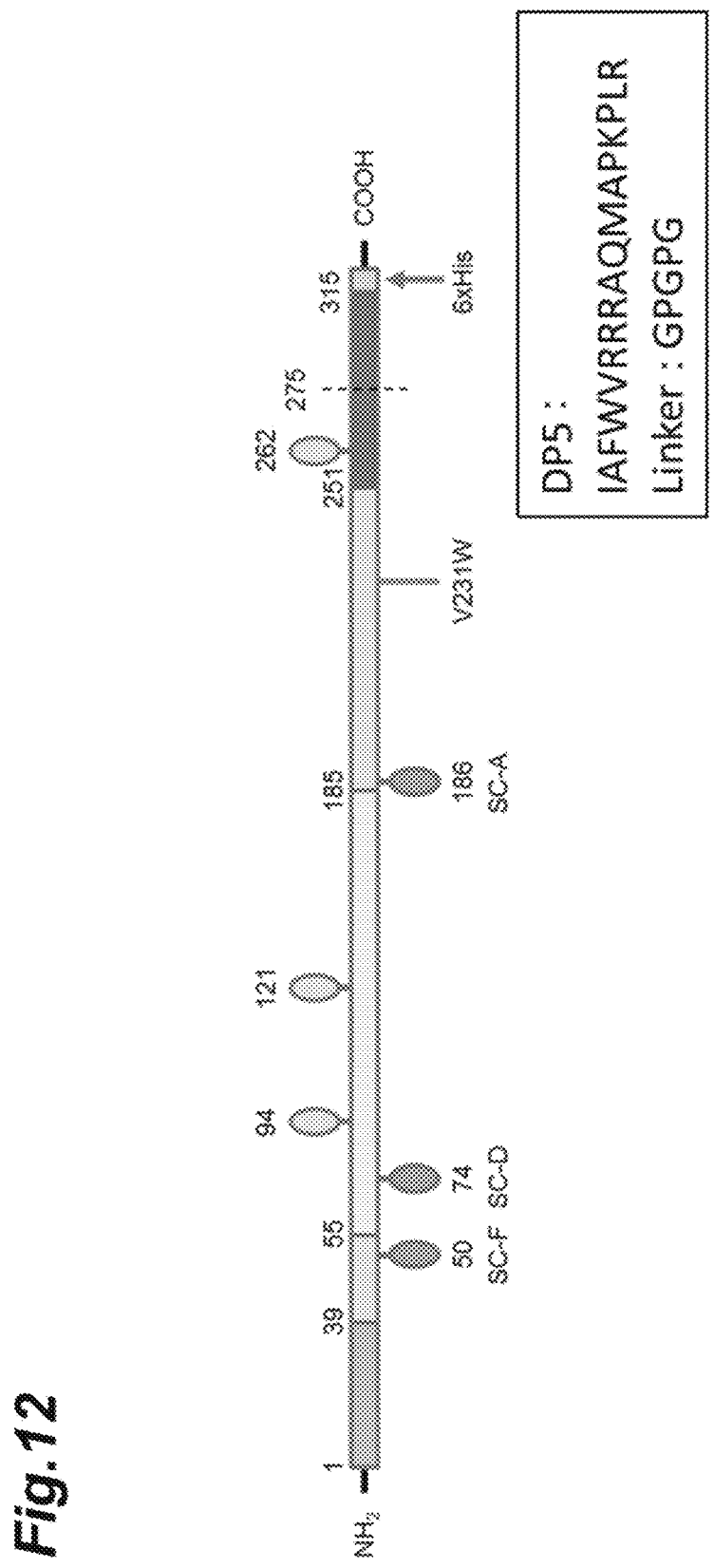
FIG. 12 presents a schematic diagram illustrating a design strategy for a modified gD protein. The sequences shown on this figure are IAFWVRRRAQMAPKPLR (SEQ ID NO: 8) and GPGPG (SEQ ID NO: 34).

A schematic diagram of the above modified gD design strategy is shown in FIG. 12. FIG. 3 also shows the conformation model of HSV gD2 monomers added with the glycochain introduction sites and expected antibody No. 82 epitopes or the like.

<Design, Expression and Reactivity Analysis of Modified gD>

Based on the above three policies, modification of gD2 was proceeded to yield a total of 16 variants (Table 12). Production of the variants was performed according to the following methods.

(Plasmid Construct)

The plasmid constructions of gD1-275, gD1-315 and primers used in introducing glycochains were as previously described. In the case that T cell epitope peptide was introduced, DNA was designed to link C-terminal residues (D275 or G315) of the gD sequence of interest, followed by a linker (GPGPG)(SEQ ID NO:_34), each T cell epitope peptide, and 6×His-Tag in this order, and the full length was artificially gene synthesized and cloned into a pUC19 vector. The completed modified sequence was cloned into the pCAGGS1-dhfr-neo vector to acquire a plasmid for expression.

Four gD1-275-based variants were produced. Since these were FR3-deficient variants, V231W mutations affecting FR3 were not investigated. The introduction of the glycochain alone (gD1-275v3, gD1-275v5) led no change in properties, but the presence of aggregates was confirmed in gD1-275v3-55 among the variants further linked to DP5. Since the difference from gD1-275v5-55, which had well properties, was whether R186 (SC-A) was introduced or not, it is presumed that the conformational structure of R186 (SC-A) present structurally in the vicinity of 275aa prevents the structural changes that trigger aggregation such as the adsorption of DP5 to the main body portion. Meanwhile, eight gD1-315-based variants were produced, and none of the variants were less than the original gD1-315 in both properties and expression level.

<Analysis of Reactivity of Variant with Various Anti-gD2 Monoclonal Antibodies>

(Expression and Purification of Antibodies and gD Variant)

Each anti-gD2 monoclonal antibody and each gD variant were expressed using an Expi293 expression system. After 4-6 days of culture, the supernatant was purified with Protein A affinity chromatography column or Ni-NTA affinity chromatography column and dialyzed with PBS. The purity was confirmed by size exclusion chromatography and SDS-PAGE.

(Competitive ELISA with Anti-gD2 Antibody)

100 µL of the gD variant adjusted to a concentration of 2 µg/mL with phosphate buffered saline was immobilized in a 96-well microtiter plate overnight at 4° C. Each well was washed three times with PBS and blocked with 300 µL of 1% BSA PBS for 1 hour at room temperature. Each well was washed 3 times with PBS-T (0.05% Tween PBS). Each anti-gD2 antibody was diluted at any dilution fold with 1% BSA PBS, then 100 µL of the diluted antibody was added to the well, and reacted at 37° C. for 1 hour. Each well was washed again with PBS-T. Then, HRP-labeled antibody (anti-hFc/HRP/1% BSA PBS) was added and reacted at 37° C. for 1 hour. Each well was washed with PBS-T, then colored with TMB at room temperature for 30 minutes. After the reaction was stopped with 1N sulfuric acid, absorbance of 450 nm/650 nm was measured.

The results are shown in Table 12. Since reactivity with antibody No. 82 was confirmed in all variants, it was determined that there was no adverse effect on antibody No. 82 epitope according to the three policies. However, as expected, antibody No. 1, in which an epitope was present on FR3, did not exhibit reactivity with the gD1-275-based variant. Moreover, for antibody No. 13 whose epitope was previously unknown, it was found that the reactivity is eliminated by introducing P50 (SC-F) to a gD1-275-base (masking is possible). Given the result that the reactivity of antibody No. 13 remained when the modification is either the FR3 deficiency or the introduction of P50 (SC-F) alone, it is believed that P50 (SC-F) and FR3 may have coordinated to form some conformation, but the specific epitope remains unclear. Other antibodies of Group C showed generally expected reactivity. The introduction of P50 (SC-F) completely blocked binding of antibody No. 5 and antibody No. 78, while antibody No. 72 and antibody No. 75, in which the presence of a partial epitope in FR3 was suggested, showed weak reactivity with some variants. It was a desirable result as a vaccine antigen that the reactivity of antibody No. 72 and antibody No. 75, which are weak neutralizing antibody, was allowed to be remained.

and particularly gD1-315v5-55 showed approximately 12-fold more reactivity than the original gD1-315. Tandem linkage of DP5 to the C-terminal is believed that the sequence of DP5 itself plays a role in inhibiting binding of FR3 to the gD receptor binding region. The V231W mutants (gD1-315v3-55V, gD1-315v5-55V) resulted in a slightly reduced reactivity with antibody No. 82 compared to the unmutated variant (gD1-315v3-55, gD1-315v5-55). Although a literature (Non Patent Literature 9) introducing V231W reported that V231W has an effect of inhibiting FR3 binding, it is believed that V231W has in fact an effect of slightly inhibiting FR1 binding or altering the original binding structure depending on its bulkiness.

From the above discussion, it can be strongly inferred that each variant takes the structure in which FR1 is bound to the receptor binding region. The reactivity of HVEM with each variant was then measured by competitive ELISA.

Figure 14:
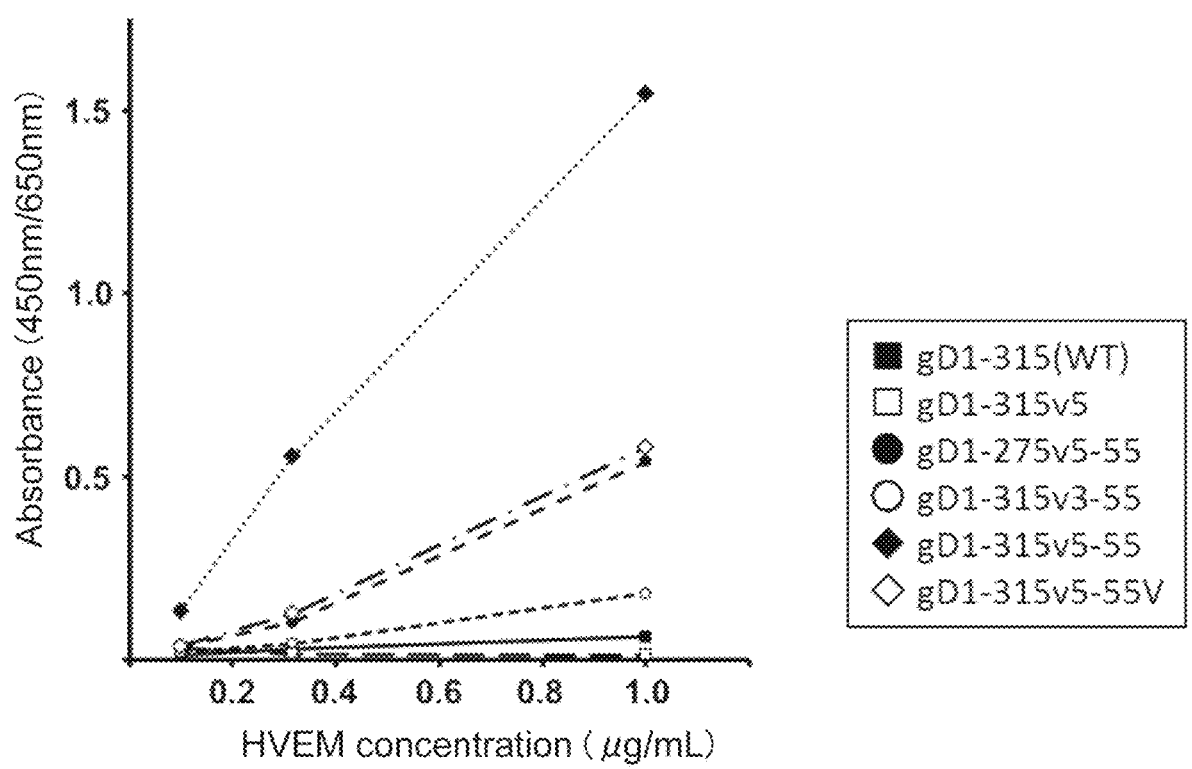
FIG. 14 presents a diagram showing the reactivity of various gD variants made in Example 9 with HVEM.
Figure 15:
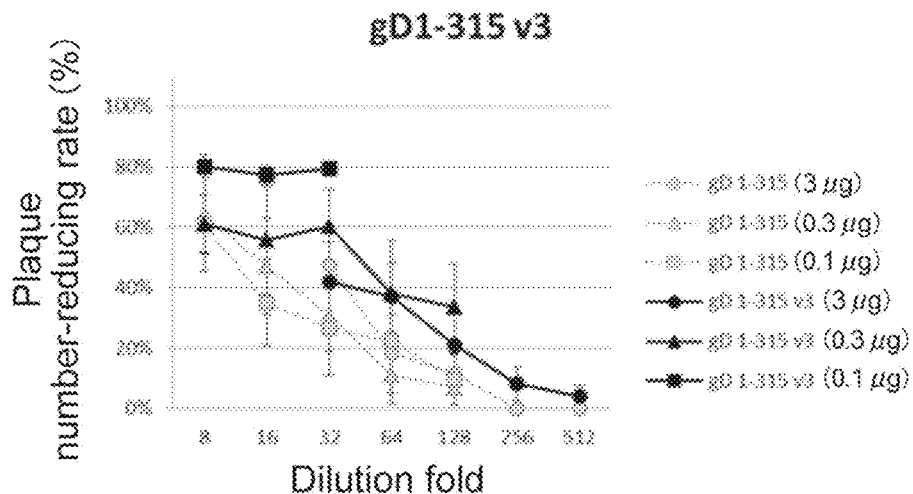
FIG. 15 presents diagrams showing the analysis results of neutralizing antibody-inducing activity using mice in Example 9.
Figure 15:
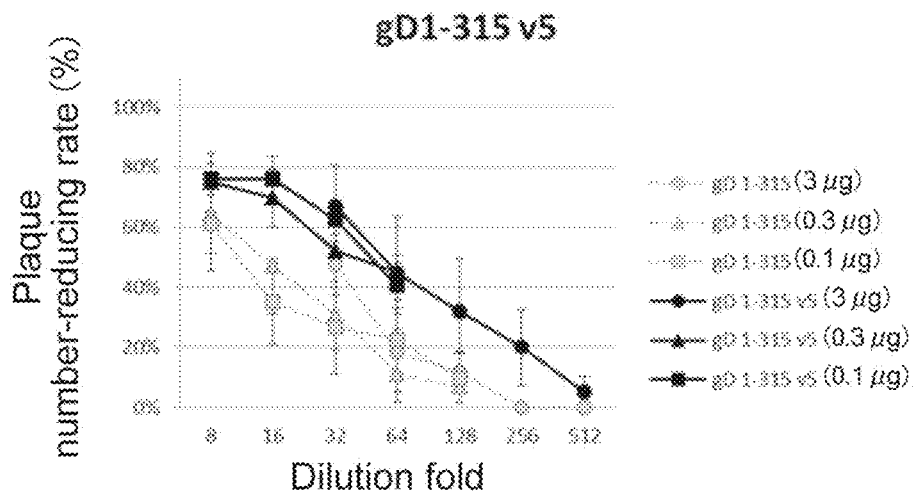
Figure 15:
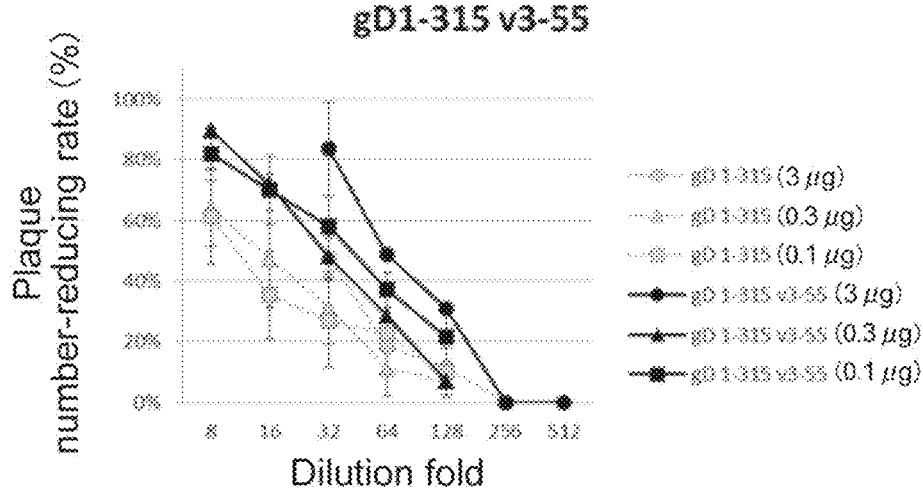
Figure 16:
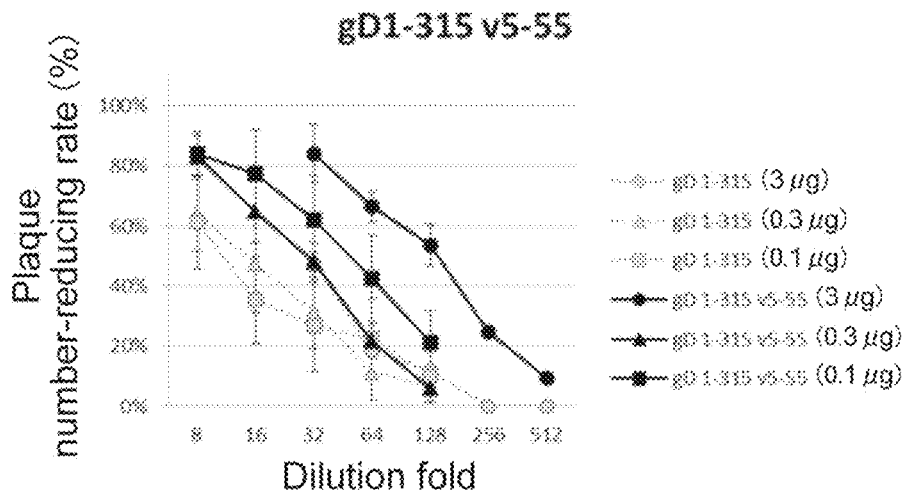
FIG. 16 presents diagrams showing the analysis results of neutralizing antibody-inducing activity using mice in Example 9.
Figure 16:
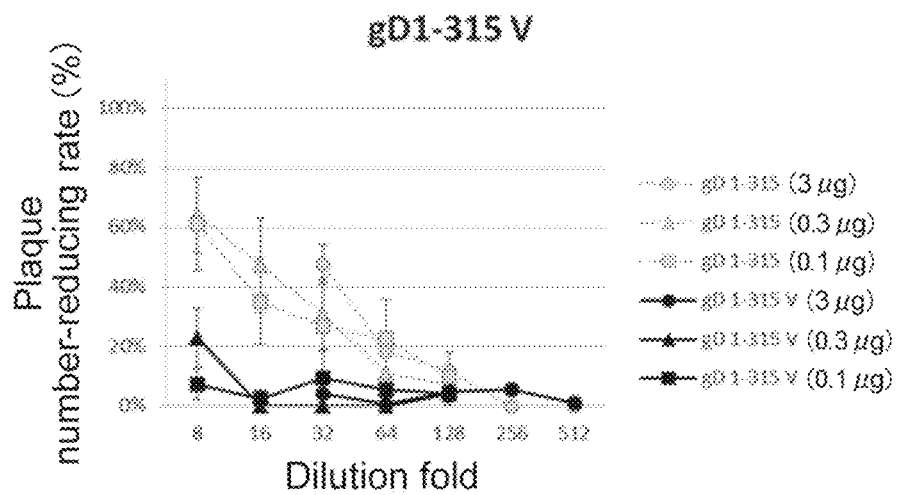
Figure 16:
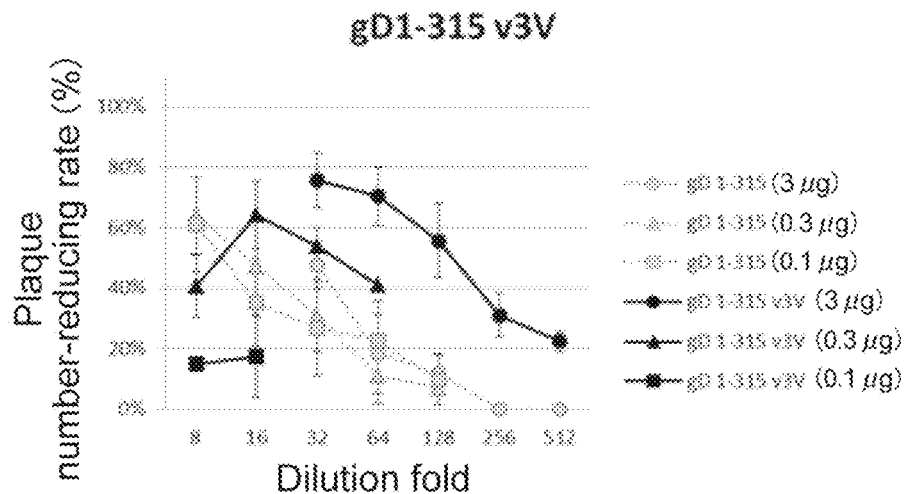
Figure 17:
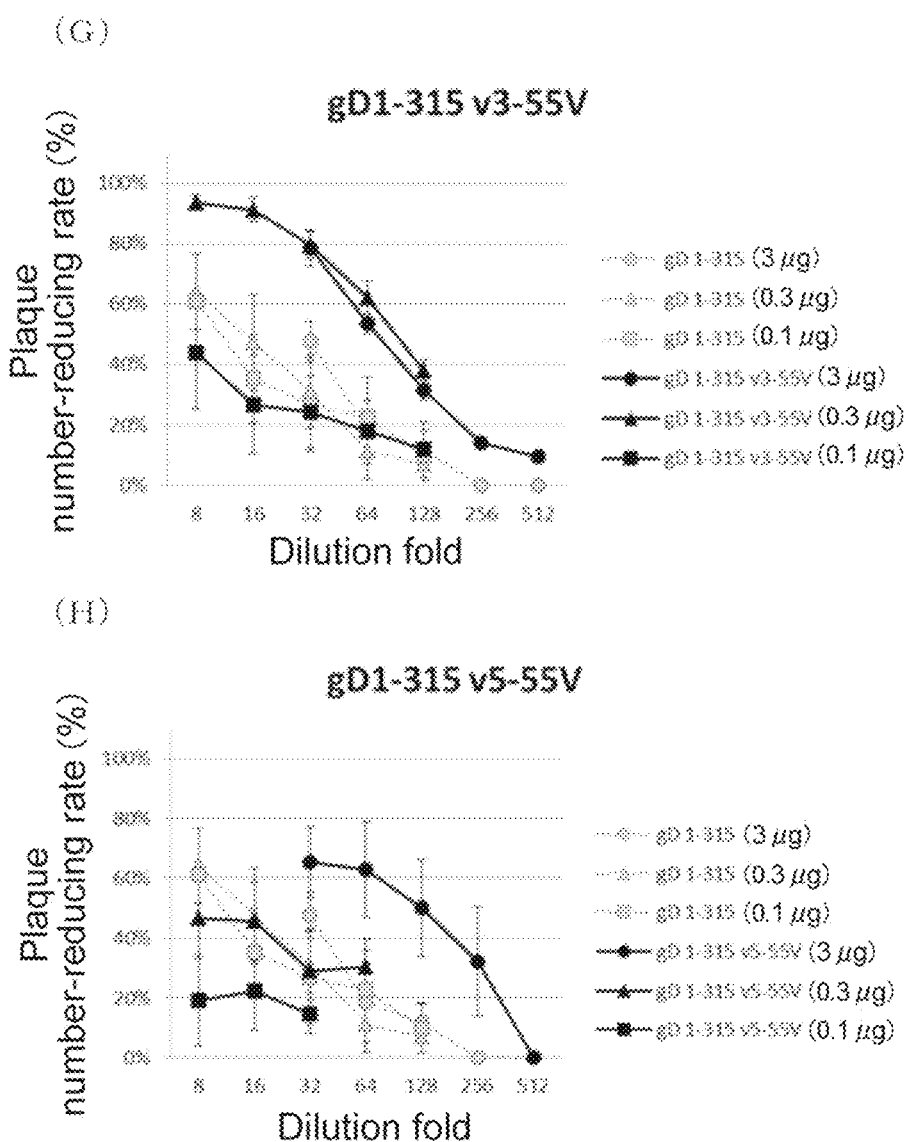
FIG. 17 presents diagrams showing the analysis results of neutralizing antibody-inducing activity using mice in Example 9.
Figure 18:
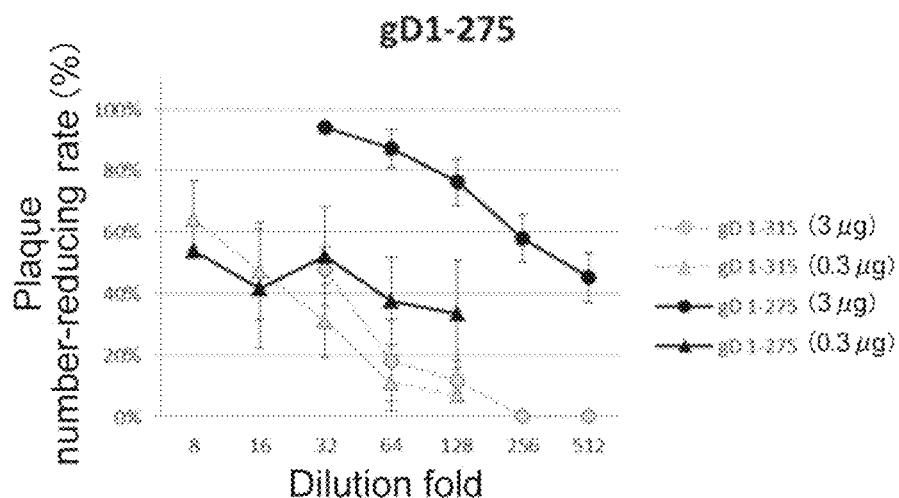
FIG. 18 presents diagrams showing the analysis results of neutralizing antibody-inducing activity using mice in Example 9.
Figure 18:
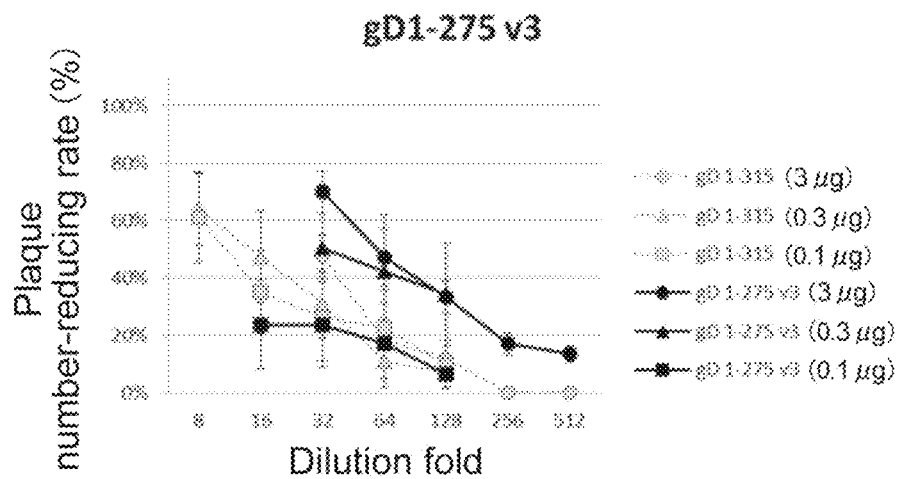
Figure 18:
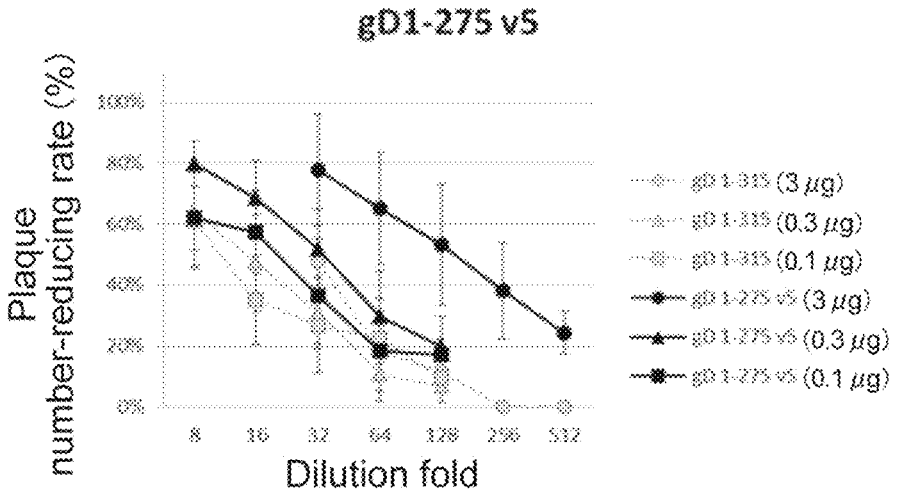
Figure 19:
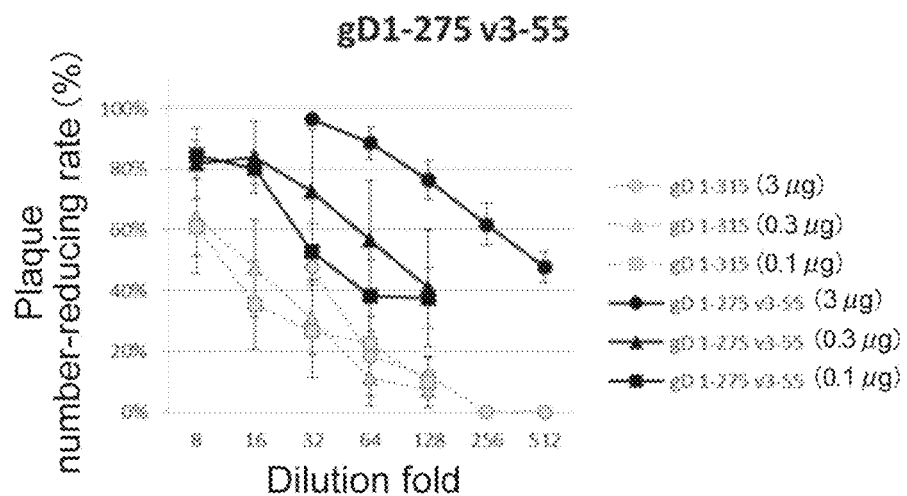
FIG. 19 presents diagrams showing the analysis results of neutralizing antibody-inducing activity using mice in Example 9.
Figure 19:
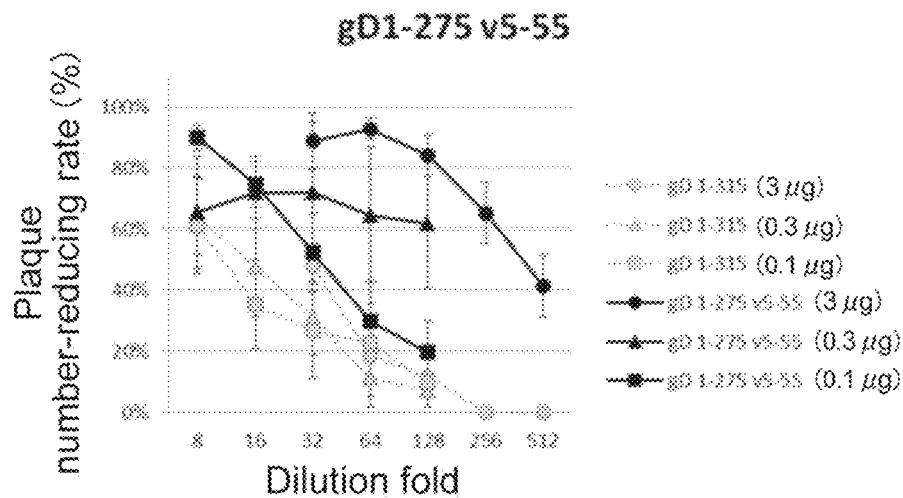
Figure 20:
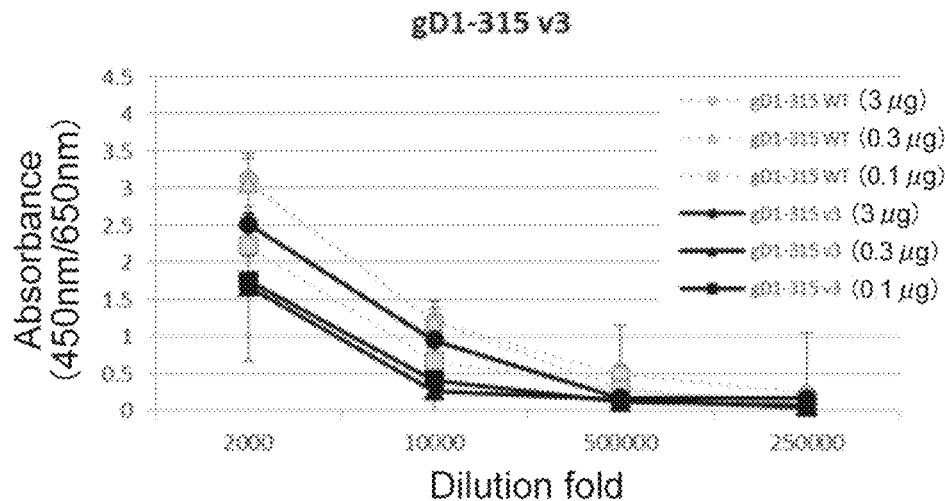
FIG. 20 presents diagrams showing the analysis results of anti-gD-binding antibody-inducing activity by ELISA method in Example 9.
Figure 20:
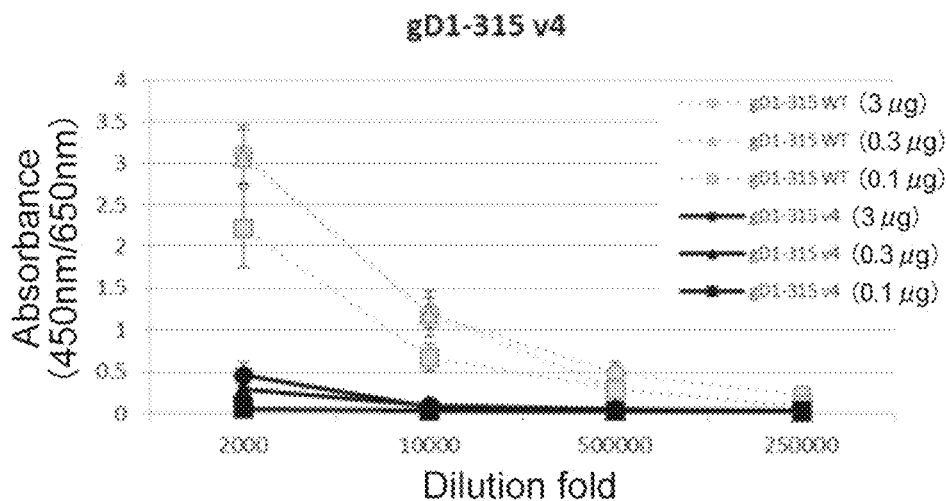
Figure 20:
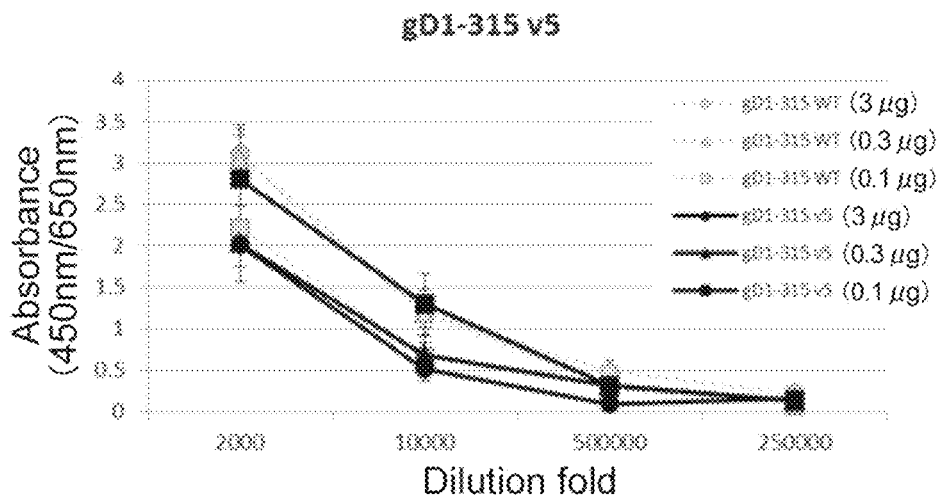
Figure 21:
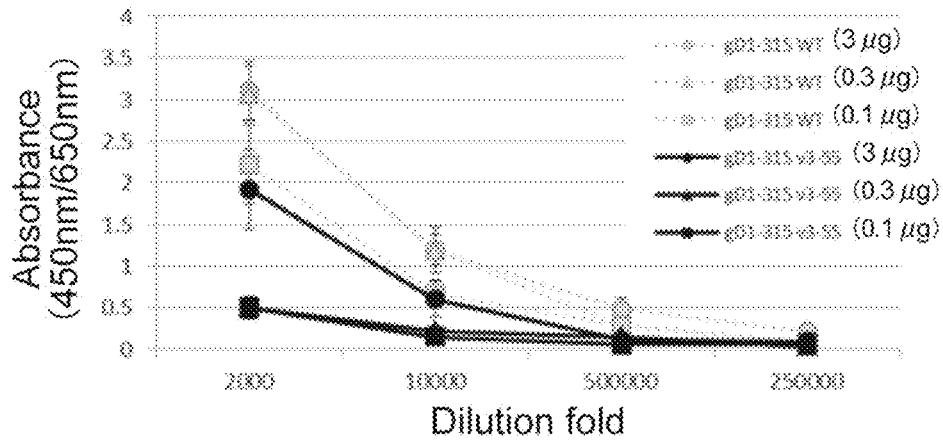
FIG. 21 presents diagrams showing the analysis results of anti-gD-binding antibody-inducing activity by ELISA method in Example 9.
Figure 21:
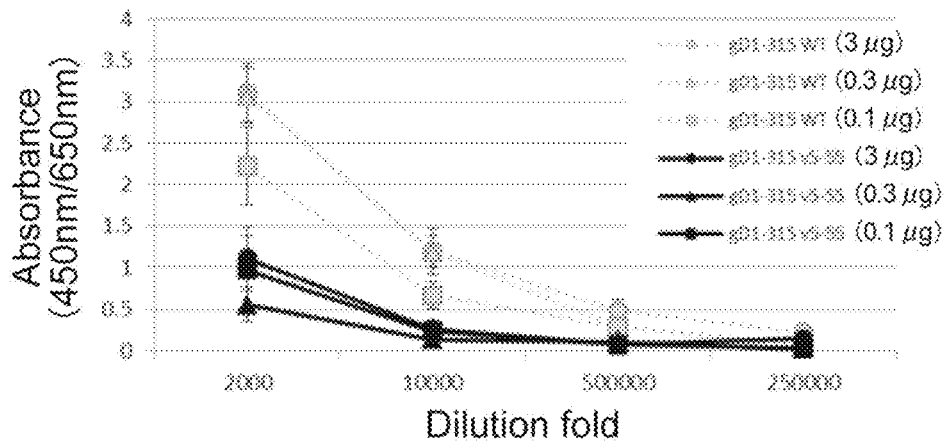
Figure 21:
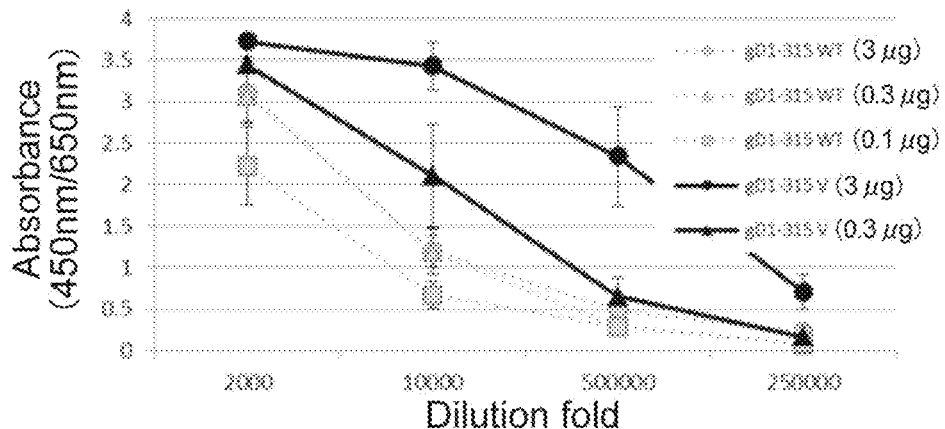
Figure 22:
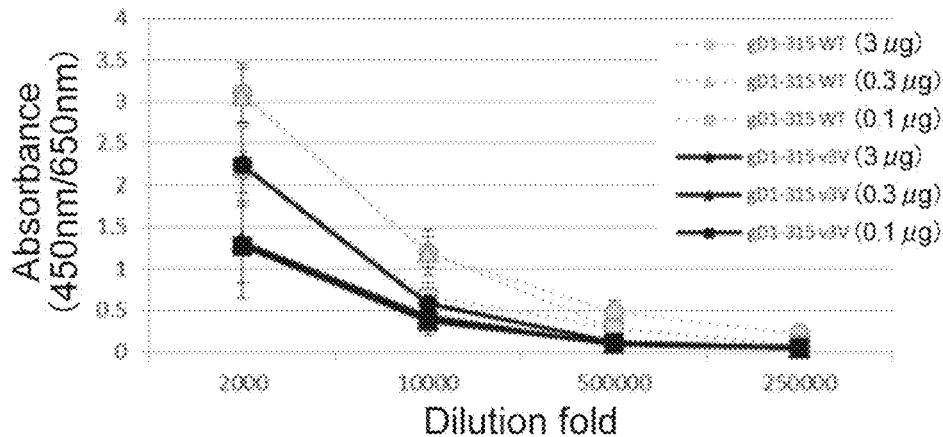
FIG. 22 presents diagrams showing the analysis results of anti-gD-binding antibody-inducing activity by ELISA method in Example 9.
Figure 22:
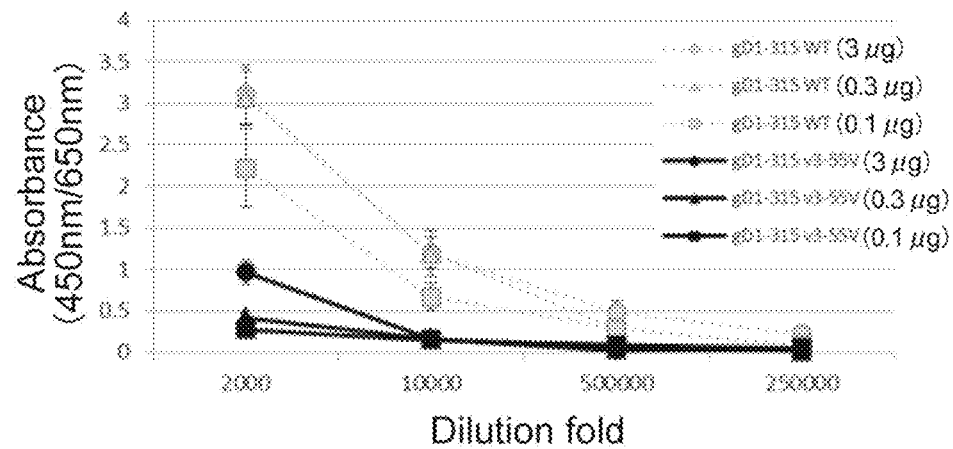
Figure 22:
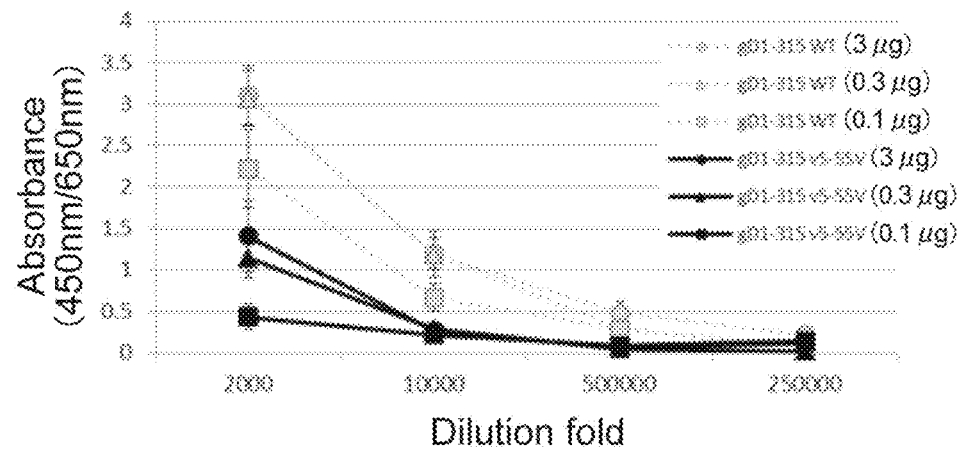
Figure 23:
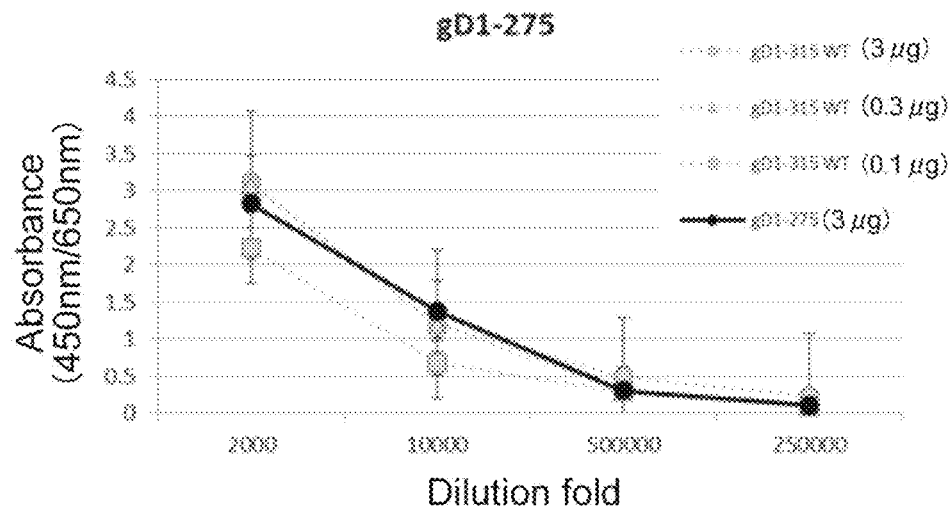
FIG. 23 presents diagrams showing the analysis results of anti-gD-binding antibody-inducing activity by ELISA method in Example 9.
Figure 23:
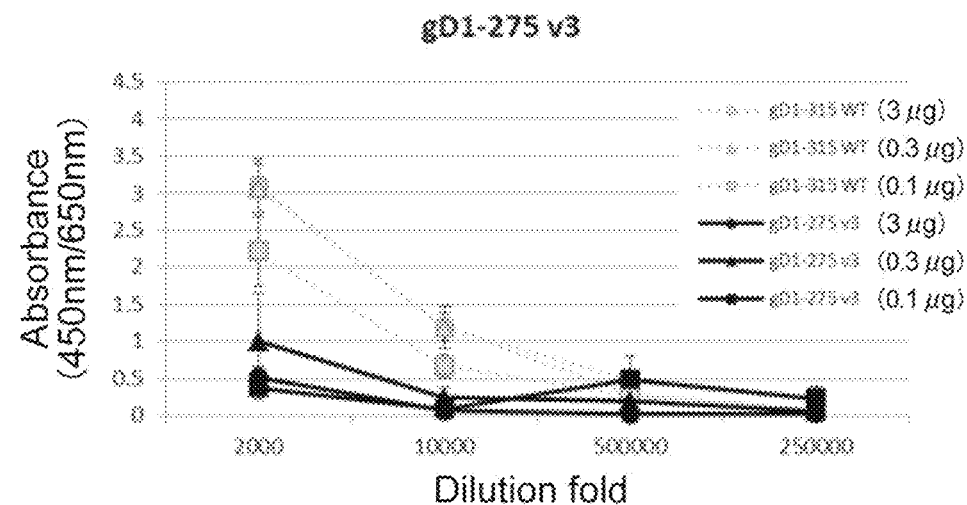
Figure 23:
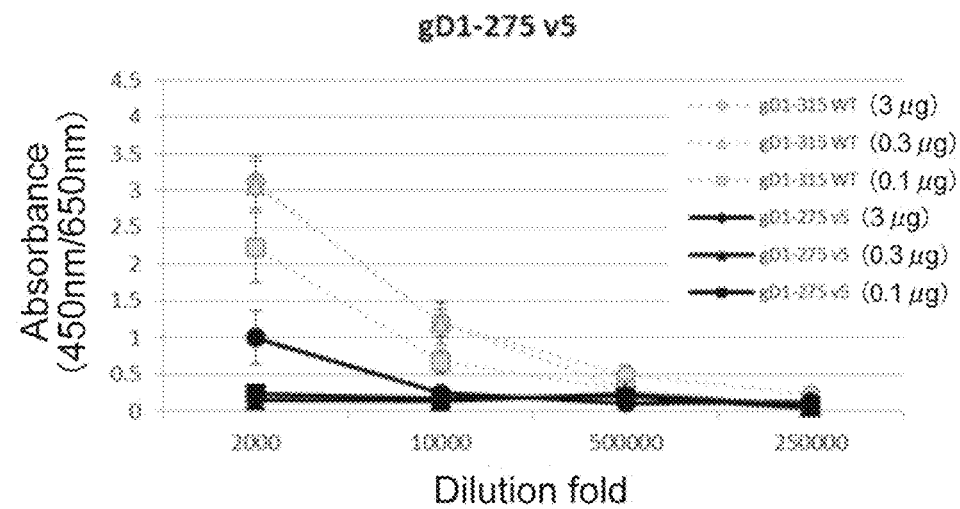
Figure 24:
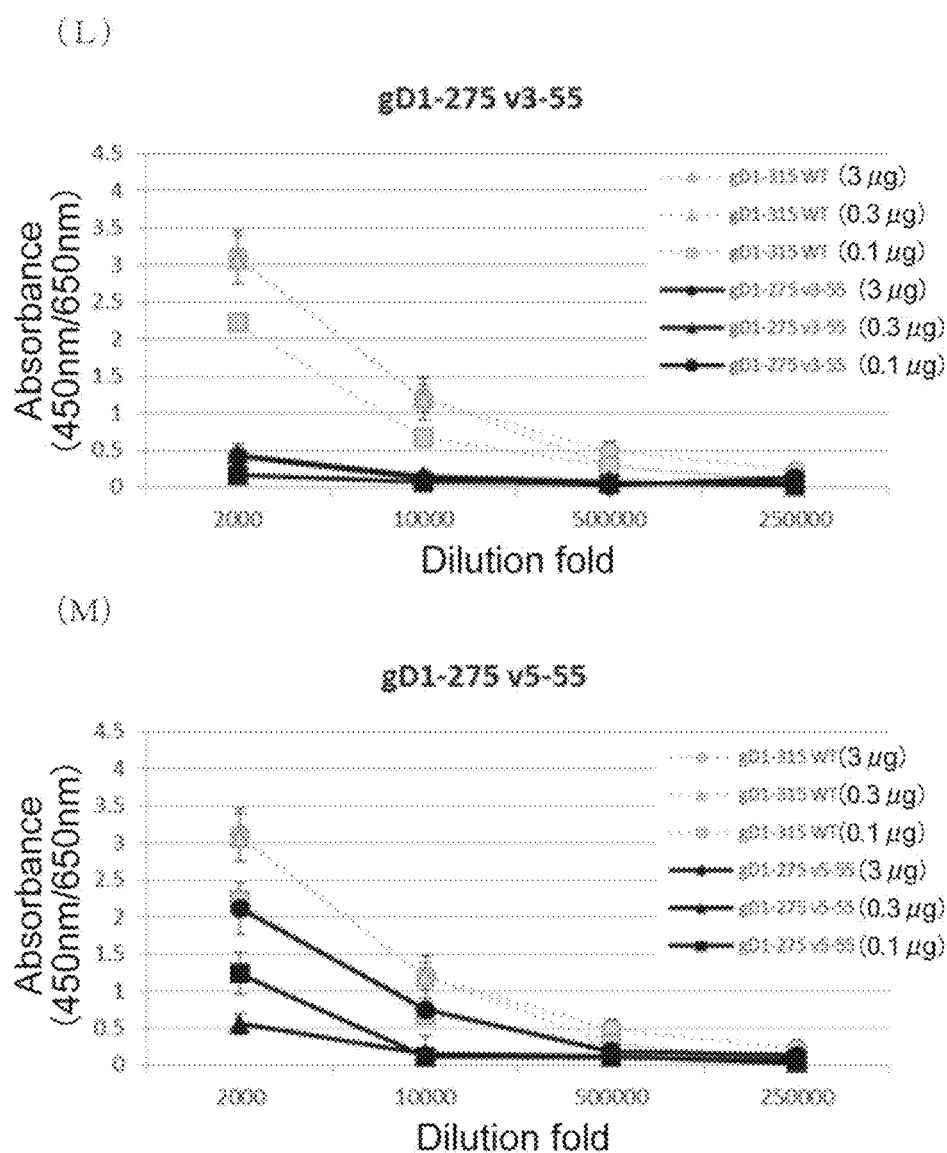
FIG. 24 presents diagrams showing the analysis results of anti-gD-binding antibody-inducing activity by ELISA method in Example 9.
Figure 25:
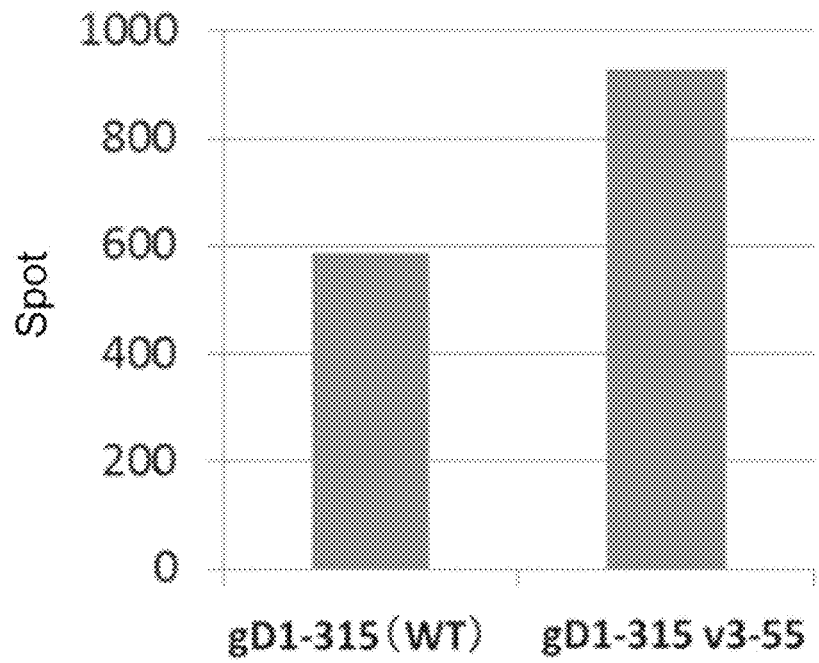
FIG. 25 presents diagrams showing the results of cellular immune (T cell immune)-inducing activity in Example 9.
Figure 25:
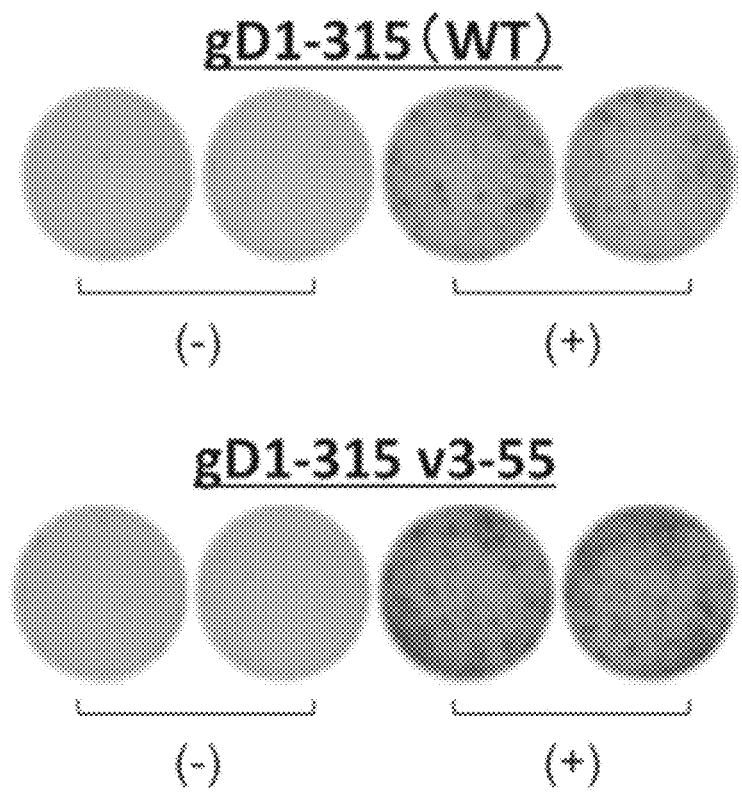
Figure 26:
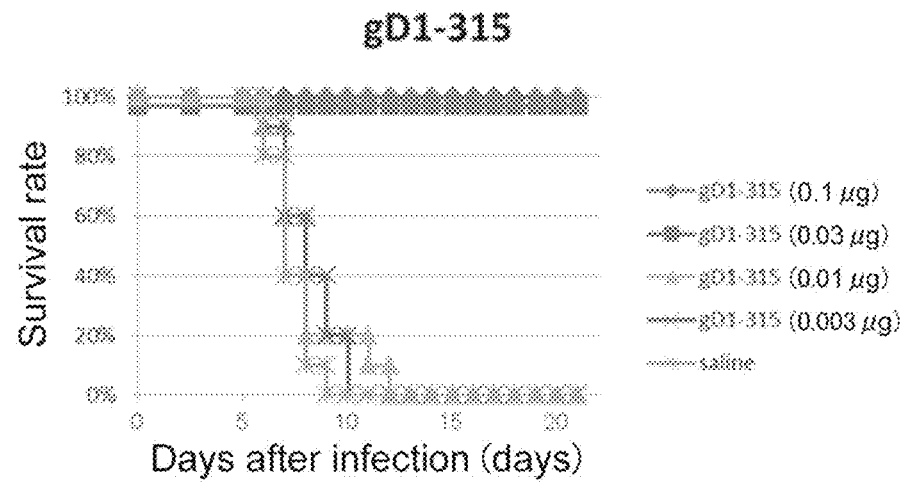
FIG. 26 presents diagrams showing the survival rate of Experiment 1 of the modified gD mouse infection-prevention test in Example 9.
Figure 26:
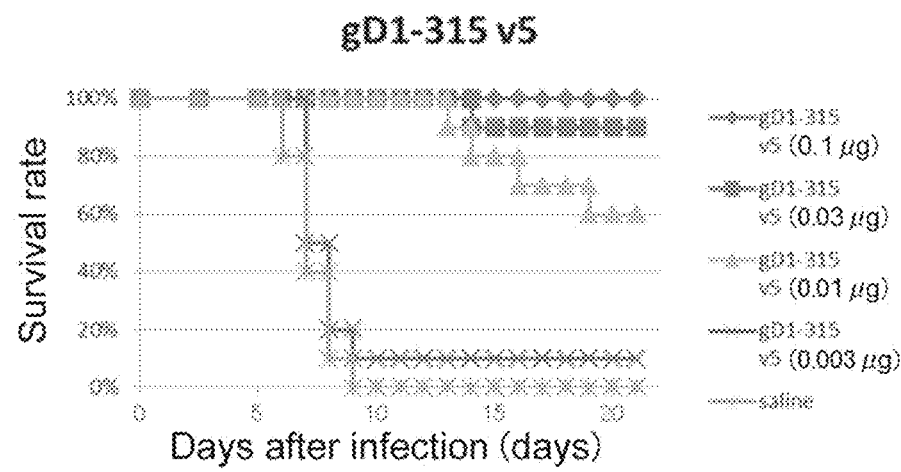
Figure 26:
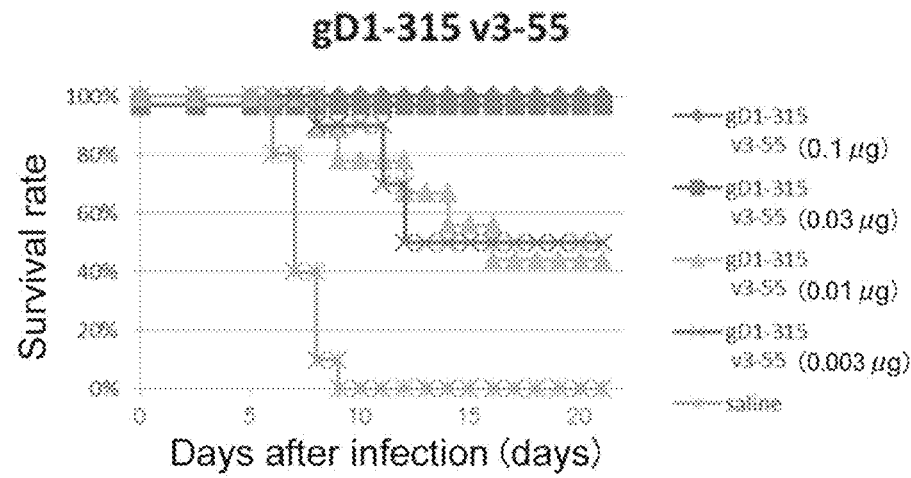
Figure 28:
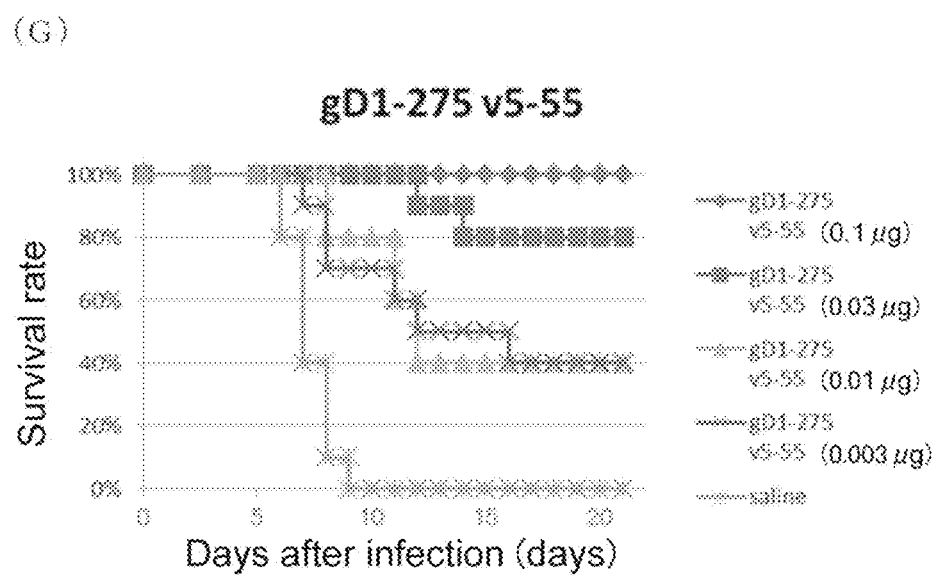
FIG. 28 presents a diagram showing the survival rate of mouse infection-prevention test Experiment 1 of the modified gD in Example 9.

The result is shown in FIG. 14. HVEM can bind gD for the first time when FR1 binds to the receptor binding region and takes a characteristic hairpin structure. All HVEM interaction sites were shown to be present in FR1, and increased reactivity with HVEM was as previously inferred. Compared to the original gD1-315, the highest reactivity with HVEM was shown for gD1-315v5-55, then gD1-315v5-55V or gD1-275v5-55, and gD1-315v3-55 in this

TABLE 12

Reactivity of produced gD modifieds with various anti-gD antibodies

| Modifieds | Introduction of glycochain | T cell epitope peptide | V231W | Remarks | Reactivity with various anti-gD2 antibodies | | | | | | |
|---|---|---|---|---|---|---|---|---|---|---|---|
| | | | | | 82 | 1 | 5 | 13 | 72 | 75 | 78 |
| gD1-275 | | | | Aggregation | + | − | + | + | + | + | + |
| gD1-275v3 | F | | | | + | − | − | − | − | − | − |
| gD1-275v3-55 | F | | + | | + | − | − | − | − | − | − |
| gD1-275v5 | A, F | | | | + | − | − | − | + | − | − |
| gD1-275v5-55 | A, F | | + | | + | − | − | − | − | − | − |
| gD1-315 | | | | Wild-type | + | + | + | + | + | + | + |
| gD1-315V | | | + | | + | + | + | + | + | + | + |
| gD1-315v3 | F | | | | + | + | − | + | + | − | − |
| gD1-315v3V | F | | + | | + | + | − | + | − | − | − |
| gD1-315v3-55 | F | + | | | + | + | − | + | − | − | − |
| gD1-315v3-55V | D, F | + | + | | + | + | − | + | ± | ± | − |
| gD1-315v5 | A, F | | | | + | + | − | + | ± | − | − |
| gD1-315v5V | A, F | | + | | + | + | − | + | ± | ± | − |
| gD1-315v5-55 | A, F | + | | | + | + | − | + | − | − | − |
| gD1-315v5-55V | A, F | + | + | | + | + | − | + | + | − | − |

Figure 13:
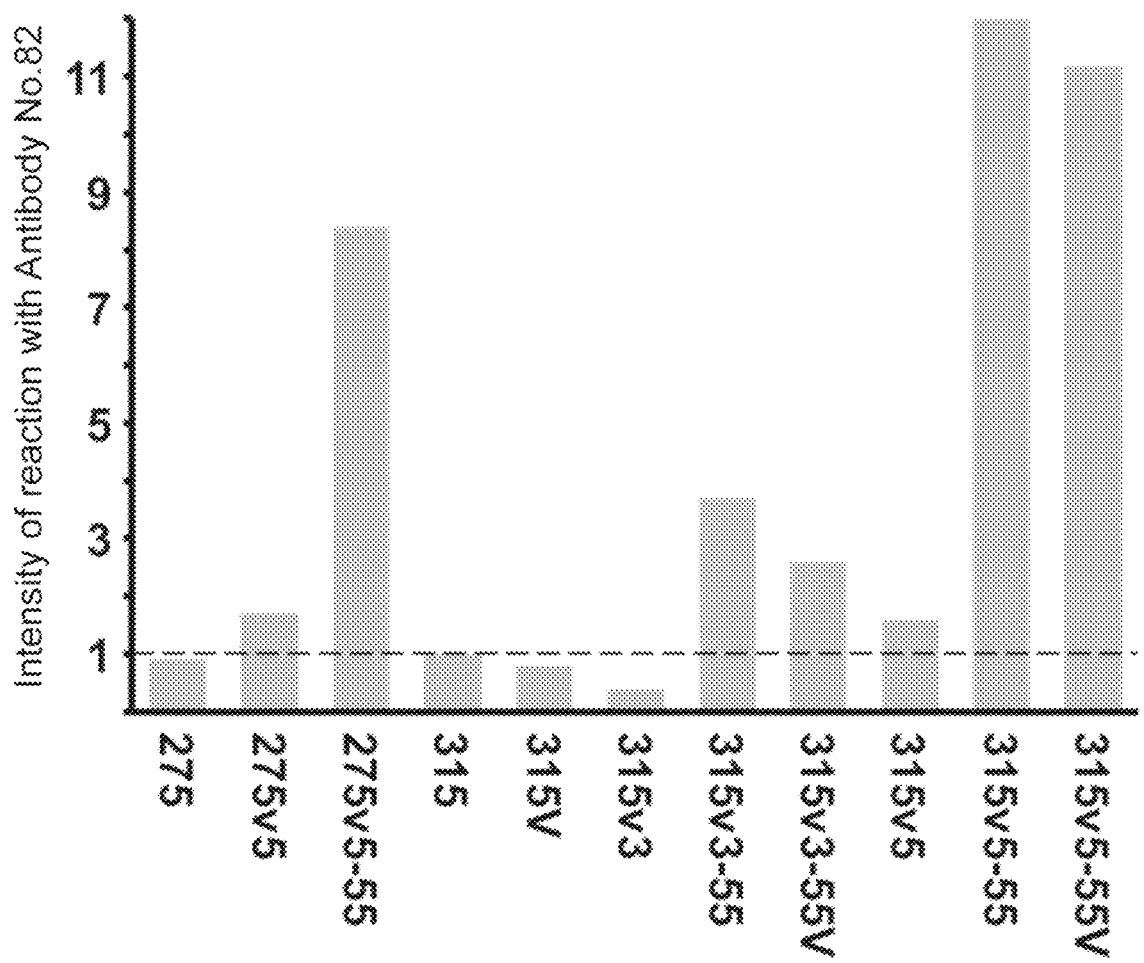
FIG. 13 presents a diagram showing the reaction intensity of the various gD variants made in Example 9 with anti-gD2 antibody No. 82.

Further detailed analysis was performed on the reactivity with antibody No. 82 (FIG. 13). FIG. 13 shows the relative values of the reactivity of each gD variant with antibody No. 82 when the reactivity of gD1-315 (wild-type) is set to "1". Antibody No. 82 bound to all gD variants produced, but the intensity of the reactivities was varied. Based on the reactivity of gD1-315 with antibody No. 82, the reactivity with antibody No. 82 was enhanced in most variants. From the viewpoint of glycochain introduction, the simultaneous introduction of P50 (SC-F) and R186 (SC-A) was more effective than the introduction of P50 (SC-F) alone (gD1-315v5-55, gD1-315v5-55V). As previously described, antibody No. 82 has epitopes in the gD receptor binding region and a portion of FR1. Similar to the reasons mentioned in aggregate formation of gD1-275v3-55, it is believed that R186 (SC-A) deprived flexibility of FR3 and created a situation in which FR1 was easier to bind to the gD receptor binding region. Furthermore, reactivity with antibody No. 82 was significantly enhanced in the variant linked to DP5, order, and little reaction was observed in gD1-315 and gD1-315v5. FR3-deficient gD1-275v5-55 promoted FR1 binding and further HVEM binding over other gD1-315-based variants in which FR3 was present. Since 1-275v5 and 1-315v5 showed substantially similar reactivity in the reactivity analysis with antibody No. 82, it can be inferred that the effect due to FR3 deficiency is approximately the same as that due to R186 (SC-A) introduction.

<Mouse Immunogenicity Test of Modified gD>

(Mouse Immunogenicity Test)

Immunogenicity test of the modified gD antigen was performed using the wild-type gD antigen gD1-315 (WT) as a positive control and saline as a negative control. A predetermined amount of antigen was dissolved in saline for injection (saline) with MPLA (10 µg/mouse) and CpG (1 µg/mouse) and immunized to mice at a volume of 200 µL/mouse. BALB/c mice (5 weeks old, female) were used for the study and immunized subcutaneously in back at 2-week intervals for a total of 3 times (N=4 cases per group). Two weeks after the final immunization (third dose), blood was collected and serum was prepared for each individual. The prepared serum was serially diluted and assessed for neutralizing antibody-inducing activity against HSV-2 (50% plaque number-reducing activity).

Analysis results for neutralizing antibody-inducing activity are shown in FIGS. 15-19. In each graph, the data for modified gD are shown in solid black lines, the data for wild-type gD are shown in gray dotted lines, and the high-dose administration group (3 µg/mouse) is shown in black circles, the medium-dose administration group (0.3 µg/mouse) in a black triangle and the low-dose administration group (0.1 µg/mouse) in black squares. The experiment was performed with the number of mouse cases in each group as n=4 and their average values were plotted with ±SE error bars. Twelve immune sera other than that of gD1-315V (E) of the thirteen modified gDs evaluated showed generally higher neutralizing antibody activity compared to immune sera of wild-type gD (gD1-315). That is, when comparing the plaque number-reducing rate of the same dilution fold at the same dose, the modified gD tended to exhibit a higher reducing rate than the wild-type gD.

The analysis results for anti-gD antibody-inducing activity by the ELISA method are shown in FIGS. 20-24. Symbols and line references in each graph were similar to those in the neutralizing antibody-inducing activity graph described above. In contrast to the results for neutralizing antibody activity, anti-gD-binding antibody activity in eleven immune sera other than that of gD1-315v5 (C), gD1-315V (F) and gD1-275 (J) of the fourteen modified gDs evaluated tended to exhibit relatively lower values compared to that of wild-type gD. That is, modified gD was found to induce higher neutralizing antibody activity with less binding antibody titer (antibody amount) than wild-type gD.

The above results are believed to be the result of being able to more efficiently and effectively induce an immune response to the remaining highly beneficial neutralizing epitopes by de-epitoping the deleterious and unbeneficial epitopes present a lot in the P50 peripheral region in the wild-type gD antigen by introduction of N-type glycochain. In other words, a biased immune response (immune deviation) to a wild-type gD antigen can have been ideally corrected (immune correction) by the present inventors' immune refocusing strategies.

Furthermore, for cellular immune (T cell immune) inducing activity, the IFN-γ production response activity (recall activity) of splenocytes (a pool sample of four cases) prepared from mice immunized with gD1-315v3-55 as an example of a modified gD antigen and wild-type gD (gD1-315) (3 μg/mouse of the administration group) was compared and analyzed. Specifically, 5 weeks old BALB/c mice were immunized with 3 μg of antigen subcutaneously in back at 2-week intervals for a total of 3 times, and splenocytes were collected 2 weeks after the final immunization. Anti-IFN-γ was immobilized in a 96-well plate with a PVDF membrane on the bottom surface and cells were seeded at $1\times10^6$ cells/100 μL/well. Immune antigens were added as stimulants at 10 mM and the cells were cultured at 37° C. and 5% $CO_2$ for 20 hours. The supernatant was removed and the anti-mouse IFNγ-HRP antibody was reacted, then HRP was stained with AEC reagents to count IFNγ-producing cell numbers with an Image Analyzer (CTL). The results are shown in FIG. 25. It was found that the gD1-315v3-55 immune group exhibits higher response activity than the wild-type gD immune group. It was found that cellular immune (T cell immune) inducing activity could be enhanced by linking two HLA Class II constrained promiscuous T cell epitope cluster DP5s to the C-terminal of the modified gD antigen.

<Mouse Infection-Prevention Test of Modified gD>

(Mouse Infection-Prevention Test)

An infection-prevention test in the preventive administration of modified gD antigen was performed using a mouse genital herpes infection model. Similar to the mouse immunogenicity test described above, mice were immunized with the number of N=10 cases per group. Depo-Provera was inoculated subcutaneously at 2 mg/mouse 6 days prior to viral inoculation to improve the multiplicity of infection upon viral inoculation 2 weeks after final immunization (third dose). $5\times10^5$ PFU/20 μL HSV-2 MS strain was inoculated transvaginally under anesthesia and observed for 21 days. Infection prevention ability was evaluated using survival time (survival rate) as index.

The infection model of the mouse genital herpes infection model was used to evaluate infection prevention ability of various modified gD in preventive administration. The number of animal cases in each group was set to n=10, and wild-type gD (gD1-315) was used as a positive control and saline was used as a negative control. The experiments were performed a total of four times (experiments 1-4) and four doses of 0.1 μg/mouse/time, 0.03 μg/mouse/time, 0.01 μg/mouse/time and 0.003 μg/mouse/time were set for all of the positive control, negative control, and subject modified gD antigen. Depo-Provera was inoculated subcutaneously at 2 mg/mouse 6 days prior to viral inoculation to improve the multiplicity of infection upon viral inoculation 2 weeks after final immunization (third dose). $5\times10^5$ PFU/20 HSV-2 MS strain was inoculated transvaginally under anesthesia and observed for 21 days. Infection prevention ability was evaluated using survival time (survival rate) as index. Mean values of those were plotted in the graph. A Significant difference test for the negative control group was performed by the Kaplan-Meier method, and those with a minimum effective dose based on the Significant difference test in three-fold common ratio relative to wild type gD of two or more doses stronger were determined to be "++", those of one dose stronger were determined to be "+", and those of an equivalent value were determined to be "±".

The results of Experiment 1 are shown in Table 13 and FIGS. 26-28. All six modified gDs evaluated showed superiority to wild type gD, of which those determined to be "++" were three, gD1-315v3-55, gD1-315v5-55V and gD1-275v5-55, and those determined to be "+" were three, gD1-315v5, gD1-315v4V, and gD1-315v4-55V.

TABLE 13

Experiment 1 Survival time table

| Sample | Inoculation amount (μg/head/time) | Survival time after infection (days) | Mean survival time (days) | Significant difference test (vs saline) | Determination (vs gD1-315) |
|---|---|---|---|---|---|
| gD1-315(WT) | 0.1 | >21, >21, >21, >21, >21, >21, >21, >21, >21 | >21 | *** | |
| | 0.03 | >21, >21, >21, >21, >21, >21, >21, >21, >21, >21 | >21 | *** | |
| | 0.01 | 5, 6, 6, 6, 7, 7, 7, 7, 10, 11 | 7 | N.S. | |
| | 0.003 | 5, 6, 6, 6, 6, 7, 8, 8, 9, >21 | 6.5 | N.S. | |
| gD1-315v5 | 0.1 | >21, >21, >21, >21, >21, >21, >21, >21, >21, >21 | >21 | *** | + |
| | 0.03 | 13, >21, >21, >21, >21, >21, >21, >21, >21, >21 | >21 | *** | |
| | 0.01 | 12, 13, 15, 18, >21, >21, >21, >21, >21 | >21 | *** | |
| | 0.003 | 6, 6, 6, 6, 6, 7, 7, 7, 8, >21 | 6.5 | N.S. | |
| gD1-315v3-55 | 0.1 | >21, >21, >21, >21, >21, >21, >21, >21, >21, >21 | >21 | *** | ++ |
| | 0.03 | >21, >21, >21, >21, >21, >21, >21, >21, >21, >21 | >21 | *** | |
| | 0.01 | 7, 8, 11, 13, 15, >21, >21, >21, >21 | 15 | *** | |
| | 0.003 | 7, 10, 10, 11, 11, >21, >21, >21, >21, >21 | >16 | *** | |
| gD1-315v5-55V | 0.1 | 8, 13, >21, >21, >21, >21, >21, >21, >21, >21 | >21 | *** | ++ |
| | 0.03 | 8, 10, 10, 11, >21, >21, >21, >21, >21, >21 | >21 | *** | |
| | 0.01 | 8, 10, 10, >21, >21, >21, >21, >21, >21 | >21 | *** | |
| | 0.003 | 6, 6, 6, 7, 9, 11, 13, 13, >21, >21 | 10 | ** | |
| gD1-315v4V | 0.1 | >21, >21, >21, >21, >21, >21, >21, >21, >21, >21 | >21 | *** | + |
| | 0.03 | 7, 9, 10, 11, 13, >21, >21, >21, >21, | >17 | *** | |
| | 0.01 | 5, 7, 8, 8, 10, 11, 11, >21, >21, >21 | 10.5 | ** | |
| | 0.003 | 5, 6, 6, 6, 7, 7, 9, 10, 13, >21 | 7 | N.S. | |
| gD-315v4-55V | 0.1 | 13, >21, >21, >21, >21, >21, >21, >21, >21, >21 | >21 | *** | + |
| | 0.03 | 11, 13, >21, >21, >21, >21, >21, >21, >21, >21 | >21 | *** | |
| | 0.01 | 6, 6, 8, 10, >21, >21, >21, >21, >21 | >21 | *** | |
| | 0.003 | 5, 6, 6, 6, 7, 7, 9, 18, >21, >21, | 7 | N.S. | |
| gD1-275v5-55 | 0.1 | 12, 13, >21, >21, >21, >21, >21, >21, >21, >21 | >21 | *** | ++ |
| | 0.03 | 11, 13, >21, >21, >21, >21, >21, >21, >21, >21 | >21 | *** | |
| | 0.01 | 7, 7, 10, 10, 11, 11, >21, >21, >21, >21 | 11 | *** | |
| | 0.003 | 6, 7, 7, 10, 11, 15, >21, >21, >21, >21 | 13 | *** | |
| saline | | 5, 5, 6, 6, 6, 6, 7, 7, 7, 8 | 6 | | |

[Significant difference test]
*** $p < 0.001$/
** $0.001 = < p < 0.01$/
* $0.01 = < p < 0.05$ (Kaplan-Meier method)
[Determination#] Those with a minimum effective dose based on the Significant difference test in three-fold common ratio relative to gD1-315(WT) of two or more doses stronger were determined to be "++", those of one dose stronger were determined to be "+", and those of an equivalent value were determined to be "±".

Figure 29:
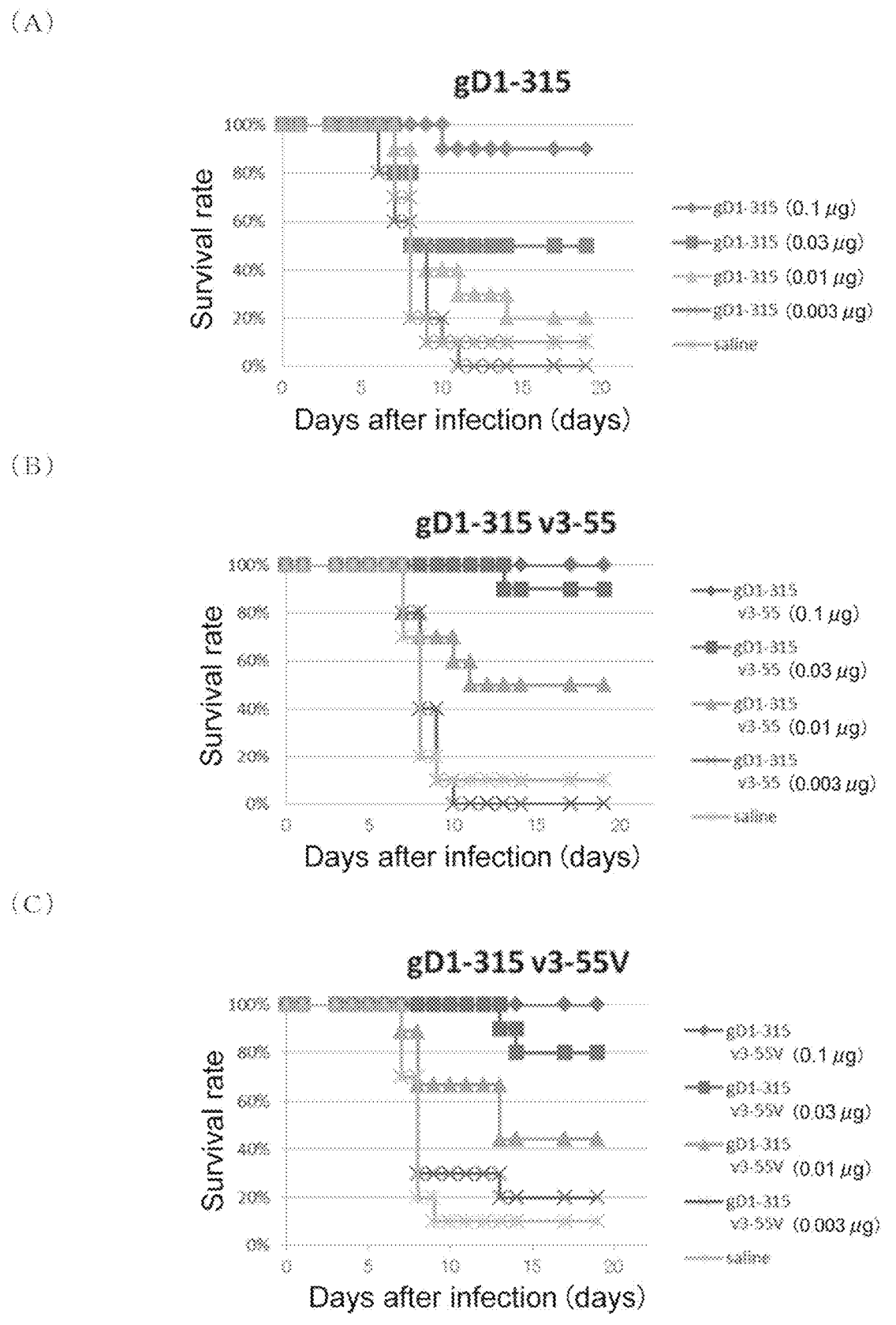
Figure 30:
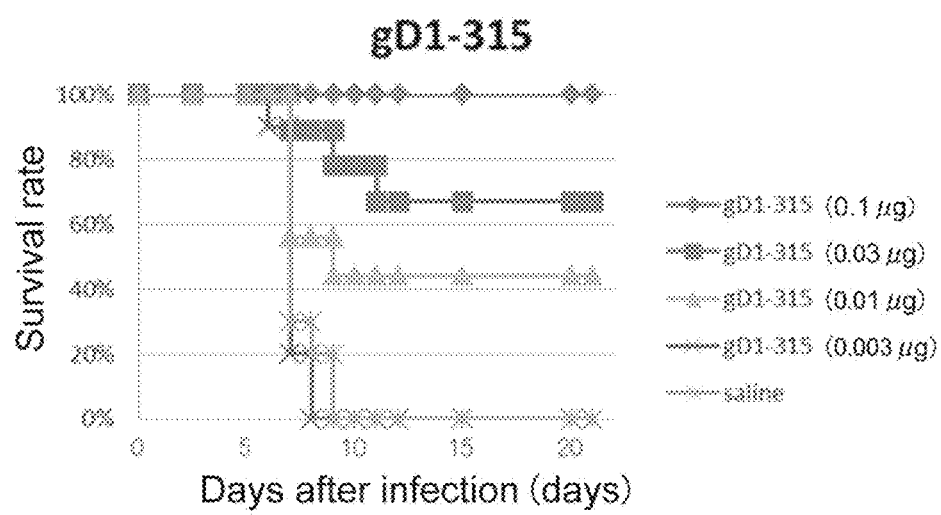
FIG. 30 presents diagrams showing the survival rate of mouse infection-prevention test Experiment 3 of the modified gD in Example 9.
Figure 30:
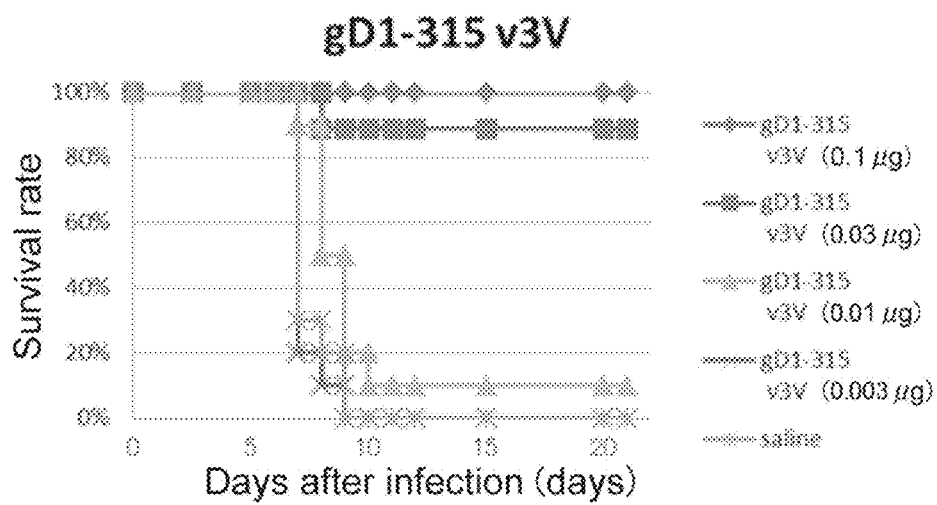

The results of Experiment 2 are shown in Table 14 and FIG. 29. The two evaluated variants, gD1-315v3-55 and gD1-315v3-55V, were both determined to be "+", indicating superiority over wild-type gD.

TABLE 14

| Experiment 2 (Survival time table) | | | | | |
|---|---|---|---|---|---|
| Sample | Inoculation amount (μg/head/time) | Survival time after infection (days) | Mean survival time (days) | Significant difference test (vs saline) | Determination# (vs gD1-315) |
| gD1-315(WT) | 0.1 | 9, >22, >22, >22, >22, >22, >22, >22, >22, >22 | >22 | *** | |
| | 0.03 | 6, 6, 7, 7, 7, >22, >22, >22, >22, >22 | >14.5 | N.S. | |
| | 0.01 | 6, 7, 7, 7, 7, 8, 10, 13, >22, >22 | 7.5 | N.S. | |
| | 0.003 | 5, 5, 6, 6, 7, 8, 8, 8, 8, 10 | 7.5 | N.S. | |
| gD1-315v3-55 | 0.1 | >22, >22, >22, >22, >22, >22, >22, >22, >22, >22 | >22 | *** | + |
| | 0.03 | 12, 16, >22, >22, >22, >22, >22, >22, >22, >22 | >22 | *** | |
| | 0.01 | 6, 6, 7, 9, 10, >22, >22, >22, >22, >22 | >16 | N.S. | |
| | 0.003 | 6, 6, 7, 7, 7, 7, 8, 8, 8, 9 | 7 | N.S. | |
| gD1-315v3-55v | 0.1 | 11, >22, >22, >22, >22, >22, >22, >22, >22, >22 | >22 | *** | + |
| | 0.03 | 12, 13, 16, >22, >22, >22, >22, >22, >22, >22 | >22 | ** | |
| | 0.01 | 6, 7, 7, 11, 11, >22, >22, >22, >22 | >16.5 | N.S. | |
| | 0.003 | 6, 6, 6, 7, 7, 7, 12, >22, >22 | 7 | N.S. | |
| saline | | 6, 6, 6, 7, 7, 7, 7, 8, >22 | 7 | | |

[Significant difference test]
*** p < 0.001/
** 0.001 = < p < 0.01/
* 0.01 = < p < 0.05 (Kaplan-Meier method)
[Determination#] Those with a minimum effective dose based on the Significant difference test in three-fold common ratio relative to gD1-315(WT) of two or more doses stronger were determined to be "++", those of one dose stronger were determined to be "+", and those of an equivalent value were determined to be "±".

The results of Experiment 3 are shown in Table 15 and FIG. 30. The determination of the variant gD1-315v3V evaluated was "±", and no definite superiority was found over wild-type gD.

TABLE 15

Experiment 3 (Survival time table)

| Sample | Inoculation amount (μg/head/time) | Survival time after infection (days) | Mean survival time (days) | Significant difference test (vs saline) | Determination# (vs gD1-315) |
|---|---|---|---|---|---|
| gD1-315(WT) | 0.1 | >21, >21, >21, >21, >21, >21, >21, >21, >21 | >21 | *** | |
| | 0.03 | 6, 8, 10, >21, >21, >21, >21, >21, >21 | >21 | *** | |
| | 0.01 | 6, 6, 6, 6, 8, >21, >21, >21, >21 | 8 | * | |
| | 0.003 | 5, 6, 6, 6, 6, 6, 6, 6, 6, 7, 7 | 6 | N.S. | |
| gD1-315v3V | 0.1 | >21, >21, >21, >21, >21, >21, >21, >21, >21 | >21 | *** | ± |
| | 0.03 | 7, >21, >21, >21, >21, >21, >21, >21, >21 | >21 | *** | |
| | 0.01 | 6, 7, 7, 7, 7, 8, 8, 8, 9 | 7 | * | |
| | 0.03 | 6, 6, 6, 6, 6, 6, 6, 6, 7, 8 | 6 | N.S. | |
| saline | | 6, 6, 6, 6, 6, 6, 7, 7, 8, 8 | 6 | | |

[Significant difference test]
*** p < 0.001/
** 0.001 = < p < 0.01/
* 0.01 = < p < 0.05 (Kaplan-Meier method)
[Determination#] Those with a minimum effective dose based on the Significant difference test in three-fold common ratio relative to gD1-315(WT) of two or more doses stronger were determined to be "++", those of one dose stronger were determined to be "+", and those of an equivalent value were determined to be "±".

Figure 31:
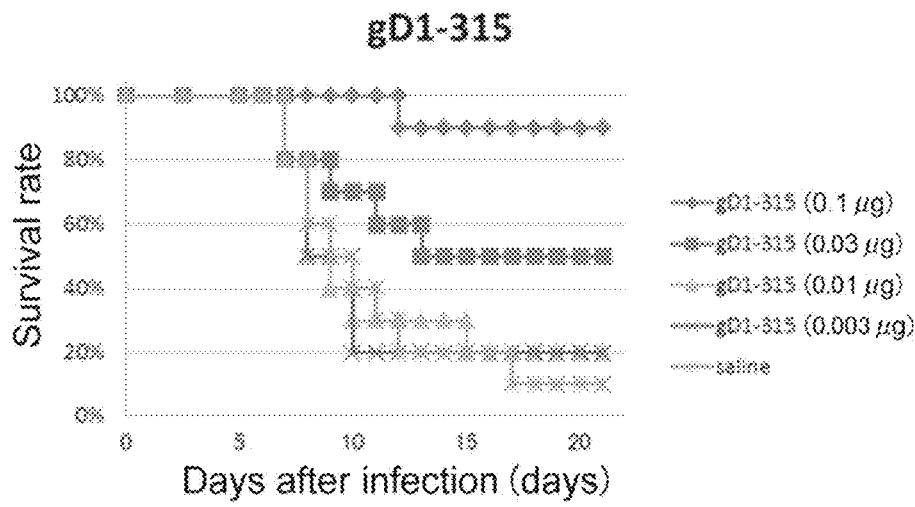
FIG. 31 presents diagrams showing the survival rate of mouse infection-prevention test Experiment 4 of the modified gD in Example 9.
Figure 31:
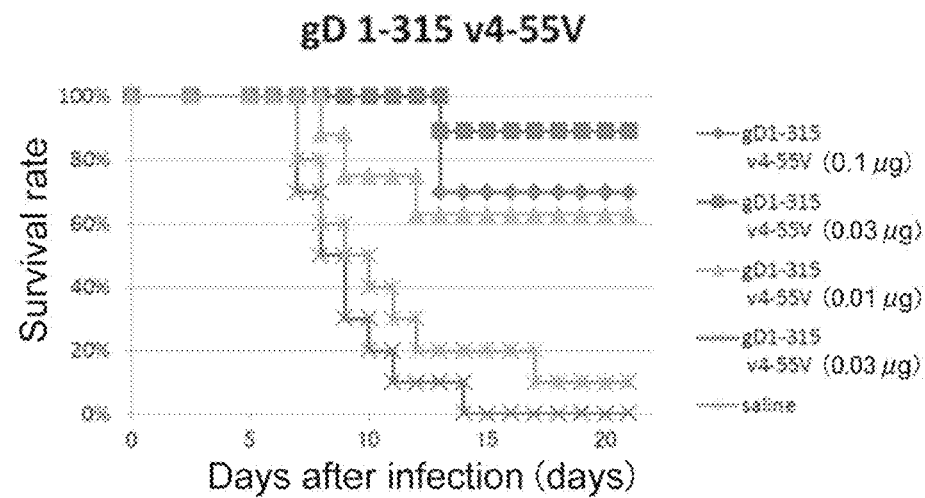
Figure 31:
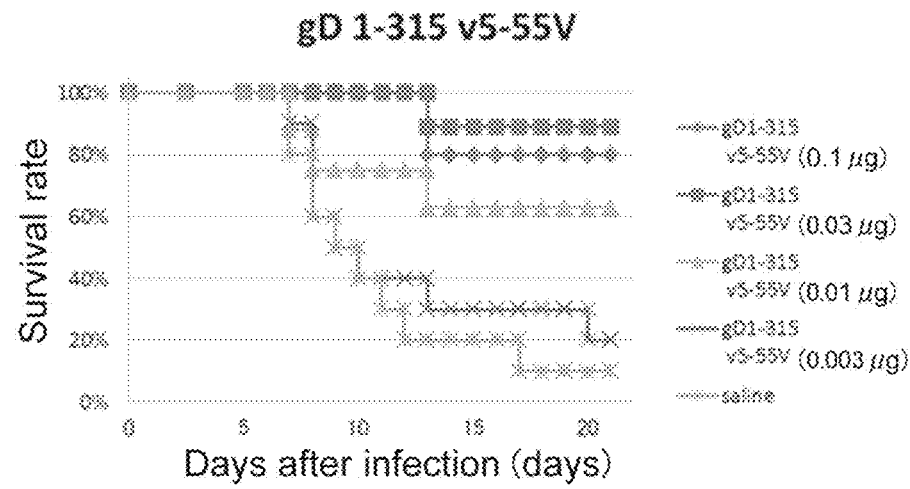
Figure 32:
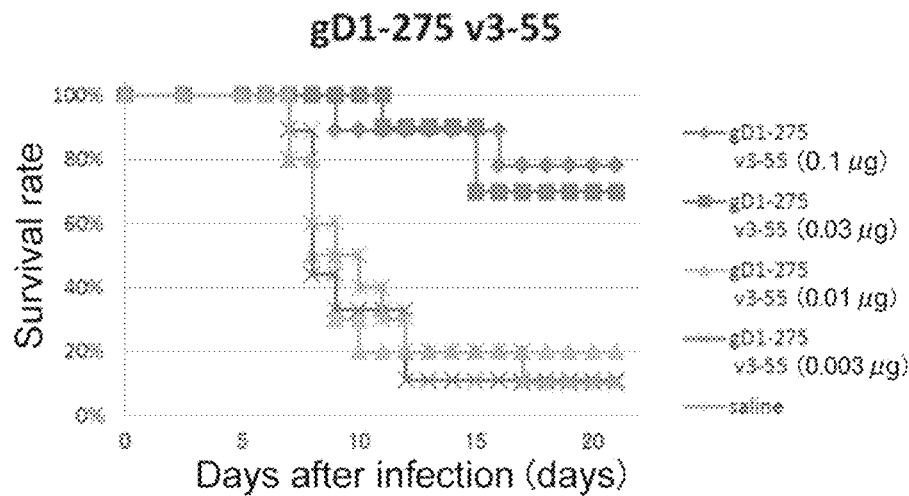
FIG. 32 presents diagrams showing the survival rate of mouse infection-prevention test Experiment 4 of the modified gD in Example 9.
Figure 32:
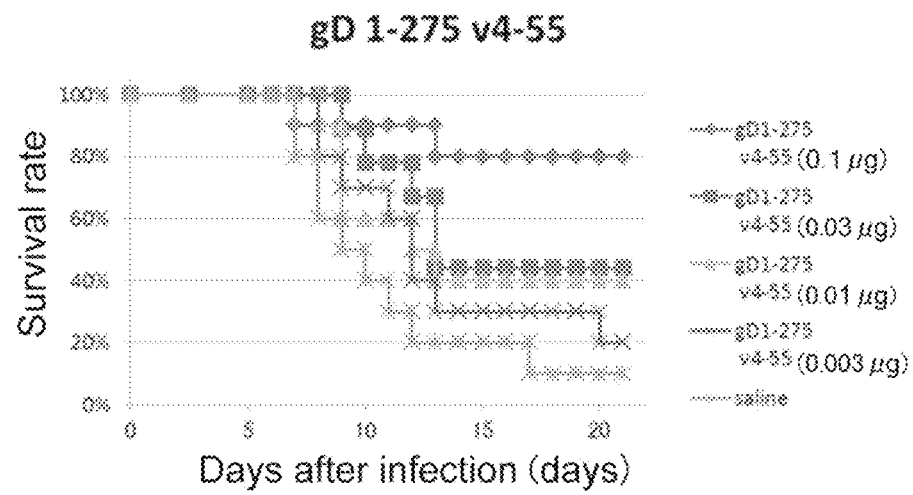
Figure 32:
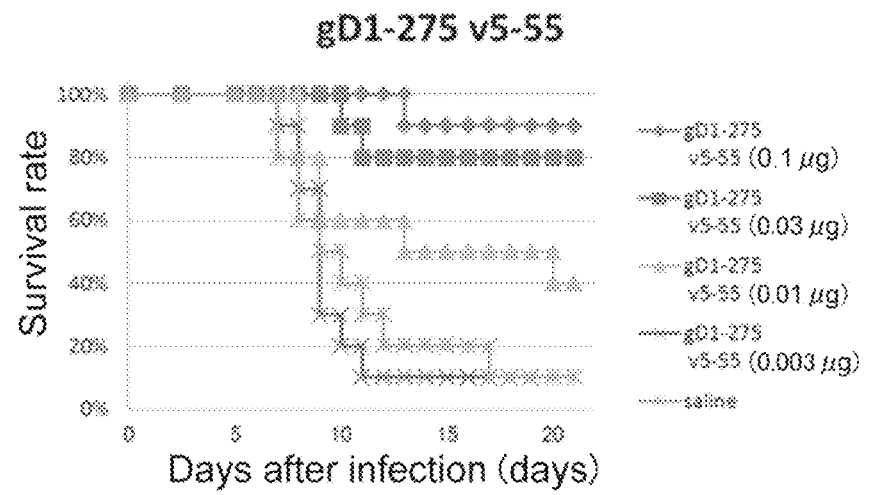

The results of Experiment 4 are shown in Table 16 and FIG. 31 to FIG. 32. All five modified gDs evaluated exhibited superiority over wild type gD, of which those determined to be "++" were two, gD1-315v4-55V and gD1-315v5-55V, and those determined to be "+" were three, gD1-275v3-55, gD1-275v4-55 and gD1-275v5-55.

TABLE 16

Experiment 4 (Survival time table)

| Sample | Inoculation amount (μg/head/time) | Survival time after infection (days) | Mean survival time (days) | Significant difference test (vs saline) | Determination# (vs gD1-315) |
|---|---|---|---|---|---|
| gD1-315(WT) | 0.1 | 11, >21, >21, >21, >21, >21, >21, >21, >21, >21 | >21 | *** | |
| | 0.03 | 6, 6, ,7, 10, 12, >21, >21, >21, >21, >21 | >16.5 | N.S. | |
| | 0.01 | 6, 6, 7, 7, 7, 8, 9, 14, >21, >21 | 7.5 | N.S. | |
| | 0.003 | 6, 6, 7, 7, 7, 8, 9, 10, >21, >21 | 8 | N.S. | |
| gD1-315v4-55V | 0.1 | 12, 12, 12, >21, >21, >21, >21, >21, >21, >21 | >21 | *** | ++ |
| | 0.03 | 12, >21, >21, >21, >21, >21, >21, >21, >21 | >21 | *** | |
| | 0.01 | 7, 8, 11, >21, >21, >21, >21, >21 | >21 | ** | |
| | 0.003 | 6, 6, 6, 7, 7, 8, 8, 9, 10, 13, | 7.5 | N.S. | |
| gD1-315v5-55V | 0.1 | 12, 12, >21, >21, >21, >21, >21, >21, >21, >21 | >21 | *** | ++ |
| | 0.03 | 12, >21, >21, >21, >21, >21, >21, >21, >21 | >21 | *** | |
| | 0.01 | 6, 7, 12, >21, >21, >21, >21, >21, | >21 | * | |
| | 0.03 | 6, 7, 7, 8, 8, 9, 12, >21, >21, >21 | 8.5 | N.S. | |
| gD1-275v3-55 | 0.1 | 8, 15, >21, >21, >21, >21, >21, >21, >21 | >21 | ** | + |
| | 0.03 | 10, 14, 14, >21, >21, >21, >21, >21, >21, >21 | >21 | ** | |
| | 0.01 | 6, 6, 7, 7, 7, 8, 8, 9, >21, >21 | 7.5 | N.S. | |
| | 0.003 | 6, 7, 7, 7, 7, 8, 11, 11, >21 | 7 | N.S. | |
| gD1-275v4-55 | 0.1 | 6, 12, >21, >21, >21, >21, >21, >21, >21, >21 | >21 | ** | + |
| | 0.03 | 8, 9, 11, 12, 12, >21, >21, >21, >21 | 12 | * | |
| | 0.01 | 7, 8, 8, 8, 11, 12, >21, >21, >21, >21 | 11.5 | N.S. | |
| | 0.003 | 7, 7, 8, 10, 11, 11, 12, 19, >21, >21 | 11 | N.S. | |
| gD1-275v5-55 | 0.1 | 12, >21, >21, >21, >21, >21, >21, >21, >21, >21 | >21 | *** | + |
| | 0.03 | 9, 10, >21, >21, >21, >21, >21, >21, >21, >21 | >21 | ** | |
| | 0.01 | 7, 7, 8, 8, 12, 19, >21, >21, >21, >21 | 15.5 | N.S. | |
| | 0.003 | 6, 7, 7, 8, 8, 8, 8, 9, 10, >21 | 8 | N.S. | |
| saline | | 6, 6, 7, 7, 8, 9;, 10, 11, 16, >21 | 8.5 | | |

[Significant difference test]
*** p < 0.001/
** 0.001 = < p < 0.01/
* 0.01 = < p < 0.05 (Kaplan-Meier method)
[Determination#] Those with a minimum effective dose based on the Significant difference test in three-fold common ratio relative to gD1-315(WT) of two or more doses stronger were determined to be "++", those of one dose stronger were determined to be "+", and those of an equivalent value were determined to be "±".

From the above, for almost all modified gDs except gD1-315v3V, the superiority over wild-type gDs was confirmed in infection prevention ability as well as neutralizing antibody-inducing ability.

<Antibody Populations Analysis in Modified gD Immune Serum>

Of a series of modified gDs that were found to be superior to wild-type gD (gD1-315) in mouse immunogenicity test and mouse infection-prevention test, immune serum analysis was performed to examine their mechanisms for gD1-315v3-55 and gD1-315v5-55. Whether efficient induction of Antibody No. 82-like antibodies of interest was actually caused was investigated. IgG was purified from serum and analyzed by competitive methods using SPR (Biacore, Inc.) to make antibody amounts uniform.

(Anti-gD2 Antibody Competition Test by SPR)

The anti-gD2 antibody competition test was performed using Biacore 3000 (GE Healthcare), where, in all experiments, HBS-EP buffer (GE Healthcare) was used, the temperature was set to 25° C., and the flow rate was set to 20 µL/min. CM5 senor chip (GE Healthcare) was used as the sensor chip, and the experiment was performed based on the recommended protocol. gD1-315-His was immobilized at about 300 RU on the chip surface, and for chip regeneration, glycine-hydrochloride buffer of 0.1 M and pH 2.0 was used and the chip was washed twice at a flow rate of 30 µL/min for 30 seconds. Procedures for competition and calculation of the competition rate were as follows. 10 µg/mL of each anti-gD2 antibody or buffer was applied to the chip under a condition of binding for 1 minute and dissociation for 2.5 minutes. 20 µg/mL of each immune serum purified by IgG was then applied under a condition of binding for 1 minute and dissociation for 5 minutes. After buffer application, the RU detected when immune serum was applied was set to 100%, and the decrease in immune serum response by anti-gD2 antibody application was calculated as the competitive rate.

Figure 33:
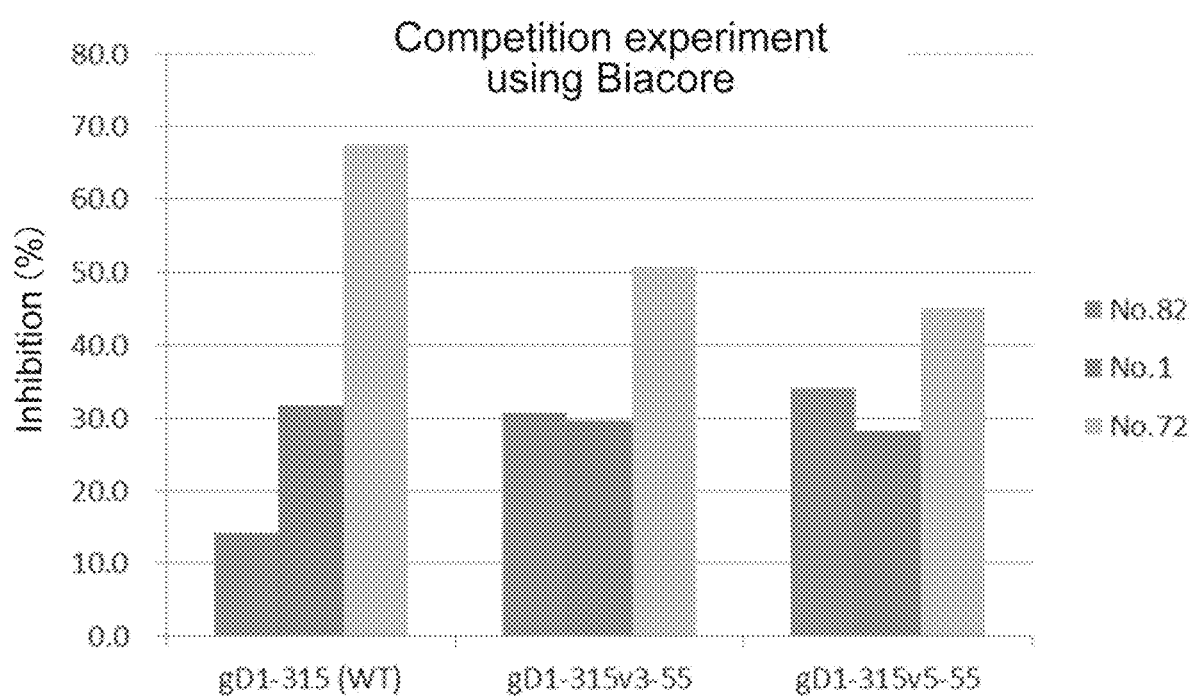
FIG. 33 presents a diagram showing the analysis results of antibody populations in the immune serum in Example 9.

The analysis results are shown in FIG. 33. Both the gD1-315v3-55 immune serum and the gD1-315v5-55 immune serum were found to have an increased percentage of antibodies competing with antibody No. 82 compared to wild-type gD immune serum. Meanwhile, the percentage of antibodies competing with antibody No. 72 having an epitope in the P50 peripheral region masked by N-type glycochain introduction was found to tend to decrease. Furthermore, little change was found in the percentage of antibodies competing with the non-neutralizing antibody No. 1 in which the epitope remained. From the above results, it was suggested that the modified gD immune serum is relatively abundant with antibody No. 82-like antibodies, which are good neutralizing antibodies, compared to wild-type gD immune serum, and induction of immune refocusing of interest has achieved.

(Competitive ELISA with gD Receptor)

Inhibition of gD-HVEM interactions by modified gD immune serum was also analyzed. Specifically, 100 µL of gD1-305-cys-strep dimer adjusted to a concentration of 5 µg/mL with phosphate buffered saline was immobilized in a 96-well microtiter plate at 4° C. overnight. Subsequently, blocking and washing were performed as in the competitive ELISA method described above, 100 µL of IgG purified from each immune serum was added at any concentration and reacted at room temperature for one hour. Subsequently, 1 µg/mL of HVEM (Recombinant Human HVEM/TN-FRSF14 Fc Chimera Protein, R&D SYSTEMS, Inc.) was diluted at any dilution fold with 1% BSA PBS, each added at 100 µL and reacted at room temperature for an additional hour. Each well was washed again with PBS-T, then, HRP-labeled antibody (anti-hFc/HRP/1% BSA PBS) was reacted. Each well was washed with PBS-T, then colored, and after the reaction was stopped with 1N sulfuric acid, absorbance of 450 nm/650 nm was measured.

Figure 34:
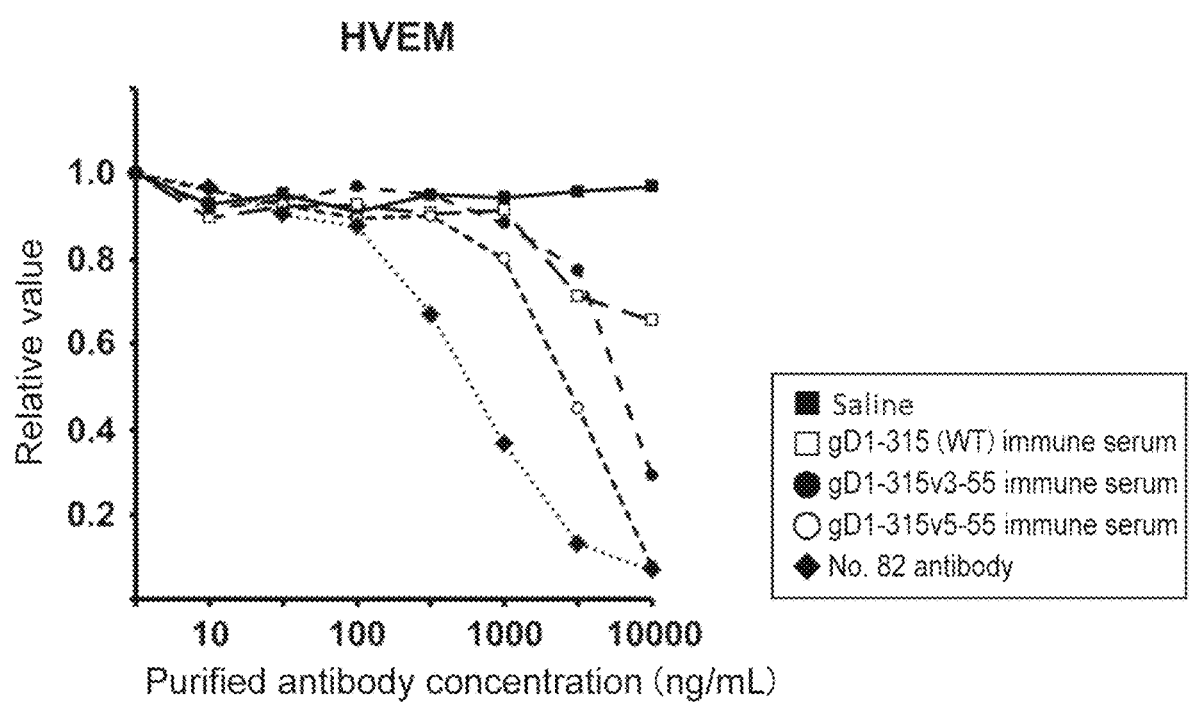
FIG. 34 presents a diagram showing the results of inhibition of gD-HVEM interactions with the modified gD immune serum in Example 9.

The results are shown in FIG. 34. Antibodies that inhibit the gD-HVEM interaction were more present in the modified gD immune serum than in the wild-type gD immune serum, particularly the gD1-315v5-55 immune serum showed strong inhibitory effects. From the above results, it was suggested that modified gD may have a stronger preventive effect by inducing high-quality antibodies capable of inhibiting the interaction of gD and HVEM more efficiently than wild-type gD.

INDUSTRIAL APPLICABILITY

Modified HSV gD proteins of the present invention can be used in the production of vaccines effective for prevention and treatment of HSV infections.

The invention claimed is:

1. A modified herpes simplex virus (HSV) envelope glycoprotein D (gD) (modified HSV gD), wherein the modified HSV gD is derived from a wild-type HSV gD by
   introducing a glycochain to an amino acid residue corresponding to a proline residue at position 50 in the amino acid sequence set forth in SEQ ID NO: 1 in the ectodomain of the wild-type HSV gD,
   introducing a glycochain to an amino acid residue corresponding to a proline residue at position 74 in the amino acid sequence set forth in SEQ ID NO: 1 in the ectodomain of the wild-type HSV gD, and/or,
   introducing a glycochain to an amino acid residue corresponding to an arginine residue at position 186 in the amino acid sequence set forth in SEQ ID NO: 1 in the ectodomain of the wild-type HSV gD.

2. A modified herpes simplex virus (HSV) envelope glycoprotein D (gD) (modified HSV gD), wherein
   the ectodomain of the wild-type HSV gD consists of the amino acid sequence set forth in SEQ ID NO: 1; and
   the modification of the decotope includes at least one modification selected from the group consisting of:
      a modification by introducing a glycochain by substitution of a proline residue at position 50 with an asparagine residue and substitution of a proline residue at position 51 with an amino acid residue other than a proline residue in the amino acid sequence set forth in SEQ ID NO: 1;
      a modification by introducing a glycochain by substitution of a proline residue at position 74 with an asparagine residue and substitution of a glutamic acid residue at position 76 with a serine residue in the amino acid sequence set forth in SEQ ID NO: 1; and
      a modification by introducing a glycochain by substitution of an arginine residue at position 186 with an asparagine residue in the amino acid sequence set forth in SEQ ID NO: 1.

3. The modified HSV gD according to claim 1, wherein the glycochain is an N-type glycochain.

4. The modified HSV gD according to claim 1, wherein the modified HSV gD further comprises at least one promiscuous T cell epitope linked at a C-terminal side of the ectodomain of the HSV gD.

5. The modified HSV gD according to claim 4, wherein the promiscuous T cell epitope is a promiscuous T cell epitope consisting of the amino acid sequence set forth in SEQ ID NO: 4, SEQ ID NO: 5, SEQ ID NO: 6, SEQ ID NO: 7, or SEQ ID NO: 8.

6. The modified HSV gD according to claim 5, wherein the promiscuous T cell epitope is a promiscuous T cell epitope consisting of the amino acid sequence set forth in SEQ ID NO: 8.

7. The modified HSV gD according to claim 1, wherein the modified HSV gD further contains deletion of at least a portion of amino acid residues corresponding to amino acid residues at positions 251 to 315 in the amino acid sequence set forth in SEQ ID NO: 1 in the wild-type HSV gD.

8. The modified HSV gD according to claim 1, wherein the modified HSV gD further includes a modification by substitution of an amino acid residue corresponding to a valine residue at position 231 with another amino acid residue in the amino acid sequence set forth in SEQ ID NO: 1 in the ectodomain of the wild-type HSV gD.

9. The modified HSV gD according to claim 1, wherein the HSV is HSV-1 or HSV-2.

10. An HSV vaccine comprising the modified HSV gD according to claim 1.

11. The modified HSV gD according to claim 2, wherein the glycochain is an N-type glycochain.

12. The modified HSV gD according to claim 2, wherein the modified HSV gD further comprises at least one promiscuous T cell epitope linked at a C-terminal side of the ectodomain of the HSV gD.

13. The modified HSV gD according to claim 12, wherein the promiscuous T cell epitope is a promiscuous T cell epitope consisting of the amino acid sequence set forth in SEQ ID NO: 4, SEQ ID NO: 5, SEQ ID NO: 6, SEQ ID NO: 7, or SEQ ID NO: 8.

14. The modified HSV gD according to claim 13, wherein the promiscuous T cell epitope is a promiscuous T cell epitope consisting of the amino acid sequence set forth in SEQ ID NO: 8.

15. The modified HSV gD according to claim 2, wherein the modified HSV gD further contains deletion of at least a portion of amino acid residues corresponding to amino acid residues at positions 251 to 315 in the amino acid sequence set forth in SEQ ID NO: 1 in the wild-type HSV gD.

16. The modified HSV gD according to claim 2, wherein the modified HSV gD further includes a modification by substitution of an amino acid residue corresponding to a valine residue at position 231 with another amino acid residue in the amino acid sequence set forth in SEQ ID NO: 1 in the ectodomain of the wild-type HSV gD.

17. The modified HSV gD according to claim 2, wherein the HSV is HSV-1 or HSV-2.

18. An HSV vaccine comprising the modified HSV gD according to claim 2.

* * * * *

SEQUENCE LISTING

```
<160> NUMBER OF SEQ ID NOS: 34

<210> SEQ ID NO 1
<211> LENGTH: 315
<212> TYPE: PRT
<213> ORGANISM: Herpes simplex virus

<400> SEQUENCE: 1

Lys Tyr Ala Leu Ala Asp Pro Ser Leu Lys Met Ala Asp Pro Asn Arg
1               5                   10                  15

Phe Arg Gly Lys Asn Leu Pro Val Leu Asp Gln Leu Thr Asp Pro Pro
            20                  25                  30

Gly Val Lys Arg Val Tyr His Ile Gln Pro Ser Leu Glu Asp Pro Phe
        35                  40                  45

Gln Pro Pro Ser Ile Pro Ile Thr Val Tyr Tyr Ala Val Leu Glu Arg
    50                  55                  60

Ala Cys Arg Ser Val Leu Leu His Ala Pro Ser Glu Ala Pro Gln Ile
65                  70                  75                  80
```

```
Val Arg Gly Ala Ser Asp Glu Ala Arg Lys His Thr Tyr Asn Leu Thr
            85                  90                  95

Ile Ala Trp Tyr Arg Met Gly Asp Asn Cys Ala Ile Pro Ile Thr Val
        100                 105                 110

Met Glu Tyr Thr Glu Cys Pro Tyr Asn Lys Ser Leu Gly Val Cys Pro
        115                 120                 125

Ile Arg Thr Gln Pro Arg Trp Ser Tyr Tyr Asp Ser Phe Ser Ala Val
        130                 135                 140

Ser Glu Asp Asn Leu Gly Phe Leu Met His Ala Pro Ala Phe Glu Thr
145                 150                 155                 160

Ala Gly Thr Tyr Leu Arg Leu Val Lys Ile Asn Asp Trp Thr Glu Ile
                165                 170                 175

Thr Gln Phe Ile Leu Glu His Arg Ala Arg Ala Ser Cys Lys Tyr Ala
            180                 185                 190

Leu Pro Leu Arg Ile Pro Pro Ala Ala Cys Leu Thr Ser Lys Ala Tyr
        195                 200                 205

Gln Gln Gly Val Thr Val Asp Ser Ile Gly Met Leu Pro Arg Phe Ile
        210                 215                 220

Pro Glu Asn Gln Arg Thr Val Ala Leu Tyr Ser Leu Lys Ile Ala Gly
225                 230                 235                 240

Trp His Gly Pro Lys Pro Pro Tyr Thr Ser Thr Leu Leu Pro Pro Glu
                245                 250                 255

Leu Ser Asp Thr Thr Asn Ala Thr Gln Pro Glu Leu Val Pro Glu Asp
            260                 265                 270

Pro Glu Asp Ser Ala Leu Leu Glu Asp Pro Ala Gly Thr Val Ser Ser
        275                 280                 285

Gln Ile Pro Pro Asn Trp His Ile Pro Ser Ile Gln Asp Val Ala Pro
        290                 295                 300

His His Ala Pro Ala Ala Pro Ser Asn Pro Gly
305                 310                 315

<210> SEQ ID NO 2
<211> LENGTH: 394
<212> TYPE: PRT
<213> ORGANISM: Herpes simplex virus-1

<400> SEQUENCE: 2

Met Gly Gly Ala Ala Ala Arg Leu Gly Ala Val Ile Leu Phe Val Val
-25                 -20                 -15                 -10

Ile Val Gly Leu His Gly Val Arg Gly Lys Tyr Ala Leu Ala Asp Ala
            -5                  1                   5

Ser Leu Lys Met Ala Asp Pro Asn Arg Phe Arg Gly Lys Asp Leu Pro
        10                  15                  20

Val Leu Asp Gln Leu Thr Asp Pro Pro Gly Val Arg Arg Val Tyr His
        25                  30                  35

Ile Gln Ala Gly Leu Pro Asp Pro Phe Gln Pro Ser Leu Pro Ile
40                  45                  50                  55

Thr Val Tyr Tyr Ala Val Leu Glu Arg Ala Cys Arg Ser Val Leu Leu
                60                  65                  70

Asn Ala Pro Ser Glu Ala Pro Gln Ile Val Arg Gly Ala Ser Glu Asp
            75                  80                  85

Val Arg Lys Gln Pro Tyr Asn Leu Thr Ile Ala Trp Phe Arg Met Gly
        90                  95                  100

Gly Asn Cys Ala Ile Pro Ile Thr Val Met Glu Tyr Thr Glu Cys Ser
```

```
        105                 110                 115
Tyr Asn Lys Ser Leu Gly Ala Cys Pro Ile Arg Thr Gln Pro Arg Trp
120                 125                 130                 135

Asn Tyr Tyr Asp Ser Phe Ser Ala Val Ser Glu Asp Asn Leu Gly Phe
                140                 145                 150

Leu Met His Ala Pro Ala Phe Glu Thr Ala Gly Thr Tyr Leu Arg Leu
            155                 160                 165

Val Lys Ile Asn Asp Trp Thr Glu Ile Thr Gln Phe Ile Leu Glu His
        170                 175                 180

Arg Ala Lys Gly Ser Cys Lys Tyr Ala Leu Pro Leu Arg Ile Pro Pro
    185                 190                 195

Ser Ala Cys Leu Ser Pro Gln Ala Tyr Gln Gln Gly Val Thr Val Asp
200                 205                 210                 215

Ser Ile Gly Met Leu Pro Arg Phe Ile Pro Glu Asn Gln Arg Thr Val
                220                 225                 230

Ala Val Tyr Ser Leu Lys Ile Ala Gly Trp His Gly Pro Lys Ala Pro
            235                 240                 245

Tyr Thr Ser Thr Leu Leu Pro Pro Glu Leu Ser Glu Thr Pro Asn Ala
        250                 255                 260

Thr Gln Pro Glu Leu Ala Pro Glu Asp Pro Glu Asp Ser Ala Leu Leu
    265                 270                 275

Glu Asp Pro Val Gly Thr Val Ala Pro Gln Ile Pro Pro Asn Trp His
280                 285                 290                 295

Ile Pro Ser Ile Gln Asp Ala Ala Thr Pro Tyr His Pro Pro Ala Thr
                300                 305                 310

Pro Asn Asn Met Gly Leu Ile Ala Gly Ala Val Gly Gly Ser Leu Leu
            315                 320                 325

Ala Ala Leu Val Ile Cys Gly Ile Val Tyr Trp Met His Arg Arg Thr
        330                 335                 340

Arg Lys Ala Pro Lys Arg Ile Arg Leu Pro His Ile Arg Glu Asp Asp
    345                 350                 355

Gln Pro Ser Ser His Gln Pro Leu Phe Tyr
360                 365

<210> SEQ ID NO 3
<211> LENGTH: 393
<212> TYPE: PRT
<213> ORGANISM: Herpes simplex virus-2

<400> SEQUENCE: 3

Met Gly Arg Leu Thr Ser Gly Val Gly Thr Ala Ala Leu Leu Val Val
-25                 -20                 -15                 -10

Ala Val Gly Leu Arg Val Val Cys Ala Lys Tyr Ala Leu Ala Asp Pro
                -5                  1                   5

Ser Leu Lys Met Ala Asp Pro Asn Arg Phe Arg Gly Lys Asn Leu Pro
            10                  15                  20

Val Leu Asp Gln Leu Thr Asp Pro Pro Gly Val Lys Arg Val Tyr His
        25                  30                  35

Ile Gln Pro Ser Leu Glu Asp Pro Phe Gln Pro Ser Ile Pro Ile
40                  45                  50                  55

Thr Val Tyr Tyr Ala Val Leu Glu Arg Ala Cys Arg Ser Val Leu Leu
                60                  65                  70

His Ala Pro Ser Glu Ala Pro Gln Ile Val Arg Gly Ala Ser Asp Glu
            75                  80                  85
```

-continued

```
Ala Arg Lys His Thr Tyr Asn Leu Thr Ile Ala Trp Tyr Arg Met Gly
         90                  95                 100

Asp Asn Cys Ala Ile Pro Ile Thr Val Met Glu Tyr Thr Glu Cys Pro
    105                 110                 115

Tyr Asn Lys Ser Leu Gly Val Cys Pro Ile Arg Thr Gln Pro Arg Trp
120                 125                 130                 135

Ser Tyr Tyr Asp Ser Phe Ser Ala Val Ser Glu Asp Asn Leu Gly Phe
                140                 145                 150

Leu Met His Ala Pro Ala Phe Glu Thr Ala Gly Thr Tyr Leu Arg Leu
            155                 160                 165

Val Lys Ile Asn Asp Trp Thr Glu Ile Thr Gln Phe Ile Leu Glu His
        170                 175                 180

Arg Ala Arg Ala Ser Cys Lys Tyr Ala Leu Pro Leu Arg Ile Pro Pro
    185                 190                 195

Ala Ala Cys Leu Thr Ser Lys Ala Tyr Gln Gln Gly Val Thr Val Asp
200                 205                 210                 215

Ser Ile Gly Met Leu Pro Arg Phe Ile Pro Glu Asn Gln Arg Thr Val
                220                 225                 230

Ala Leu Tyr Ser Leu Lys Ile Ala Gly Trp His Gly Pro Lys Pro Pro
            235                 240                 245

Tyr Thr Ser Thr Leu Leu Pro Pro Glu Leu Ser Asp Thr Thr Asn Ala
        250                 255                 260

Thr Gln Pro Glu Leu Val Pro Glu Asp Pro Glu Asp Ser Ala Leu Leu
    265                 270                 275

Glu Asp Pro Ala Gly Thr Val Ser Ser Gln Ile Pro Pro Asn Trp His
280                 285                 290                 295

Ile Pro Ser Ile Gln Asp Val Ala Pro His His Ala Pro Ala Ala Pro
                300                 305                 310

Ser Asn Pro Gly Leu Ile Ile Gly Ala Leu Ala Gly Ser Thr Leu Ala
            315                 320                 325

Val Leu Val Ile Gly Gly Ile Ala Phe Trp Val Arg Arg Arg Ala Gln
        330                 335                 340

Met Ala Pro Lys Arg Leu Arg Leu Pro His Ile Arg Asp Asp Asp Ala
    345                 350                 355

Pro Pro Ser His Gln Pro Leu Phe Tyr
360                 365

<210> SEQ ID NO 4
<211> LENGTH: 15
<212> TYPE: PRT
<213> ORGANISM: Herpes simplex virus-2

<400> SEQUENCE: 4

Lys Arg Val Tyr His Ile Gln Pro Ser Leu Glu Asp Pro Phe Gln
1               5                   10                  15

<210> SEQ ID NO 5
<211> LENGTH: 17
<212> TYPE: PRT
<213> ORGANISM: Herpes simplex virus-2

<400> SEQUENCE: 5

Ile Thr Val Tyr Tyr Ala Val Leu Glu Arg Ala Cys Arg Ser Val Leu
1               5                   10                  15

Leu
```

```
<210> SEQ ID NO 6
<211> LENGTH: 22
<212> TYPE: PRT
<213> ORGANISM: Herpes simplex virus-2

<400> SEQUENCE: 6

Ile Asn Asp Trp Thr Glu Ile Thr Gln Phe Ile Leu Glu His Arg Ala
1               5                   10                  15

Arg Ala Ser Cys Lys Tyr
            20

<210> SEQ ID NO 7
<211> LENGTH: 16
<212> TYPE: PRT
<213> ORGANISM: Herpes simplex virus-2

<400> SEQUENCE: 7

Pro Gly Leu Ile Ile Gly Ala Leu Ala Gly Ser Thr Leu Ala Val Leu
1               5                   10                  15

<210> SEQ ID NO 8
<211> LENGTH: 17
<212> TYPE: PRT
<213> ORGANISM: Herpes simplex virus-2

<400> SEQUENCE: 8

Ile Ala Phe Trp Val Arg Arg Arg Ala Gln Met Ala Pro Lys Pro Leu
1               5                   10                  15

Arg

<210> SEQ ID NO 9
<211> LENGTH: 5
<212> TYPE: PRT
<213> ORGANISM: Artificial Sequence
<220> FEATURE:
<223> OTHER INFORMATION: No.82 H-CDR1

<400> SEQUENCE: 9

Gly Tyr Ala Ile Asn
1               5

<210> SEQ ID NO 10
<211> LENGTH: 16
<212> TYPE: PRT
<213> ORGANISM: Artificial Sequence
<220> FEATURE:
<223> OTHER INFORMATION: No.82 H-CDR2

<400> SEQUENCE: 10

Gly Ile Met Pro Ile Phe Gly Thr Ser Asn Tyr Ala Gln Lys Phe Gln
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: No.82 H-CDR3

<400> SEQUENCE: 11

Asp Trp Gly Ala Pro Leu Glu Lys Gly Ala Gly Ser Pro Phe Asp Val
1               5                   10                  15

<210> SEQ ID NO 12
<211> LENGTH: 12
```

<212> TYPE: PRT
<213> ORGANISM: Artificial Sequence
<220> FEATURE:
<223> OTHER INFORMATION: No.82 L-CDR1

<400> SEQUENCE: 12

Arg Ala Ser Gln Ser Val Ser Ser Ser Tyr Leu Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: No.82 L-CDR2

<400> SEQUENCE: 13

Gly Ala Ser Ser Arg Ala Thr
1               5

<210> SEQ ID NO 14
<211> LENGTH: 9
<212> TYPE: PRT
<213> ORGANISM: Artificial Sequence
<220> FEATURE:
<223> OTHER INFORMATION: No.82 L-CDR3

<400> SEQUENCE: 14

Gln Gln Tyr Gly Ser Ser Pro Arg Ser
1               5

<210> SEQ ID NO 15
<211> LENGTH: 27
<212> TYPE: DNA
<213> ORGANISM: Artificial Sequence
<220> FEATURE:
<223> OTHER INFORMATION: SC-A-Fw

<400> SEQUENCE: 15
cgggccaatg cctcctgcaa gtacgct                                          27

<210> SEQ ID NO 16
<211> LENGTH: 27
<212> TYPE: DNA
<213> ORGANISM: Artificial Sequence
<220> FEATURE:
<223> OTHER INFORMATION: SC-A-Re

<400> SEQUENCE: 16
ggaggcattg gcccggtgct ccaggat                                          27

<210> SEQ ID NO 17
<211> LENGTH: 33
<212> TYPE: DNA
<213> ORGANISM: Artificial Sequence
<220> FEATURE:
<223> OTHER INFORMATION: SC-B-Fw

<400> SEQUENCE: 17
gggtggaatg gcaccaagcc cccgtacacc agc                                   33

<210> SEQ ID NO 18
<211> LENGTH: 33
<212> TYPE: DNA
<213> ORGANISM: Artificial Sequence
<220> FEATURE:
<223> OTHER INFORMATION: SC-B-Re

```
<400> SEQUENCE: 18
gggcttggtg ccattccacc cggcgatttt taa                                    33

<210> SEQ ID NO 19
<211> LENGTH: 33
<212> TYPE: DNA
<213> ORGANISM: Artificial Sequence
<220> FEATURE:
<223> OTHER INFORMATION: SC-D-Fw

<400> SEQUENCE: 19
catgccaatt cgaccgcccc ccagatcgtg cgc                                    33

<210> SEQ ID NO 20
<211> LENGTH: 33
<212> TYPE: DNA
<213> ORGANISM: Artificial Sequence
<220> FEATURE:
<223> OTHER INFORMATION: SC-D-Re

<400> SEQUENCE: 20
gggggcggtc gaattggcat gtaggagcac gct                                    33

<210> SEQ ID NO 21
<211> LENGTH: 33
<212> TYPE: DNA
<213> ORGANISM: Artificial Sequence
<220> FEATURE:
<223> OTHER INFORMATION: SC-E-Fw

<400> SEQUENCE: 21
cgcatgaatg acacctgcgc tatccccatc acg                                    33

<210> SEQ ID NO 22
<211> LENGTH: 33
<212> TYPE: DNA
<213> ORGANISM: Artificial Sequence
<220> FEATURE:
<223> OTHER INFORMATION: SC-E-Re

<400> SEQUENCE: 22
agcgcaggtg tcattcatgc gataccaggc gat                                    33

<210> SEQ ID NO 23
<211> LENGTH: 33
<212> TYPE: DNA
<213> ORGANISM: Artificial Sequence
<220> FEATURE:
<223> OTHER INFORMATION: SC-F-Fw

<400> SEQUENCE: 23
ttccagaatg caagcatccc gatcactgtg tac                                    33

<210> SEQ ID NO 24
<211> LENGTH: 33
<212> TYPE: DNA
<213> ORGANISM: Artificial Sequence
<220> FEATURE:
<223> OTHER INFORMATION: SC-F-Re

<400> SEQUENCE: 24
cgggatgctt gcattctgga acgggtcctc cag                                    33

<210> SEQ ID NO 25
```

<210> SEQ ID NO 25
<211> LENGTH: 33
<212> TYPE: DNA
<213> ORGANISM: Artificial Sequence
<220> FEATURE:
<223> OTHER INFORMATION: SC-H-Fw

<400> SEQUENCE: 25
ctccccaatc gcacgccccc ggcagcgtgc ctc                           33

<210> SEQ ID NO 26
<211> LENGTH: 33
<212> TYPE: DNA
<213> ORGANISM: Artificial Sequence
<220> FEATURE:
<223> OTHER INFORMATION: SC-H-Re

<400> SEQUENCE: 26
cgggggcgtg cgattgggga gagcgtactt gca                           33

<210> SEQ ID NO 27
<211> LENGTH: 27
<212> TYPE: DNA
<213> ORGANISM: Artificial Sequence
<220> FEATURE:
<223> OTHER INFORMATION: SC-K-Fw

<400> SEQUENCE: 27
agcatcaata tcactgtgta ctacgca                                  27

<210> SEQ ID NO 28
<211> LENGTH: 27
<212> TYPE: DNA
<213> ORGANISM: Artificial Sequence
<220> FEATURE:
<223> OTHER INFORMATION: SC-K-Re

<400> SEQUENCE: 28
agtgatattg atgctggggg gctggaa                                  27

<210> SEQ ID NO 29
<211> LENGTH: 33
<212> TYPE: DNA
<213> ORGANISM: Artificial Sequence
<220> FEATURE:
<223> OTHER INFORMATION: SC-L-Fw

<400> SEQUENCE: 29
ggggctaatg acaccgcccg aaagcacacg tac                           33

<210> SEQ ID NO 30
<211> LENGTH: 33
<212> TYPE: DNA
<213> ORGANISM: Artificial Sequence
<220> FEATURE:
<223> OTHER INFORMATION: SC-L-Re

<400> SEQUENCE: 30
tcgggcggtg tcattagccc cgcgcacgat ctg                           33

<210> SEQ ID NO 31
<211> LENGTH: 27
<212> TYPE: DNA
<213> ORGANISM: Artificial Sequence
<220> FEATURE:
<223> OTHER INFORMATION: SC-M-Fw

<400> SEQUENCE: 31

```
ataaacaatt ggacggagat cacacaa                                        27
```

<210> SEQ ID NO 32
<211> LENGTH: 27
<212> TYPE: DNA
<213> ORGANISM: Artificial Sequence
<220> FEATURE:
<223> OTHER INFORMATION: SC-M-Re

<400> SEQUENCE: 32

```
cgtccaattg tttatcttca ctagccg                                        27
```

<210> SEQ ID NO 33
<211> LENGTH: 1180
<212> TYPE: DNA
<213> ORGANISM: Herpes simplex virus-2

<400> SEQUENCE: 33

```
atggggcgtt tgacctccgg cgtcgggacg gcggccctgc tagttgtcgc ggtgggactc     60
cgcgtcgtct gcgccaaata cgccttagca gaccccctcgc ttaagatggc cgatcccaat   120
cgatttcgcg ggaagaacct tccggttttg gaccagctga ccgacccccc cggggtgaag   180
cgtgtttacc acattcagcc gagcctggag gacccgttcc agcccccccag catcccgatc   240
actgtgtact acgcagtgct ggaacgtgcc tgccgcagcg tgctcctaca tgccccatcg   300
gaggccccccc agatcgtgcg cggggcttcg gacgaggccc gaaagcacac gtacaacctg   360
accatcgcct ggtatcgcat gggagacaat tgcgctatcc ccatcacggt tatggaatac   420
accgagtgcc cctacaacaa gtcgttgggg gtctgcccca tccgaacgca gccccgctgg   480
agctactatg acagctttag cgccgtcagc gaggataacc tgggattcct gatgcacgcc   540
cccgccttcg agaccgcggg tacgtacctg cggctagtga agataaacga ctggacggag   600
atcacacaat ttatcctgga gcaccgggcc cgcgcctcct gcaagtacgc tctccccctg   660
cgcatccccc cggcagcgtg cctcacctcg aaggcctacc aacagggcgt gacggtcgac   720
agcatcggga tgctccccccg ctttatcccc gaaaaccagc gcaccgtcgc cctatacagc   780
ttaaaaatcg ccgggtggca cggccccaag ccccgtaca ccagcaccct gctgccgccg    840
gagctgtccg acaccaccaa cgccacgcaa cccgaactcg ttccggaaga ccccgaggac   900
tcggccctct tagaggatcc cgccgggacg gtgtcttcgc agatcccccc aaactggcac   960
atcccgtcga tccaggacgt cgccgccgcac cacgccccccg ccgccccccag caacccgggc  1020
ctgatcatcg gcgcgctggc cggcagtacc ctggcggtgc tggtcatcgg cggtattgcg  1080
ttttgggtac gccgccgcgc tcagatggcc cccaagcgcc tacgtctccc ccacatccgg  1140
gatgacgacg cgccccccctc gcaccagcca ttgttttact                        1180
```

<210> SEQ ID NO 34
<211> LENGTH: 5
<212> TYPE: PRT
<213> ORGANISM: Artificial Sequence
<220> FEATURE:
<223> OTHER INFORMATION: Linker peptide

<400> SEQUENCE: 34

Gly Pro Gly Pro Gly
1               5